US012691108B2

(12) United States Patent
Flynn et al.

(10) Patent No.: US 12,691,108 B2
(45) Date of Patent: Jul. 28, 2026

(54) METHODS FOR TREATING VASCULAR MALFORMATIONS

(71) Applicant: Deciphera Pharmaceuticals, LLC, Waltham, MA (US)

(72) Inventors: Daniel L. Flynn, Waltham, MA (US); Bryan D. Smith, Waltham, MA (US); Miikka Vikkula, Kraainem (BE)

(73) Assignee: Deciphera Pharmaceuticals, LLC, Waltham, MA (US)

( * ) Notice: Subject to any disclaimer, the term of this patent is extended or adjusted under 35 U.S.C. 154(b) by 0 days.

(21) Appl. No.: 16/991,644

(22) Filed: Aug. 12, 2020

(65) Prior Publication Data

US 2022/0047573 A1 Feb. 17, 2022
US 2023/0277522 A9 Sep. 7, 2023

Related U.S. Application Data

(60) Provisional application No. 62/885,519, filed on Aug. 12, 2019.

(51) Int. Cl.
*A61K 31/4709* (2006.01)
*A61K 45/06* (2006.01)
*A61P 9/00* (2006.01)

(52) U.S. Cl.
CPC .......... *A61K 31/4709* (2013.01); *A61K 45/06* (2013.01); *A61P 9/00* (2018.01)

(58) Field of Classification Search
CPC .... A61K 31/4155; A61K 31/4709; A61P 9/00
See application file for complete search history.

(56) References Cited

U.S. PATENT DOCUMENTS 3,528,980 A 9/1970 Islip
3,818,024 A 6/1974 Krenzer
3,939,122 A 2/1976 Merten et al.
3,949,002 A 4/1976 Feasey et al.
4,093,624 A 6/1978 Revankar et al.
4,296,237 A 10/1981 Cragoe, Jr. et al.
4,366,189 A 12/1982 Burdeska et al.
4,432,992 A 2/1984 Cragoe, Jr. et al.
4,525,450 A 6/1985 Itoh et al.
4,816,454 A 3/1989 Zoller et al.
5,103,014 A 4/1992 Musser et al.
5,162,360 A 11/1992 Creswell et al.
5,189,045 A 2/1993 Peglion et al.
5,319,099 A 6/1994 Kamata et al.
5,494,925 A 2/1996 Court et al.
5,514,691 A 5/1996 Chan et al.
5,621,010 A 4/1997 Sueda et al.
5,721,231 A 2/1998 Moriwaki et al.
5,811,456 A 9/1998 Seman et al.
6,020,357 A 2/2000 Pinto et al.
6,080,763 A 6/2000 Regan et al.
6,197,599 B1 3/2001 Chin et al.
6,235,786 B1 5/2001 Dai et al.
6,294,573 B1 9/2001 Curtin et al.
6,319,921 B1 11/2001 Cirillo et al.
6,410,254 B1 6/2002 Finer et al.
6,500,628 B1 12/2002 Robison
6,525,046 B1 2/2003 Cirillo et al.
6,645,990 B2 11/2003 Askew et al.
6,916,924 B2 7/2005 Tan et al.
7,071,199 B1 7/2006 Hirst et al.
7,135,550 B2 11/2006 Come et al.
7,144,911 B2 12/2006 Flynn et al.
7,202,257 B2 4/2007 Flynn et al.
7,211,575 B2 5/2007 Moss et al.
7,279,576 B2 10/2007 Flynn et al.
(Continued)

FOREIGN PATENT DOCUMENTS

CA 2 508 917 A1 7/2004
CN 106822128 A 6/2017
(Continued)

OTHER PUBLICATIONS

Harvey (Molecular Cancer Therapeutics vol. 16 pp. 2486-2501. Published 2017), (Year: 2017).*
Semones (Bioorganic and Medicinal Chemistry Letters vol. 17 pp. 4756-4760 published 2007) (Year: 2007).*
Reagan-Shaw (FASEBJ vol. 22 pp. 659-661) published 2007 (Year: 2007).*
Harney (Molecular Cancer Therapeutics vol. 16 pp. 2486-2501. Published 2017) (Year: 2017).*
Boscolo (Journal of Clinical Investigation vol. 125 pp. 3491-3504 published 2015) (Year: 2015).*
U.S. Appl. No. 11/963,740, filed Dec. 21, 2007, Granted, U.S. Pat. No. 8,163,756.
(Continued)

*Primary Examiner* — George W Kosturko
(74) *Attorney, Agent, or Firm* — Goodwin Procter LLP

(57) ABSTRACT

The present disclosure relates to methods for inhibiting TIE2 kinase useful in the treatment of growth of venous malformations. Specifically, the disclosure relates to methods of using a compound of Formula I and salts thereof Formula I

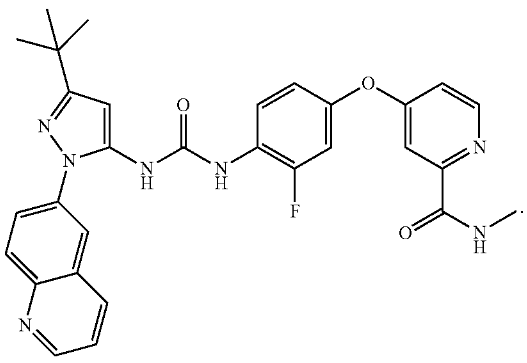

13 Claims, 35 Drawing Sheets

Specification includes a Sequence Listing.

(56) References Cited

U.S. PATENT DOCUMENTS

| | | | | |
|---|---|---|---|---|
| 7,342,037 | B2 | 3/2008 | Flynn et al. | |
| 7,531,566 | B2 | 5/2009 | Flynn et al. | |
| 7,666,895 | B2 | 2/2010 | Flynn et al. | |
| 7,737,283 | B2 | 6/2010 | Flynn et al. | |
| 7,790,756 | B2 | 9/2010 | Flynn et al. | |
| 7,897,762 | B2 | 3/2011 | Flynn et al. | |
| 8,143,293 | B2 | 3/2012 | Flynn et al. | |
| 8,163,756 | B2 | 4/2012 | Flynn et al. | |
| 8,188,113 | B2 | 5/2012 | Flynn et al. | |
| 8,278,331 | B2 | 10/2012 | Flynn et al. | |
| 8,461,179 | B1 | 6/2013 | Flynn et al. | |
| 8,486,951 | B2 | 7/2013 | Flynn et al. | |
| 8,569,319 | B2 | 10/2013 | Flynn et al. | |
| 8,586,565 | B2 | 11/2013 | Flynn et al. | |
| 8,637,672 | B2 | 1/2014 | Flynn et al. | |
| 8,669,289 | B2 * | 3/2014 | Li | A61P 19/08 514/588 |
| 8,741,911 | B2 | 6/2014 | Allgeier et al. | |
| 8,921,565 | B2 | 12/2014 | Flynn et al. | |
| 8,940,756 | B2 | 1/2015 | Flynn et al. | |
| 9,012,635 | B2 | 4/2015 | Flynn et al. | |
| 9,133,183 | B2 | 9/2015 | Flynn et al. | |
| 9,181,223 | B2 | 11/2015 | Kaufman et al. | |
| 9,187,474 | B2 | 11/2015 | Flynn et al. | |
| 9,193,719 | B2 | 11/2015 | Flynn et al. | |
| 9,309,224 | B2 | 4/2016 | Flynn et al. | |
| 9,334,267 | B2 | 5/2016 | Flynn et al. | |
| 9,382,228 | B2 | 7/2016 | Flynn et al. | |
| 9,387,202 | B2 | 7/2016 | Flynn et al. | |
| 9,457,019 | B2 | 10/2016 | Flynn et al. | |
| 10,966,966 | B2 | 4/2021 | Soto et al. | |
| 11,103,507 | B2 | 8/2021 | Flynn et al. | |
| RE48,731 | E | 9/2021 | Flynn et al. | |
| 2002/0058678 | A1 | 5/2002 | Cirillo et al. | |
| 2002/0077486 | A1 | 6/2002 | Scarborough et al. | |
| 2002/0165394 | A1 | 11/2002 | Dumas et al. | |
| 2002/0193405 | A1 | 12/2002 | Askew et al. | |
| 2003/0060455 | A1 | 3/2003 | Moss et al. | |
| 2003/0144278 | A1 | 7/2003 | Riedl et al. | |
| 2003/0181442 | A1 | 9/2003 | Riedl et al. | |
| 2003/0216396 | A1 | 11/2003 | Dumas et al. | |
| 2004/0043388 | A1 | 3/2004 | Come et al. | |
| 2004/0067938 | A1 | 4/2004 | Zhang et al. | |
| 2004/0102636 | A1 | 5/2004 | Miller et al. | |
| 2004/0157827 | A1 | 8/2004 | Pevarello et al. | |
| 2004/0167224 | A1 | 8/2004 | Ozaki et al. | |
| 2004/0171075 | A1 | 9/2004 | Flynn et al. | |
| 2004/0180906 | A1 | 9/2004 | Flynn et al. | |
| 2005/0148605 | A1 | 7/2005 | Grotzfeld et al. | |
| 2005/0165024 | A1 | 7/2005 | Milanov et al. | |
| 2005/0165031 | A1 | 7/2005 | Grotzfeld et al. | |
| 2005/0165074 | A1 | 7/2005 | Grotzfeld et al. | |
| 2005/0171171 | A1 | 8/2005 | Mehta et al. | |
| 2005/0171172 | A1 | 8/2005 | Lai et al. | |
| 2005/0192314 | A1 | 9/2005 | Mehta et al. | |
| 2005/0197371 | A1 | 9/2005 | Milanov et al. | |
| 2005/0256174 | A1 | 11/2005 | Wood et al. | |
| 2005/0261315 | A1 | 11/2005 | Mehta et al. | |
| 2005/0267182 | A1 | 12/2005 | Milanov et al. | |
| 2005/0288286 | A1 | 12/2005 | Flynn et al. | |
| 2006/0247186 | A1 | 11/2006 | Carter et al. | |
| 2007/0078121 | A1 | 4/2007 | Flynn et al. | |
| 2007/0179130 | A1 | 8/2007 | Bannen | |
| 2007/0191336 | A1 | 8/2007 | Flynn et al. | |
| 2007/0244120 | A1 | 10/2007 | Dumas et al. | |
| 2008/0009527 | A1 | 1/2008 | Dumas et al. | |
| 2008/0045531 | A1 | 2/2008 | Flynn et al. | |
| 2008/0045706 | A1 | 2/2008 | Flynn et al. | |
| 2008/0090856 | A1 | 4/2008 | Flynn et al. | |
| 2008/0113967 | A1 | 5/2008 | Flynn et al. | |
| 2008/0132506 | A1 | 6/2008 | Flynn et al. | |
| 2008/0187978 | A1 | 8/2008 | Flynn et al. | |
| 2008/0207699 | A1 | 8/2008 | Hoelzemann et al. | |
| 2008/0214545 | A1 | 9/2008 | Lee et al. | |
| 2008/0220497 | A1 | 9/2008 | Flynn et al. | |
| 2008/0221192 | A1 | 9/2008 | Wan et al. | |
| 2008/0248487 | A1 | 10/2008 | Flynn et al. | |
| 2008/0248548 | A1 | 10/2008 | Flynn et al. | |
| 2008/0300281 | A1 | 12/2008 | Dumas et al. | |
| 2009/0069310 | A1 | 3/2009 | Flynn et al. | |
| 2009/0075986 | A1 | 3/2009 | Flynn et al. | |
| 2009/0093526 | A1 | 4/2009 | Miller et al. | |
| 2009/0099190 | A1 | 4/2009 | Flynn et al. | |
| 2009/0105230 | A1 | 4/2009 | Flynn et al. | |
| 2009/0124633 | A1 | 5/2009 | Jonczyk et al. | |
| 2009/0137021 | A1 | 5/2009 | Flynn et al. | |
| 2009/0192307 | A1 | 7/2009 | Michelotti et al. | |
| 2009/0215799 | A1 | 8/2009 | Stieber et al. | |
| 2009/0281089 | A1 | 11/2009 | Gunzner et al. | |
| 2009/0312349 | A1 | 12/2009 | Flynn et al. | |
| 2009/0325945 | A1 | 12/2009 | Niculescu-Duvaz et al. | |
| 2010/0075971 | A1 | 3/2010 | Dumas et al. | |
| 2010/0286215 | A1 | 11/2010 | Pelcman et al. | |
| 2011/0077240 | A1 | 3/2011 | Mannion et al. | |
| 2011/0092461 | A1 | 4/2011 | Gunzner et al. | |
| 2011/0098293 | A1 | 4/2011 | Mannion et al. | |
| 2011/0112193 | A1 | 5/2011 | Nilsson et al. | |
| 2011/0136760 | A1 | 6/2011 | Flynn et al. | |
| 2011/0136809 | A1 | 6/2011 | Lee et al. | |
| 2011/0195110 | A1 | 8/2011 | Smith et al. | |
| 2011/0207752 | A1 | 8/2011 | Geeganage | |
| 2012/0094980 | A1 | 4/2012 | Gunzner et al. | |
| 2012/0114605 | A1 | 5/2012 | Li | |
| 2012/0225057 | A1 | 9/2012 | Flynn et al. | |
| 2012/0270878 | A1 | 10/2012 | Miller et al. | |
| 2013/0071403 | A1 | 3/2013 | Rolland et al. | |
| 2013/0225581 | A1 | 8/2013 | Furuta et al. | |
| 2013/0296326 | A1 | 11/2013 | Pollock | |
| 2014/0179632 | A1 | 6/2014 | Mannion et al. | |
| 2014/0296248 | A1 | 10/2014 | Bernards et al. | |
| 2014/0336210 | A1 | 11/2014 | Carter et al. | |
| 2015/0105550 | A1 | 4/2015 | Gunzner et al. | |
| 2015/0111879 | A1 | 4/2015 | Gunzner et al. | |
| 2015/0133462 | A1 | 5/2015 | Singh et al. | |
| 2015/0218652 | A1 | 8/2015 | Doebele et al. | |
| 2015/0225369 | A1 | 8/2015 | Wucherer-Plietker et al. | |
| 2015/0246033 | A1 | 9/2015 | Flynn et al. | |
| 2015/0275306 | A1 | 10/2015 | Bernards et al. | |
| 2015/0290316 | A1 | 10/2015 | Graziano et al. | |
| 2016/0045532 | A1 | 2/2016 | Roberts et al. | |
| 2016/0152569 | A1 | 6/2016 | Gunzner-Toste et al. | |
| 2016/0289663 | A1 | 10/2016 | Kiyokawa et al. | |
| 2017/0015627 | A1 | 1/2017 | Gunzner-Toste et al. | |
| 2017/0121321 | A1 | 5/2017 | Crews et al. | |
| 2017/0174750 | A1 | 6/2017 | Lim et al. | |
| 2017/0349880 | A1 | 12/2017 | Doucey et al. | |
| 2018/0000771 | A1 | 1/2018 | Inoue et al. | |
| 2018/0015075 | A1 * | 1/2018 | Boscolo | A61K 31/506 |
| 2018/0015175 | A1 * | 1/2018 | Kim | C07K 16/28 |
| 2018/0071302 | A1 | 3/2018 | Abella et al. | |
| 2018/0071303 | A1 | 3/2018 | Abella et al. | |
| 2019/0091217 | A1 | 3/2019 | Flynn et al. | |
| 2020/0129489 | A1 | 4/2020 | Flynn et al. | |
| 2020/0352920 | A1 | 11/2020 | Flynn et al. | |
| 2020/0354346 | A1 | 11/2020 | Flynn et al. | |
| 2020/0354352 | A1 | 11/2020 | Flynn et al. | |
| 2021/0015801 | A1 | 1/2021 | Flynn et al. | |
| 2021/0128556 | A1 | 5/2021 | Flynn et al. | |
| 2021/0145805 | A1 | 5/2021 | Flynn et al. | |
| 2021/0196691 | A1 | 7/2021 | Soto et al. | |
| 2021/0196692 | A1 | 7/2021 | Kaufman et al. | |
| 2021/0196693 | A1 | 7/2021 | Kaufman et al. | |

FOREIGN PATENT DOCUMENTS

| | | | |
|---|---|---|---|
| CN | 108379591 | A | 8/2018 |
| DE | 1115350 | B | 10/1961 |
| DE | 4343831 | A1 | 6/1995 |
| EP | 0021228 | A1 | 1/1981 |
| EP | 0025232 | A1 | 3/1981 |
| EP | 0154190 | A1 | 9/1985 |
| EP | 0661276 | A1 | 7/1995 |
| EP | 0692483 | A1 | 1/1996 |
| EP | 0739884 | A2 | 10/1996 |

(56) References Cited

FOREIGN PATENT DOCUMENTS

| | | | |
|---|---|---|---|
| EP | 0867435 | A1 | 9/1998 |
| EP | 0927555 | A1 | 7/1999 |
| EP | 928790 | A1 | 7/1999 |
| EP | 0956855 | A1 | 11/1999 |
| EP | 1281399 | A2 | 2/2003 |
| FR | 2337554 | A1 | 8/1977 |
| FR | 2396549 | A2 | 2/1979 |
| GB | 971307 | A | 9/1964 |
| GB | 1410279 | A | 10/1975 |
| GB | 2220206 | A | 1/1990 |
| JP | 9-221476 | | 8/1997 |
| JP | 2000275886 | A | 10/2000 |
| JP | 2001-2687 | A | 1/2001 |
| JP | 59-15247 | B2 | 5/2016 |
| WO | WO-1991/19708 | A1 | 12/1991 |
| WO | WO-1992/08693 | A1 | 5/1992 |
| WO | WO-1994/18176 | A1 | 8/1994 |
| WO | WO-1994/21617 | A1 | 9/1994 |
| WO | WO-1994/24095 | A1 | 10/1994 |
| WO | WO-1995/15954 | A1 | 6/1995 |
| WO | WO-1995/29902 | A1 | 11/1995 |
| WO | WO-1995/34540 | A1 | 12/1995 |
| WO | WO-1996/16046 | A2 | 5/1996 |
| WO | WO-1996/19477 | A1 | 6/1996 |
| WO | WO-1997/34900 | A1 | 9/1997 |
| WO | WO-1997/40028 | A1 | 10/1997 |
| WO | WO-1998/22103 | A1 | 5/1998 |
| WO | WO-1998/52558 | A1 | 11/1998 |
| WO | WO-1999/15164 | A1 | 4/1999 |
| WO | WO-1999/23091 | A1 | 5/1999 |
| WO | WO-1999/23093 | A1 | 5/1999 |
| WO | WO-1999/3 7622 | A1 | 7/1999 |
| WO | WO-1999/32106 | A1 | 7/1999 |
| WO | WO-1999/32110 | A1 | 7/1999 |
| WO | WO-1999/32111 | A1 | 7/1999 |
| WO | WO-1999/32455 | A1 | 7/1999 |
| WO | WO-1999/59959 | A1 | 11/1999 |
| WO | WO-2000/06550 | A1 | 2/2000 |
| WO | WO-2000/07980 | A1 | 2/2000 |
| WO | WO-2000/18738 | A1 | 4/2000 |
| WO | WO-2000/21927 | A2 | 4/2000 |
| WO | WO-2000/41698 | A1 | 7/2000 |
| WO | WO-2000/042012 | A1 | 7/2000 |
| WO | WO-2000/43384 | A1 | 7/2000 |
| WO | WO-2000/55139 | A2 | 9/2000 |
| WO | WO-2000/59506 | A1 | 10/2000 |
| WO | WO-2000/071515 | A2 | 11/2000 |
| WO | WO-2001/12621 | A1 | 2/2001 |
| WO | WO-2001/14372 | A2 | 3/2001 |
| WO | WO-2001/74771 | A1 | 10/2001 |
| WO | WO-2001/96298 | A2 | 12/2001 |
| WO | WO-2002/00647 | A1 | 1/2002 |
| WO | WO-2002/14291 | A1 | 2/2002 |
| WO | WO-2002/14311 | A2 | 2/2002 |
| WO | WO-2002/026712 | A2 | 4/2002 |
| WO | WO-2002/28835 | A1 | 4/2002 |
| WO | WO-2002/34 727 | A2 | 5/2002 |
| WO | WO-2002/060869 | A2 | 8/2002 |
| WO | WO-2002/060876 | A1 | 8/2002 |
| WO | WO-2002/062763 | A2 | 8/2002 |
| WO | WO-2002/070662 | A2 | 9/2002 |
| WO | WO-2003/005999 | A2 | 1/2003 |
| WO | WO-2003/047579 | A1 | 6/2003 |
| WO | WO-2003/053368 | A2 | 7/2003 |
| WO | WO-2003/059373 | A2 | 7/2003 |
| WO | WO-2003/068223 | A1 | 8/2003 |
| WO | WO-2003/068229 | A1 | 8/2003 |
| WO | WO-2003/072577 | A1 | 9/2003 |
| WO | WO-2003/084539 | A2 | 10/2003 |
| WO | WO-2004/004720 | A1 | 1/2004 |
| WO | WO-2004/056783 | A1 | 7/2004 |
| WO | WO-2004/060305 | A2 | 7/2004 |
| WO | WO-2004/060306 | A2 | 7/2004 |
| WO | WO-2004/061084 | A2 | 7/2004 |
| WO | WO-2004/078128 | A2 | 9/2004 |
| WO | WO-2004/078746 | A2 | 9/2004 |
| WO | WO-2004/113352 | A1 | 12/2004 |
| WO | WO-2005/002673 | A1 | 1/2005 |
| WO | WO-2005/024755 | A2 | 3/2005 |
| WO | WO-2005/034869 | A2 | 4/2005 |
| WO | WO-2005/048948 | A2 | 6/2005 |
| WO | WO-2005/110994 | A2 | 11/2005 |
| WO | WO-2006/014290 | A2 | 2/2006 |
| WO | WO-2006/014325 | A2 | 2/2006 |
| WO | WO-2006/028958 | A2 | 3/2006 |
| WO | WO-2006/039718 | A2 | 4/2006 |
| WO | WO-2006/040056 | A1 | 4/2006 |
| WO | WO-2006/046552 | A1 | 5/2006 |
| WO | WO-2006/052936 | A2 | 5/2006 |
| WO | WO-2006/062984 | A2 | 6/2006 |
| WO | WO-2006/071940 | A2 | 7/2006 |
| WO | WO-2006/072589 | A2 | 7/2006 |
| WO | WO-2006/081034 | A2 | 8/2006 |
| WO | WO-2006/105844 | A1 | 10/2006 |
| WO | WO-2007/008917 | A2 | 1/2007 |
| WO | WO-2007/064872 | A2 | 6/2007 |
| WO | WO-2007/076473 | A2 | 7/2007 |
| WO | WO-2007/081690 | A2 | 7/2007 |
| WO | WO-2007/115670 | A1 | 10/2007 |
| WO | WO-2007/125330 | A1 | 11/2007 |
| WO | WO-2008/033999 | A2 | 3/2008 |
| WO | WO-2008046003 | A2 * | 4/2008 ............. A61P 43/00 |
| WO | WO-2008/131227 | A1 | 10/2008 |
| WO | WO-2008/131253 | A1 | 10/2008 |
| WO | WO-2008/140895 | A1 | 11/2008 |
| WO | WO-2008/156712 | A1 | 12/2008 |
| WO | WO-2009/030887 | A2 | 3/2009 |
| WO | WO-2009/109035 | A1 | 9/2009 |
| WO | WO-2009/126863 | A2 | 10/2009 |
| WO | WO-2009/127822 | A2 | 10/2009 |
| WO | WO-2009/138758 | A2 | 11/2009 |
| WO | WO-2010/051373 | A1 | 5/2010 |
| WO | WO-2010/124283 | A2 | 10/2010 |
| WO | WO-2011/123788 | A1 | 10/2011 |
| WO | WO-2011/137342 | A1 | 11/2011 |
| WO | WO-2011/139891 | A1 | 11/2011 |
| WO | WO-2011/150198 | A1 | 12/2011 |
| WO | WO-2012/008563 | A1 | 1/2012 |
| WO | WO-2012/019015 | A2 | 2/2012 |
| WO | WO-2012/035131 | A1 | 3/2012 |
| WO | WO-2012/096832 | A2 | 7/2012 |
| WO | WO-2012/097021 | A1 | 7/2012 |
| WO | WO-2012/138783 | A2 | 10/2012 |
| WO | WO-2013/036232 | A2 | 3/2013 |
| WO | WO-2013/043569 | A1 | 3/2013 |
| WO | WO-2013/066440 | A1 | 5/2013 |
| WO | WO-2013/078295 | A2 | 5/2013 |
| WO | WO-2013/134243 | A1 | 9/2013 |
| WO | WO-2013/134252 | A1 | 9/2013 |
| WO | WO-2013/134298 | A1 | 9/2013 |
| WO | WO-2013/177420 | A2 | 11/2013 |
| WO | WO-2013/184119 | A1 | 12/2013 |
| WO | WO-2014/015056 | A2 | 1/2014 |
| WO | WO-2014/032755 | A2 | 3/2014 |
| WO | WO-2014/036387 | A2 | 3/2014 |
| WO | WO-2014/058317 | A1 | 4/2014 |
| WO | WO-2014/071419 | A2 | 5/2014 |
| WO | WO-2014/139458 | A1 | 9/2014 |
| WO | WO-2014/145004 | A1 | 9/2014 |
| WO | WO-2014/145015 | A2 | 9/2014 |
| WO | WO-2014/145023 | A1 | 9/2014 |
| WO | WO-2014/145025 | A2 | 9/2014 |
| WO | WO-2014/145028 | A2 | 9/2014 |
| WO | WO-2014/145029 | A2 | 9/2014 |
| WO | WO-2014/160183 | A1 | 10/2014 |
| WO | WO-2014/182643 | A2 | 11/2014 |
| WO | WO-2015/069217 | A1 | 5/2015 |
| WO | WO-2015/069266 | A1 | 5/2015 |
| WO | WO-2015/076213 | A1 | 5/2015 |
| WO | WO-2015/106292 | A1 | 7/2015 |
| WO | WO-2015/106294 | A1 | 7/2015 |
| WO | WO-2015/148620 | A2 | 10/2015 |
| WO | WO-2015/184443 | A1 | 12/2015 |
| WO | WO-2016/061228 | A1 | 4/2016 |

(56) References Cited

FOREIGN PATENT DOCUMENTS

| | | | | |
|---|---|---|---|---|
| WO | WO-2016/061231 A1 | | 4/2016 | |
| WO | WO-2016/096903 A1 | | 6/2016 | |
| WO | WO-2016/103223 A1 | | 6/2016 | |
| WO | WO-2016/114322 A1 | | 7/2016 | |
| WO | WO-2016/135046 A1 | | 9/2016 | |
| WO | WO-2016187157 A1 | * | 11/2016 | ......... A61K 31/5377 |
| WO | WO-2016/196141 A1 | | 12/2016 | |
| WO | WO-2017/013160 A1 | | 1/2017 | |
| WO | WO-2017/042944 A1 | | 3/2017 | |
| WO | WO-2017/079267 A1 | | 5/2017 | |
| WO | WO-2017/117182 A1 | | 7/2017 | |
| WO | WO-2017/146794 A1 | | 8/2017 | |
| WO | WO-2017/146795 A1 | | 8/2017 | |
| WO | WO-2017/214514 A1 | | 12/2017 | |
| WO | WO-2018/005737 A1 | | 1/2018 | |
| WO | WO-2018/052053 A1 | | 3/2018 | |
| WO | WO-2018/053189 A2 | | 3/2018 | |
| WO | WO-2018/106595 A1 | | 6/2018 | |
| WO | WO-2018/195450 A1 | | 10/2018 | |
| WO | WO-2018/222173 A1 | | 12/2018 | |
| WO | WO-2018/222644 A1 | | 12/2018 | |

OTHER PUBLICATIONS

U.S. Appl. No. 11/870,388, filed Oct. 10, 2007, Granted, U.S. Pat. No. 7,790,756.
U.S. Appl. No. 12/829,561, filed Jul. 2, 2010, Granted, U.S. Pat. No. 8,586,565.
U.S. Appl. No. 11/854,354, filed Sep. 12, 2007, Granted, U.S. Pat. No. 8,188,113.
U.S. Appl. No. 10/746,460, filed Dec. 24, 2003, Granted, U.S. Pat. No. 7,144,911.
U.S. Appl. No. 10/886,329, filed Jul. 6, 2004, Granted, U.S. Pat. No. 7,202,257.
U.S. Appl. No. 11/450,840, filed Jun. 9, 2006, Granted, U.S. Pat. No. 7,342,037.
U.S. Appl. No. 11/336,708, filed Jan. 20, 2006, Granted, U.S. Pat. No. 7,531,566.
U.S. Appl. No. 11/450,850, filed Jun. 9, 2006, Granted, U.S. Pat. No. 7,666,895.
U.S. Appl. No. 10/746,607, filed Dec. 24, 2003, Granted, U.S. Pat. No. 7,279,576.
U.S. Appl. No. 11/854,293, filed Sep. 12, 2007, Granted, U.S. Pat. No. 7,897,762.
U.S. Appl. No. 12/105,408, filed Apr. 18, 2008, Granted, U.S. Pat. No. 8,143,293.
U.S. Appl. No. 13/590,955, filed Aug. 21, 2012, Granted, U.S. Pat. No. 8,486,951.
U.S. Appl. No. 11/450,849, filed Jun. 9, 2006, Granted, U.S. Pat. No. 7,737,283.
U.S. Appl. No. 13/785,575, filed Mar. 5, 2013, Granted, U.S. Pat. No. 8,741,911.
U.S. Appl. No. 12/608,578, filed Oct. 29, 2009, Granted, U.S. Pat. No. 8,278,331.
U.S. Appl. No. 13/098,247, filed Apr. 29, 2011, Granted, U.S. Pat. No. 8,569,319.
U.S. Appl. No. 13/559,170, filed Jul. 26, 2012, Granted, U.S. Pat. No. 8,637,672.
U.S. Appl. No. 14/214,134, filed Mar. 14, 2014, Granted, U.S. Pat. No. 9,133,183.
U.S. Appl. No. 14/383,803, filed Mar. 5, 2013, Granted, U.S. Pat. No. 9,187,474.
U.S. Appl. No. 13/491,394, filed Jun. 7, 2012, Granted, U.S. Pat. No. 8,461,179.
U.S. Appl. No. 13/801,753, filed Mar. 13, 2013, Granted, U.S. Pat. No. 8,940,756.
U.S. Appl. No. 16/387,315, filed Apr. 17, 2019, Granted, Re. 48731.
U.S. Appl. No. 14/214,127, filed Mar. 14, 2014, Granted, U.S. Pat. No. 9,012,635.
U.S. Appl. No. 13/683,277, filed Nov. 21, 2012, Granted, U.S. Pat. No. 8,921,565.
U.S. Appl. No. 14/549,125, filed Nov. 20, 2014, Granted, U.S. Pat. No. 9,387,202.
U.S. Appl. No. 14/214,160, filed Mar. 14, 2014, Granted, U.S. Pat. No. 9,193,719.
U.S. Appl. No. 14/214,171, filed Mar. 14, 2014, Granted, U.S. Pat. No. 9,181,223.
U.S. Appl. No. 14/214,185, filed Mar. 14, 2014, Granted, U.S. Pat. No. 9,382,228.
U.S. Appl. No. 14/214,179, filed Mar. 14, 2014, Granted, U.S. Pat. No. 9,309,224.
U.S. Appl. No. 14/383,799, filed Mar. 5, 2013, Granted, U.S. Pat. No. 9,334,267.
U.S. Appl. No. 14/535,900, filed Nov. 7, 2014, Granted, U.S. Pat. No. 9,457,019.
U.S. Appl. No. 17/374,446, filed Jul. 13, 2021, Pending.
U.S. Appl. No. 16/617,721, filed Nov. 27, 2019, Published, US 2020-0129489 A1.
U.S. Appl. No. 17/028,591, filed Sep. 22, 2020, Published, US 2021-0015801 A1.
U.S. Appl. No. 17/506,772, filed Oct. 21, 2021, Published, US 2022-0031678 A1.
U.S. Appl. No. 16/943,821, filed Jul. 30, 2020, Published, US 2021-0145805 A1.
U.S. Appl. No. 16/943,871, filed Jul. 30, 2020, Published, US 2020-0352920 A1.
U.S. Appl. No. 16/725,282, filed Dec. 23, 2019, Granted, U.S. Pat. No. 11,103,507.
U.S. Appl. No. 17/358,137, filed Jun. 25, 2021, Pending.
U.S. Appl. No. 16/870,384, filed May 8, 2020, Published, US 2020-0354352 A1.
U.S. Appl. No. 16/870,418, filed May 8, 2020, Published, US 2020-0354346 A1.
U.S. Appl. No. 16/902,989, filed Jun. 16, 2020, Pending, US 2021-0128556 A1.
U.S. Appl. No. 17/180,234, filed Feb. 19, 2021, Granted, U.S. Pat. No. 11,185,535.
U.S. Appl. No. 17/504,133, filed Oct. 18, 2021, Published, US 2022-0031677 A1.
U.S. Appl. No. 17/028,640, filed Sep. 22, 2020, Granted, U.S. Pat. No. 10,966,966.
U.S. Appl. No. 17/180,218, filed Feb. 19, 2021, Published, US 2021-0196691 A1.
U.S. Appl. No. 17/583,977, filed Jan. 25, 2022, Pending.
U.S. Appl. No. 17/583,985, filed Jan. 25, 2022, Pending.
U.S. Appl. No. 17/180,241, filed Feb. 19, 2021, Published, US 2021-0196693 A1.
U.S. Appl. No. 17/193,707, filed Mar. 5, 2021, Published, US 2021-0275518 A1.
U.S. Appl. No. 17/528,478, filed Nov. 17, 2021, Pending.
U.S. Appl. No. 17/534,795, filed Nov. 24, 2021, Pending.
U.S. Appl. No. 17/534,762, filed Nov. 24, 2021, Pending.
U.S. Appl. No. 17/534,764, filed Nov. 24, 2021, Pending.
U.S. Appl. No. 17/534,768, filed Nov. 24, 2021, Pending.
U.S. Appl. No. 17/534,769, filed Nov. 24, 2021, Pending.
U.S. Appl. No. 17/534,771, filed Nov. 24, 2021, Pending.
"Additions and Corrections", Journal of Medicinal Chemistry, 32(12):2583 (1989).
"NHLBI LBC Computational Biophysics Section", CHARMM Documentation Index, <http://www.lobos.nih.gov/Charmm/chmdoc.html, >printed Mar. 4, 2005 (1 page).
"Trilateral Project WM4—Comparative Studies in New Technologies: Report on Comparative Study on Protein 3-Dimensional Structure Related Claims—ANNEX 3: Comments of the USPTO", Vienna, Austria, Nov. 4-8, pp. 58-79 (2002).
Ahmad et al., "Differential Expression of Angiopoietin-1 and Angiopoietin-2 in Colon Carcinoma" Cancer (2001) 92: 1138-1143.
Aklilu, et al., "Increased PTHRP Production by a Tyrosine Kinase Oncogene, Tpr-Met: Rose of the Ras Signaling Pathway", The American Physiological Society, pp. E277-E283 (1996).
Albericio, et al., "Synthesis of a Sulfaydantion Library", J. Comb. Chem., 3:290-300 (2001).

(56) References Cited

OTHER PUBLICATIONS

Almerico, et al., "On the Preparation of 1-aryl-2-heteroaryl- and 2-aryl-1-heteroaryl-pyrroles as Useful Building Blocks for Biologically Interesting Heterocycles", ARKIVOC, Rudy Abramovitch Issue, pp. 129-142 (2001).
Anzai, et al., "Alkyl- and Arylthiation of Uracil and Indole", J. Heterocyclic Chem., 16:567-569 (1979).
Askew, et al., "Molecular Recognition with Convergent Functional Groups: 6. Synthetic and Structural Studies with a Model Receptor for Nucleic Acid Components", J. Am. Chem., 111:1082-1090 (1989).
Avruch, J. et al., "Ras Activation of the Raf Kinase: Tyrosine Kinase Recmitment of the MAP Kinase Cascade," Recent Prag Harm. Res. (2001) 56: 127-155.
Bais, et al., "Inhibition of Endogenous Wxalate Production: Biochemical Consideration of the Roles of Glycollate Oxidase and Lactate Dehydrogenase", Clinical Science, 76:303-309 (1989).
Baker, et al., "Irreversible Enzyme Inhibitors. 188. Inhibition of Mammalian Thymidine Phosphorylase", Journal of Medicinal Chemistry, 14:612-616 (1971).
Balmana, J. et al., "BRCA in breast cancer:ESMO clinical recommendations", Ann Oncol 2009; 20(supp 4):iv19-20.
Barker, et al., "Characterization of pp60c-src Tyrosine Kinase Activities Using a Continuous Assay: Autoactivation of the Enzyme is an Intermolecular Autophosphorylation Process", Biochemistry, 35:14843-14851 (1995).
Barvian, et al., "Pyrido[2,3-d]pyrimidin-7-one Inhibitors of Cyclin-Dependent Kinases," J Med Chem. (2000) 43: 4606-4616.
Bausch, et al., "Proton-Transfer Chemistry of Urazoles and Related Imides, and Diacyl Hydrazides", J. Org. Chem., 56:5643-5651 (1991).
Benvenuti, et al., "Crystallization of Soluble Proteins in Vapor Diffusion for X-Ray Crystallography", Nature Protocols, 2(7):1633-1651 (2007).
Bolton, et al., "Chapter 17. Ras Oncogene Directed Approaches in Cancer Chemotherapy," Ann. Rep. Med. Chem. (1994) 29: 165-174.
Bosca, et al., "Circular Dichroism Analysis of Ligand-Induced Conformational Changes in Protein Kinase C", Biochem. J., 290:827-832 (1993).
Boschelli, et al., "4-Anilino-3-quinolinecarbonitriles: An Emerging Class of Kinase Inhibitors", Current Topics in Medicinal Chemistry, 2:1051-1063 (2002).
Bourdonnec, et al., "Synthesis and Pharmacological Evaluation of New Pyrazolidine-3,5-diones as AT1 Angiotensin II Receptor Antagonists", J. Med. Chem., 43:2685-2697 (2000).
Boyer, "Small Molecule Inhibitors of KDR (VEGFR-2) Kinase: An Overview of Structure Activity Relationships", Current Topics in Medicinal Chemistry, 2:973-1000 (2002).
Brady, et al., "Fast Prediction and Visualization of Protein Binding Pockets with PASS". Journal of Computer-Aided Molecular Design, 14:383-401 (2000).
Branford et al., "High frequency of point mutations clustered within the adenosine triphosphate-binding region of BCR/ABL in patients with chronic myeloid leukemia or Ph-positive acute lymphoblastic leukemia who develope imatinib (ST1571)resistance," *Blood* (2002) vol. 99, pp. 3472-3475.
Brasher, et al., "C-Abl has High Intrinsic Tyrosine Kinase Activity that is Stimulated by Mutation of the Src Homology 3 Domain and by Autophosphorylation at Two Distinct Regulatory Tyrosines", Journal of Biological Chemistry, 275:35631-35637 (2000).
Brunckhorst et al., "Angiopoietin-4 Promotes Glioblastoma Progression by Enhancing Tumor Cell Viability and Angiogenesis" Cancer Research (2010) 70:7283-7293.
Bullock, et al., "Prospects for Kinase Activity Modulators in the Treatment of Diabetes and Diabetic Complications", Current Topics in Medicinal Chemistry, 2:915-938 (2002).
Byron, et al., "The Synthesis of some Substituted Biphenyl-4-carboxylic Acids, 4-Biphenylylacetic Acids, and 4-Aminobiphenyls", J. Chem. Soc. (C), Organic, pp. 840-845 (1966).
Cardillo, et al., "Sulle 1,2-difenil-3.5-dichetopirazolidine", Gazz. Chim., Ital., 9:973-985 (1966)—Italian Language.
Carr, J.B. et al., "Isoxazole Anthelmintics," *J. Med. Chem* (1977) vol. 20, No. 7, pp. 934-939.
Chan et al., "Copper promoted C—N and C—O bond cross-coupling with phenyl and pyridylboronates," *Tetrahedron Letters* (2003) vol. 44, pp. 3863-3865.
Chan, "Promotion of Reaction of N—H Bonds with Triarylbismuth and Cupric Acetate," *Tetrahedron Letters* (1996) vol. 37, No. 50, pp. 9013-9016.
Chan, et al., "New N- and O-Arylations with Phenylboronic Acids and Cupric Acetate," Tetrahedron Lett. (1998) 39: 2933-2936.
Chan, et al., "Conformational Control Inhibition of the BCR-ABL1 Tyrosine Kinase, Including the Gatekeeper T3151 Mutant, by the Switch-Control Inhibitor DCC-2036," Cancer Cell (Apr. 12, 2011) pp. 556-568.
Chen, et al., "Biochemical Evidence for the Autophosphorylation and Transphosphorylation of Transforming Growth Factor ? Receptor Kinases", Proc. Natl. Acad. Sci. USA, 92:1565-1569 (1995).
Cheng, et al., "Novel Solution Phase Strategy for the Synthesis of Chemical Libraries Containing Small Organic Molecules", J. Am. Chem. Soc., 118:2567-2573 (1996).
Cheng, et al., "Synthesis and SAR of Heteroaryl-phenyl-substituted Pyrazole Derivatives as Highly Selective and Potent Canine COX-2 Inhibitors", Bioorganic & Medicinal Chemistry Letters, 16:2076-2080 (2006).
Chu, et al., "Using Affinity Capillary Electrophoresis to Determine Binding Stoichiometries of Protein-Ligand Interactions", Biochemistry, 33:10616-10621 (1994).
Cirillo, et al. "The Non-Diaryl Heterocycle Classes of p38 MAP Kinase Inhibitors", Current Topics in Medicinal Chemistry, 2:1021-1035 (2002).
Closier, et al., "Nitrofuryl Heterocyclics. 1", Journal of Medicinal Chemistry, 13(4):638-640 (1970).
Cockerill, et al., "Small Molecule Inhibitors of the Class 1 Receptor Tyrosine Kinase Family", Current Topics in Medicinal Chemistry, 2:1001-1010 (2002).
Colton, et al., "Affinity Capillary Electrophoresis: A Physical-Organic Tool for Studying Interactions in Biomolecular Recognition", Electrophoresis, 19:367-382 (1998).
Cortes, et al., "Results of Imatinib Mesylate Therapy in Patients with Refractory or Recurrent Acute Myeloid Leukemia, High-Risk Myelodysplastic Syndrime, and Myeloproliferative Disorders", Cancer, 97(11):2760-2766 (2003).
Cortes, Javier, et al., "Eribulin Monotherapy Versus Treatment of Physician's Choice in Patients With Metastatic Breast Cancer (EMBRACE): A Phase 3 Open-label Randomised Study", The Lancet, vol. 377, No. 9769, Mar. 1, 2011 (Mar. 1, 2011), pp. 914-923, ISSN: 0140-6736, DOI: 10.1016/S0140-6736(11 )60070-6.
Cross, et al., "Inhibition of Glycogen Synthase Kinase-3 by Insulin Mediated by Protein Kinase B", Nature, 378:785-789 (1995).
Cudney, "Preface: Protein Crystallization and Dumb Luck", The Rigaku Journal, 16(1):1-7 (1999).
Dajani, et al., "Crystal Structure of Glycogen Synthase Kinas 3(3: Structural Basis for Phosphate-Primed Substrate Specificity and Autoinhibition", Cell, 105:721-732 (2001).
Dajani, et al., "Structural Basis for Recruitment of Glycogen Synthase Kinase 313 to the Axin-APC Scaffold Complex", EMBO, 22(3):494-501 (2003).
Daley et al., "Induction of Chronic Myelogenous Leukemia in Mice by the P210bcr/abl Gene of the Philadelphia Chromosome," Science (Feb. 16, 1990) vol. 247, pp. 824-830.
Davies, H. et al, "Mutations of the BRAF gene in human cancer," Nature (Jun. 2002) 41 7: 949-954.
Davis, et al., "Iterative Size-Exclusion Chromatography Coupled with Liquid Chromatographic Mass Spectrometry to Enrich and Identify Tight-Binding Ligands from Complex Mixtures", Tetrahedron, 55:11653-11667 (1999).
De Boer, et al., "Synthesis and Characterization of Conjugated Mono- and Dithiol Oligomers and Characterization of Their Self-Assembled Monolayers", Langmuir, 19:4272-4284 (2003).

(56) References Cited

OTHER PUBLICATIONS

De Silva, et al., "Gastrointestinal Stromal Tumors (GIST): C-kin Mutations, CD117 Expression, Differential Diagnosis and Targeted Cancer Therapy with Imatinib", Pathology Oncology Research, 9(1):13-19 (2003).
Deng, et al., "Expression, Characterization, and Crystallization of the Pyrophosphate-Dependent Phosphofructo-1-Kinase of Borrelia Burgdorferi", Archives of Biochemistry and Biophysics, 371(2):326-331 (1999).
Dess, et al., "A Useful 12-1-5 Triacetoxyperiodiane (the Dess-Martin Periodiane) for Selective Oxidation of Primary or Secondary Alcohols and a Variety of Related 12-1-5 Species", J. Am. Chem., Soc., 113:7277-7287 (1991).
Dong, J., Overcoming Resistance to BRAF and MEK inhibitors by Simultaneous Suppression of CDK4. InTech. Jan. 30, 2013. Melanoma—From Early Detection to Treatment, Chapter 1; abstract; p. 7, second paragraph; p. 9, figure 4; DOI: 10.5772/53620.
Dumas et al., "Recent developments in the discovery of protein kinase inhibitors from the urea class," *Current Opinion in Drug Discovery & Development* (2004) vol. 7, No. 5, pp. 600-616.
Dumas, "Preface", Current Topics in Medicinal Chemistry (2002) (1 Page).
Dumas, "Protein Kinase Inhibitors: Emerging Pharmacophores", Exp. Opin. Ther. Patent, 11:405-429 (2001).
Dumas, et al., "Discovery of a New Class of p38 Kinase Inhibitors", Bioorganic & Medicinal Chemistry Letters, 10:2047-2050 (2000).
Eide, et al., "The ABL Switch Control Inhibitor DCC-2036 is Active against the Chronic Myeloid Leukemia Mutant BCR-ABLT3151 and Exhibits a Narrow Resistance Profile," American Association for Cancer Research (Apr. 19, 2011) pp. 3189-3195.
Ettmayer et al., "Lessons Learned from Marketed and Investigational Prodrugs," *Journal of Medicinal Chemistry* (May 6, 2004) vol. 47, No. 10, pp. 2393-2404.
Ewing, "Critical Evaluation of Search Algorithms for Automated Molecular Docking and Database Screening", Journal of Computational Chemistry, 18(9):1175-1189 (1997).
Faderl et al., "The Biology of Chronic Myeloid Leukemia," *The New England Journal of Medicine* (Jul. 15. 1999) vol. 341. No. 3. pp. 164-172.
Farooqui, et al., "Interactions Between Neural Membrane Glycerophospholipid and Sphingolipid Mediators: A Recipe for Neural Cell Survival or Suicide", Journal of Neuroscience Research, 85:1834-1850 (2007).
Fathalla, "Synthesis of New Pyrazolo[1,5-a]pyrimidine Derivative Using 5-Aminouracil and Ketene Dithiacetal", Arch Pharm Res, 22(6):571-574 (1999).
Fathalla, et al., "Synthesis of New Uracil-5-Sulfonamide Derivatives and Immuno-Stimulatory Effect of a Chemically Modified Hemolymph of Biomphalaria Alexandrina on Schistosoma Manosi Infected Mice", Arch Pharm Res., 26(5):358-366 (2003).
Fathalla, et al., "Synthesis of New Uracil-5-Sulphonamide-p-Phenyl Derivatives and Their Effect on *Biomphalaria alexandrina* Snail's Nucleoproteins", Arch. Pharm. Res., 23(2):128-138 (2000).
Flatt, et al., "Synthesis of Thiol Substituted Oligoanilines for Molecular Device Candidates", Tetrahedron Letters, 44:6699-6702 (2003).
Fletcher, et al., "Diagnosis of Gastrointestinal Stromal Tumors: A Consensus Approach", 33(5):459-465 (2002).
Frame, et al., "A Common Phosphate Binding Site Explains the Unique Substrate Specificity of GSK3 and Its Inactivation by Phosphorylation", Molecular Cell, 7:1321-1327 (2001).
Furyua, et al., "Addition of 4-Ethoxyimidazoles to Dimethyl Acetylenedicarboxylate and Transformation of the Adducts to Pyrimidian-5-yl Acetates", Chem. Pharm. Bull., 36(5):1669-1675 (1988).
Garcia-Tellado, et al., "Molecular Recognition in the Solid Waste State: Controlled Assembly of Hydrogen-Bonded Molecular Sheets", J. Am. Chem. Soc., 113:9265-9269 (1991).
Gillen, J. et al., "Angiopoietin-1 and Angiopoietin-2 inhibitors: Clinical Development", Current Oncology Reports (Feb. 2019)21:22, 7 pages.
Gishizky et al., "Efficient transplantation of BCR-ABL-induced chronic myelogenous leukemia-like syndrome in mice," *Proc. Natl. Acad. Sci.* (Apr. 1993) vol. 90, pp. 3155-3759.
Gorre et al, "Clinical Resistance to STI-571Cancer Therapy Caused by BCR-ABL Gene Mutation or Amplification," Science (Aug. 3, 2001) vol. 293, pp. 876-880.
Greene, et al., "Chapter 7: Protection for the Amino Group", in Protective Groups in Organic Synthesis, Third Edition, pp. 494-653 (1999).
Griffith, et al., "TPAP: Tetra-n-propylammonium Perruthenate, A Mild and Convenient Oxidant for Alcohols", Aldrichimica Acta, 23(1):13-19 (1990).
Guzel, "Investigation of the Relationship Between the Inhibitory Activity of Glycolic Acid Oxidase (GAO) and its Chemical Structure: Electron-Topological Approach", Journal of Molecular Structure, 366:131-137 (1996).
Haar, et al., "Structure of GSK3β Reveals a Primed Phosphorylation Mechanism", Nature Structural Biology, 8(7):593-596 (2001).
Hackler et al., "The Syntheses of 5-Amino-3-t-butylisothiazole and 3-Amino-5-t-butylisothiazole," *J. Heterocyclic Chem.* (Nov.-Dec. 1989) vol. 26, pp. 1575-1578.
Haesslein, et al., "Recent Advances in Cyclin-Dependent Kinase Inhibition. Purine-Based Derivatives as Anti-Cancer Agents. Roles and Perspectives for the Future", Current Topics in Medicinal Chemistry, 2:1037-1050 (2002).
Harney, et al., "The Selective Tie2 Inhibitor Rebastinib Blocks Recruitment and Function of Tie2 Macrophages in Breast Cancer and Pancreatic Neuroendocrine Tumors", Molecular Cancer Therapeutics, 16(11): 2486-2501 (2017).
Hashizume et al., "Complementary Actions of Inhibitors of Angiopoietin-2 and VEGF on Tumor Angiogenesis and Growth" Cancer Research (2010) 70:2213-2223.
Heegaard, et al., "Affinity Capillary Electrophoresis: Important Application Areas and Some Recent Developments", Journal of Chromatography B, 715:29-54 (1998).
Helfrich et al., "Angiopoietin-2 Levels are Associated With Disease Progressino in Metastatic Malignant Melanoma" Clin Cancer Res (2009) 15: 1384-1392.
Honda, et al., "Determination of the Association Constant of Monovalent Mode Protein-Sugar Interaction by Capillary Zone Electrophoresis", Journal of Chromatography, 597:377-382 (1992).
Hou et al., "Expression of Angiopoietins and Vascular Endothelial Growth Factors and Their Clinical Significance in Acute Myeloid Leukemia" *Leukemia Research* (2008) 32:904-912.
Hu, et al., "Capillary Electrophoresis for the Analysis of Biopolymers", Anal., Chem., 74:2833-2850 (2002).
Huang, et al., "Inhibition of Nucleoside Transport by Protein Kinase Inhibitors", The Journal of Pharmacology and Experimental Therapeutics, 304(2):753-760 (2003).
Hubbard, "Crystal Structure of the Activated Insulin Receptor Tyrosine Kinase in Complex with Peptide Substrate and ATP Analog", EMBO, 16(18):5573-5581 (1997).
Hubbard, et al., "Crystal Structure of the Tyrosine Kinase Domain of the Human Insulin Receptor", Nature, 374:746-754 (1994).
Hughes, et al., "Modulation of the Glycogen Synthase Kinase-3 Family by Tyrosine Phosphorylation", EMBO, 12(2):803-808 (1993).
Huse et al, "The Conformational Plasticity of Protein Kinases," *Cell* (May 3, 2002) vol. 109, pp. 275-282.
Huse, et al., "Crystal Structure of the Cytoplasmic Domain of the Type I TGF? Receptor in Complex with FKBP12", Cell, 96:425-436 (1999).
Huse, et al., "The TGFβ Receptor Activation Process: An Inhibitor-to Substrate-Binding Switch", Molecular Cell, 8:671-682 (2001).
Igarashi, et al., "Antimicrobial Activities of 2-arylthio-N-alkylmaleimides", Journal of Industrial Microbiology, 9:91-96 (1992).
International Human Genome Sequencing Consortium, "Initial Sequencing and Analysis of the Human Genome", Nature, 409:860-921 (2001).
International Search Report and Writ Op issued for PCT/US2020/045875 malied Dec. 9, 2020 (13 pages).
International Search Report and Writ Op issued for PCT/US2013/069005 malied Jan. 31, 2014 (45 pages).

(56) References Cited

OTHER PUBLICATIONS

International Search Report and Writ Op issued for PCT/US2021/021069 malied Jun. 6, 2021 (13 pages).
International Search Report issued for PCT/US2008/060833 mailed Sep. 30, 2008 (5 pages).
International Search Report issued for PCT/US2008/060867, mailed Sep. 29, 2008 (5 pages).
International Search Report issued for PCT/US2008/060896, mailed Sep. 29, 2008 (5 pages).
Ishida, et al., "Molecular Arrangement and Electrical Conduction of Self-Assembled Monolayers Made from Terphenyl Thiols", Surface Sciences, 514:187-193 (2002).
Islip, et al., "Nitrofuryl Heterocyclics 3", Journal of Medicinal Chemistry, 16(11):1309-1310 (1973).
Jackson, et al., "N-Terminal Mutations Activate the Leukemogenic Potential of the Myristoylated form of c-abl", EMBO, 8(2):449-456 (1989).
Jackson, et al., "Pyridinylimidazole Based p38 MAP Kinase Inhibitors", Current Topics in Medicinal Chemistry, 2:1011-1020 (2002).
Janku, F. et al., "An open-label, multicenter, phase 1b/2 study of rebastinid in combination with pactlitaxel in a dose expansion cohort to assess safety and preliminary efficacy in patients with advanced or metastic endometrial cancer", May 31, 2020, 1 page, retrieved from internet: https://meetings.asco.org/abstracts-presentations/197661.
Jiang, et al., ""Soft Docking": Matching of Molecular Surface Cubes", J. Mol. Biol., 219:79-102 (1991).
Jiang, et al., "Synthesis and SAR Investigations for Novel Melanin-Concentrating Hormone 1 Receptor (MCH1) Antagonists Part 1. The Discovery of Arylacetamides as Viable Replacements for the Dihydropyrimidione Moiety of an HTS Hit", J. Med. Chem., 50:3870-3882 (2007).
Johnson, "Circular Dichroism Spectroscopy and the Vacuum Ultraviolet Region", Ann. Rev. Phys. Chem., 29:93-114 (1978).
Johnson, "Protein Secondary Structure and Circular Dichroism: A Practical Guide", PROTEINS: Structure, Function, and Genetics, 7:205-214 (1990).
Johnson, et al., "An Evaluation of the Effect of Light Stabilizers on the Exterior Durability of Polyester Powder Coatings for the Architectural Market", Surface Coatings International, 3:134-141 (1999).
Johnson, et al., "The Stereochemistry of Oxidation at Sulfur Oxidation of 2-Thiabicyclo[2.2.1]Hpetane", Tetrahedron, 25:5649-5653 (1969).
Jordan, V. C., Nature Reviews: Drug Discovery, 2, 2003, 205.
Karagiannis, et al., "Neoadjuvant Chemotherapy Induces Breast Cancer Metastasis Through a TMEM-Mediated Mechanism", Science Translational Medicine, 9: 1-15 (2017).
Karlan et al, "Randomized, Double-Blind, Placebo-Controlled Phase II Study of AMG 386 Combined With Weekly Paclitaxel in Patients With Recurrent Ovarian Cancer" J. Clinical Oncology (2012) 30: 362-370.
Kataja et al., Ann Oncol 2009; 20(sup 4): iv10-14.
Katritzky, et al., "Novel Chromophoric Heterocycles Based on Maleimide and Naphthoquinone", J. Heterocyclic Chem., 26:885-892 (1989).
Kern, et al., "Synthese von Makromolekeln einheitlicher Broβe. II Mitt: Syntheses neuer Diol-oligo-urethane nach dem Duplikationsverfahren", Makromolekulara Chemie, 16:89-107 (1955)—English Summary (20 pages).
Kim, et al., "Solid Phase Synthesis of Benzamidine and Butylamine-Derived Hydantoin Libraries", Molecular Diversity, 3:129-132 (1998).
Klayman, et al., "The Reaction of S-Methiodide Derivatives of Activated Thioureas with Hydroxylic Compounds. A Novel Synthesis of Mercaptans", J. Org. Chem., 37(10):1532-1537 (1972).
Kleywegt, et al., "Detection, Delineation, Measurement and Display of Cavities in Macromolecular Structures", Acta Cryst, D50:178-185 (1994).
Koch, et al., "QSAR and Molecular Modelling for a Series of Isomeric X-Sulfanilamido-1-phenylpyrazoles", Quant. Struct. Act. Relat., 12:373-382 (1993).
Kolch, W., "Meaningful relationships: the regulation of the Ras/Raf/MEKJERK pathway by protein interactions," Biochern. J (2000) 351: 289-305.
Konopka et al., "Cell lines and clinical isolates derived from Ph1-positive chronic myelogenous leukemia patients express *c-abl* proteins with a common structural alteration," *Proc. Natl. Acad. Sci.* (Mar. 1985) vol. 82, pp. 1810-1814.
Krasovitskii, et al., "Synthesis and Spectral-Luminescence Properties of Hetarylethylene Derivatives of 2,5-Diphenyloxazole and 2,5-Diphenyl-1,3,4-0xadiazole", Khimiya Geterotsiklicheskikh Soedinenii, 5:617-621 (1982)—English Translation (10 pages).
Kuhn, et al., "The Genesis of High-Throughput Structure-Based Drug Discovery using Protein Crystallography", Analytical Techniques, Current Opinion in Chemical Biology, 6:704-710 (2002).
Kumar, et al., "P38 Map Kinases: Key Signalling Molecules as Therapeutic Targets for Inflammatory Diseases", Nature Reviews Drug Discovery, 2:717-726 (2003).
Kundrot, "Which Strategy for a Protein Crystallization Project", CMLS, Cell. Mol. Life Sci., 61:525-536 (2004).
Kundu, et al., "Depropargylation Under Palladium-Copper Catatlysis: Synthesis of Diaryl Sulfides", Tetrahedron, 57:5885-5895 (2001).
Kurogi, et al., "Discovery of Novel Mesangial Cell Proliferation Inhibitors Using a Three-Dimensional Database Searching Method", J. Med. Chem., 44:2304-2307 (2001).
Kuse, et al., Synthesis of azide-fluoro-dehydrocoelentcrazine analog as a photoaffinitylabeling probe and photolysis of azide-fluoro-coelenterazine; Tetrahedron Lett. (2005) 61: 5754-5762.
Kwong, et al., "A General, Efficient, and Inexpensive Catalyst System for the Coupling Aryl Iodides and Thiols", Organic Letters, 4(20):3517-3520 (2002).
Laskowski, "SURFNET: A Program for Visualizing Molecular Surfaces, Cavities, and Intermolecular Interactions", Journal of Molecular Graphics, 13:323-330 (1995).
Leca, et al., "A New Practical One-Pot Access to Sulfonimidates", Organic Letters, 4(23):4093-4095 (2002).
Lefevre, et al., "Roles of Stem Cell Factor/c-Kit and Effects of Glivec®/STI571 in Human Uveal Melanoma Cell Turmorigenesis", Journal of Biological Chemistry, 279(30):31769-31779 (2004).
Lesort, et al., "Insulin Transiently Increases Tau Phosphorylation: Involvement of Glycogen Synthase Kinase-313 and Fyn Tyrosine Kinase", Journal of Neurochemistry, 72(2):576-584 (1999).
Leung, et al., "The Difluoromethylensulfonic Acid Groups as a Monoanionic Phosphate Surrogate for Obtaining PTP1B Inhibitors", Bioorganic & Medicinal Chemistry, 10:2309-2323 (2002).
Li et al., "The P190, P210, and P230 Forms of the BCR/ABLOncogene induce a Similar Chronic Myeloid Leukemia-like Syndrome in Mice but Have Different Lymphoid Leukemogenic Activity," *J. Exp. Med.* (1999) vol. 189, No. 9, pp. 1399 1412.
Li, et al., "Targeting Serine/Threonine Protein Kinase B/Akt and Cell-cycle Checkpoint Kinases for Treating Cancer", Current Topics in Medicinal Chemistry, 2:939-971 (2002).
Li, et al., "The P190, {210, and P230 Forms of the BCR/ABL Oncogene Induce a Similar Chronic Myeloid Leukemia-like Syndrome in Mice but Have Different Lymphoid Leukemogenic Activity", J. Exp. Med., 189(9):1399-1412 (1999).
Link, et al., "Synthesis of 8-Substituted 5-Deazaflavins", J. Heterocyclic Chem, 22:841-848 (1985).
Lipinski, et al., "Experimental and Computational Approaches to Estimate Solubility and Permeability in Drug Discovery and Development Settings", Advanced Drug Delivery Reviews, 23:3-25 (1997).
Liu et al, "TIE2/TEK Modulates the Interaction of Glioma and Brain Tumor Stem Cells With Endothelial Cells and Promotes an Invasive Phenotype" Oncotarget (2010) 1: 700-709.
Loren, et al., "NH-1,2,3-Triazoles from Azidomethyl Pivalate and Carbamates: Base-Labile N-Protecting Groups", SYNLETT, 18:2847-2850 (2005).
Lorenzi et al., "Amino Acid Ester Prodrugs of 2-Bromo-5, 6-dichloro-1-(β-D-ribofuranosyl)benzimidazole Enhance Metabolic Stability In Vitro and In Vivo," *The Journal of Pharmacology and Experimental Therapeutics* (2005) vol. 314, No. 2, pp. 883-890.
Lowinger et al., "Design and Discovery of Small Molecules Targeting Raf-1 Kinase," *Current Pharmaceutical Design* (2002) vol. 8, No. 25, pp. 2269-2278.

(56) References Cited

OTHER PUBLICATIONS

Ma, et al., "c-MET Mutational Analysis in Small Cell Lung Cancer: Novel Juxtamembrane Domain Mutations Regulating Cytoskeletal Functions", Cancer Research, 63:6272-6281 (2003).
Ma, et al., "c-Met: Structure, Functions and Potential for Therapeutic Inhibition", Cancer and Metastasis Reviews, 22:309-325 (2003).
Magnuson, et al, "The Raf-I serine/threonine protein kinase," Seminars in Cancer Biology. (1994) 5: 247-253.
Mallakpour, et al., "Uncatalyzed Polymerization of Bistriazolinediones with Electron-Rich Aromatic Compounds via Electrophilic Aromatic Substitution", Journal of Polymer Science: Part A: Polymer Chemistry, 27:217-235 (1989).
Mamaev, et al., "Synthesis of 2,5'-Bipyrimidines from Substituted 5-Cyanopyrimidines", Khimiya Geterotsiklicheskikh Soedinenni, 24(3):371-375—(1988)—English Translation.
March's Advanced Organic Chemistry: Reactions, Mechanisms, and Structure, Fifth Edition, Smith and March Editors, Wiley-Interscience Publication (2001) (4 pages).
March, et al., "Tautomerism", from March's Advanced Organic Chemisto.::, 4th Edition, WileyInterscience, pp. 69-74.
Martin, V. et al., "Tie2: a journey from normal angiogenesis to cancer and beyond", Histology and histopathology, Jun. 1, 2008, pp. 773-780.
Martinez, et al., "First Non-ATP Competitive Glycogen Synthase Kinase 3β (GSK-3β) Inhibitors: Thiadizolidinones (TDZD) as Potential Drugs for the Treatment of Alzheimer's Disease", J. Med. Chem., 45(2002)1292-1299 (2002).
Matsubara et al,"TIE2-Expressing Monocytes as a Diagnostic Marker for Hepatocellular Carcinoma Correlates With Angiogenesis" Hepatology (2013) 57: 1416-1425.
Mattsson, et al., "Six X-Linked Agammaglobulinemia-Causing Missense Mutations in the Src Homology 2 Domain of Bruton's Tyrosine Kinase: Phosphotyrosine-Binding and Circular Dichroism Analysis", Journal of Immunology, pp. 4170-4177 (2000).
Mazzieri, R et al., Targeting the ANG2/TIE2 Axis Inhibits Tumor Growth and Metastasis by impairing Angiogenesis and Disabling Rebounds of Proangiogenic Myelid Cells. Cell. Apr. 12, 2001, vol. 19, pp. 512-526; DOI: 10.1016/j.ccr.2001.02.005.
Mcpherson, "Current Approaches to Macromolecular Crystallization", Eur. J. Biochem., 189:1-23 (1990).
Medebielle, et al., "A Convenient Synthesis of Perfluoroalkylated and Fluorinated-Aryl Nitrogen Bases by Electrochemically Induced SRN1 Substitution", J. Org. Chem., 61:1331-1340 (1996).
Medebielle, et al., "A New Convenient Synthesis of 5-Aryl Uracils Using SRN1 Aromatic Nucleophilic Substitution", Tetrahedron Letters, 34(21):3409-3412 (1993).
Mikhaleva, et al., "Relative Reactivities of the Chlorine Atoms of 2,2',4-Trichloro-4',5-Dipyrimidinyl in its Reaction with Piperidine", Khimiya Geterotsiklicheskikh Soedinenii, 6:821-826 (1979)—English Translation (12 pages).
Mitsuhashi et al, "Angiopoietins and TIE-2 Expression in Angiogenesis and Proliferation of Human Hepatocellular Carcinoma" Hepatology (2003) 37: 1105-1113.
Mori, Y. et al., "Downregulation of Tie2 gene by a novel antitumor sulfolipid, 3'-sulfoquinovosyl-1'-monoacylglycerol, targeting angiogenesis", Japanese Cancer Association, Cancer Sci., May 2008, vol. 99, No. 5, pp. 1063-1070.
Morris, et al., "Automated Docking of Flexible Ligands to Macromolecules", AutoDock Website, www.scripps.edu/mb/olson/doc/autodock/, printed Mar. 3, 2005 (3 pages).
Morris, et al., "Automated Docking Using a Lamarckian Genetic Algorithm and an Empirical Binding Free Energy Function", Journal of Computational Chemistry, 19(14):1639-1662 (1998).
Morstyn, et al., "Stem Cell Factor is a Potent Synergistic Factor in Hematopoiesis", Oncology, 51:205-214 (1994).
Moss, et al., Basic Terminology of Stereochemistry, Pure & Appl. Chem., 6812):2193-2222 (1996).
Muller et al, "Expression of Angiopoietin-1 and Its Receptor TEK in Hematopietic Cells From Patients With Myeloid Leukemia" Leukemia Research (2002) 26: 163-168.
Muller, "Glossary of Terms Used in Physical Organic Chemistry", Pure & Appl. Chem., 66(5):1077-1184 (1994).
Muller, et al., "A General Synthesis of 4-Substituted 1,1-Dioxo-1,2,5-thiadiazolidin-3-ones Derived from α-Amino Acids", J. Org. Chem., 54:4471-473 (1989).
Murayama, et al., "JNK (c-Jun NH2 Terminal Kinase) and p38 During Ischemia Reperfusion Injury in the Small Intestine" Transplantation, 81(9):1325-1330 (2006).
Mutlib, et al., "Disposition of 1-[3-(Aminomethyl)phenyl]-N-[3-fluoro-2'-(methylsulfonyl)-[1,1'-biphenyl]-4-yl]-3(trifluomethyl)-1H-pyrazole-5-carboxamide (DPC 423) by Novel Metabolic Pathways. Characterization of Unusual Metabolites by Liquid Chromatography/Mass Spectrometry and NMR", Chem. Res. Toxicol., 15:48-62 (2002).
Mutlib, et al., "P450-Mediated Metabolism of 1-[3-(Aminomethyl)phenyl]-N-[3-fluoro-2'-(methylsulfonyl)-[1,1'-biphenyl]-4-yl]-3(trifluomethyl)-1H-pyrazole-5-carboxamide (DCP 423) and Its Analogues to Aldoximes. Characterization of Glutathione Conjugates of Postulated Intermediates Derived from Aldoximes", Chem. Res. Toxicol., 15:63-75 (2002).
Nagano, M. et al. "Studies on Organic Sulfur Compounds. XIV. The Reaction of N-alkoxy-carbonyl-N'-(2-thiazolyl)thioureas with some oxidants." Chemical and Pharmaceutical Bulletin. vol. 21, No. 11, pp. 2408-2416. ISSN: 0009-2363. Nov. 1973.
Nagar et al., "Structural Basis for the Autoinhibition of c-Abl Tyrosine Kinase," *Cell* (Mar. 21, 2003) vol. 112, pp. 859-871.
Nagar, et al., "Crystal Structures of the Kinase Domain of c-Abl in Complex with the Small Molecule Inhibitors PD173955 and Imatinib (STI-571)", Cancer Research, 62:4236-4243 (2002).
Nakopoulou, et al., "c-Met Tyrosine Kinase Receptor Expression is Associated with Abnormal?—catenin Expression and Favourable Prognostic Factors in Invasive Breast Carcinoma", Histopathology, 36:313-325 (2000).
Nantaka-Namirski, et al., "Condensation Reaction of Ethyl (4-Uracil)—Acetate with Ethyl Orthoformate", ACTA Polon. Pharm XXVII, 28(5):455-463 (1971).
National Academy of Sciences, "Abstracts of Papers Presented at the Autumn Meeting, Nov. 14-16, 1960", Science, 132:1488-1501 (1960) (15 pages).
Nelson, H. et al., "Screening for Breast Cancer: An update for the U.S. Preventive Srvices Task Force", Annals of Intern Med. 2009; 151: pp. 727-737.
Nicolaou, et al., "Molecular Design and Chemical Synthesis of a Highly Potent Epothilone", ChemMedChem, 1:41-44 (2006).
Nikolaev, et al., "Solubility Polytherm in the System HN03-H20-(C4H90)PO(C4H9)2", Doklady Akademii Nauk SSSR, 160(4):841-844 (1965)—English Translation.
Nofal, et al., "Synthesis of Novel Uracil-5-Sulphonamide Derivatives of Possible Biological Activity", Egypt J. Chem., 33(4):375-380 (1990).
Nowell et al., "A Minute Chromosome in Human Chronic Granulocytic Leukemia," Science (Nov. 18, 1960) vol. 132, p. 1497.
O'Dell, et al., "Treatment of Rheumatoid Arthritis with Methotrexate Alone, Sulfasalazine and Hydroxychloroquine, or a Combination of All Three Medications", New England J. Med., 334(20):1287-1291(1996).
O'Neill, "Targeting Signal Transduction as a Strategy to Treat Inflammatory Diseases", Nature Review Drug Discovery, Published Online Jun. 9, 2006, www.nature.com/reviews/druqdisc <http://www.nature.com/reviews/druqdisc>(15 pages).
Okano, et al., "o-Bromophenylzinc Compound: A Readily Available and Efficient Synthetic Equivalent of o-Phenylene 1-Anion 2-Cation", Tetrahedron Letters 39:3001-3004 (1998).
Okishio, et al., "Differential Ligand Recognition by the Src and Phosphatidylinositol 3-Kinase Src Homology 3 Domains: Circular Dichroism and Ultraviolet Resonance Raman Studies", Biochemistry, 42:208-216 (2003).
Okishio, et al., "Identification of Tyrosine Residues Involved in Ligand Recognition by the Phosphatidylinositol 3-Kinase Src Homol-

(56) References Cited

OTHER PUBLICATIONS ogy 3 Domain: Circular Dichroism and UV Resonance Raman Studies", Biochemistry, 40:15797-15804 (2001).
Okishio, et al., "Role of the Conserved Acidic Residue Asp21 in the Structure of Phosphatidylinositol 3-Kinase Src Homolgy 3 Domain: Circular Dichroism and Nuclear Magnetic Resonance Studies", Biochemistry 40:119-129 (2001).
Okram, Barun et al: "A General Strategy for Creating "Inactive-Conformation" Abl Inhibitors" Chemistry&Biology (Cambridge, MA, US), 13(7), 779-786 CODEN: CBOLE2; ISSN: 1074-5521, 2006, XP002469183 table 1 the whole document.
Palmer, Brian, D. et al: "Structure-Activity Relationships for 2-Anilino-6-Phenylpyrido[2,3-d]Pyrimidin-7(8H)-Ones as Inhibitors of the Cellular Checkpoint Kinase Wee1" Bioorganic & Medicinal Chemistry Letters, 15(7), 1931-1935 CODEN: BMCLE8; ISSN: 0960-894X, 2005, XP004789411 p. 1933.
Parang, et al., "Mechanism-based Design of a Protein Kinase Inhibitor", Nature Structural Biology, 8(1):37-41 (2001).
Pargellis, et al., "Inhibition of p38 MAP Kinase by Utilizing a Novel Allosteric Binding Site", Nature Structural Biology, 9(4):268-272 (2002).
Park, et al., "Mechanism of met Oncogene Activation", Cell, 45:895-904 (1986).
Pearlman, et al., "Assisted Model Building with Energy Refinement", Amber Home Page, amber.scripts.edu.
Pedersen, "The Preparation of Some N-Methyl-1,2,3-Triazoles", Acta Chimica Scandinavica, 13(5):888-892 (1959).
Peinado et al, "Melanoma Exosomes Educate Bone Marrow Progenitor Cells Toward a Pro-Metastatic Phenotype Through Met" *Nature Medicine* (2012) 18: 883-891.
Peng, et al., "Identification of Novel Inhibitors of BCR-ABL Tyrosine Kinase via Virtual Screening", Bioorganic & Medicinal Chemistry Letters, 13:3693-3699 (2003).
Pereira, et al., "The Role of c-kit and Imatinib Mesylate in Uveal Melonoma", Journal of Carcinogenesis, 4:19 (2005), downloaded from www.carcinogenesis.com/content/4/1/19, <http://www.carcinogenesis.com/content/4/1/19> Sep. 3, 2008 (8 pages).
Peyssonnaux, C. et al., "The RaflMEK/ERK pathway: new concepts of activation," Biol. Cell (2001) 93: 53-62.
Picard, et al., "Inhibitors of Acyl-CoA: Cholesterol O-Acyltrasferase. 17. Structure-Activity Relationships of Several Series of Compounds Derived from N-Chlorosulfonyl Isocyanate", J. Med. Chem., 39:1243-1252 (1996).
Pierrat, et al, "Solid Phase Synthesis of Pyridine-Based Derivatives from a 2-Chloro-5-Bromopyridine Scaffold," J Comb. Chem. (2005) 7 (6): 879-886.
Pluk et al., "Autoinhibition of c-Abl," *Cell* (Jan. 25, 2002) vol. 108, pp. 247-259.
Ponzetto, et al., "A Novel Recognition Motif for Phosphatidylinositol 3-Kinase Binding Mediates Its Association with the Hepatocyte Growth Factor/Scatter Factor Receptor", Molecular and Cellular Biology, 13(8):4600-4608 (1993).
Raimbault, et al., "Effects of pH and KCI on the Conformations of Creatine Kinase from Rabbit Muscle", Eur. J. Biochem., 234:570-578 (1995).
Ranatunge, et al, "Synthesis and Selective Cyclooxygenase-2 Inhibitory Activity of a Series of Novel, Nitric Oxide Donor-Containing Pyrazoles," J Med Chem. (2004) 47: 2180-2193.
Rebek, et al. "Convergent Functional Groups: Synthetic and Structural Studies", J. Am. Chem. Soc., 107:7476-7481 (1985).
Rebek, et al., "Convergent Functional Groups. 2. Structure and Selectivity in Olefin Epoxidation with Peracids", J. Org. Chem., 51:1649-1653 (1986).
Reed, et al., "Circular Dichroic Evidence for an Ordered Sequence Ligand/Binding Site Interactions in the Catalytic Reaction of the CAMP-Dependent Protein Kinase", Biochemistry, 24:2967-2973 (1985).
Regan, et al., "Pyrazole Urea-Based Inhibitors of p38 MAP Kinase: From Lead Compound to Clinical Candidate", J. Med. Chem., 45:2994-3008 (2002).
Regan, et al., "Structure-Activity Relationships of the p38α MAP Kinase Inhibitor 1-(5-*tert*-Butyl-2-*p*-tolyl-2H-pyrazol-3-yl)-3-[4-(2-morpholin-4-yl-ethoxy)naph-thalen-1-yl]urea (BIRB 796)", J. Med. Chem., 46:4676-4686 (2003).
Rooney, et al., "Inhibitors of Glycolic Acid Oxidase. 4-Substituted 3-Hydroxy-1H-pyrrole-2,5-dione Derivatives", J. Med. Chem., 26(5):700-714 (1983).
Roux, et al., "ERK and p38 MAPK-Activated Protein Kinases: a Family of Protein Kinases with Diverse Biological Functions", Microbiology and Molecular Biology Reviews, 68(2):320-344 (2004).
Rowley, "A New Consistent Chromosomal Abnormality in Chronic Myelogenous Leukaemia identified by Quinacrine Fluorescence and Giemsa Staining," *Nature* (Jun. 1, 1973) vol. 243, pp. 290-293.
Russell, et al., "3-[3-(Piperdin-1-yl)propyl]indoles as Highly Selective h5-HT1D Receptor", J. Med. Chem., 42:4981-5001 (1999).
Saharinen, P. et al., "Therapeutic targeting of the angiopoietin-TIE pathway", Nature Reviews, Drug Discovery, vol. 16, Sep. 2017, pp. 635-661.
Saiga, et al., "Consecutive Cross-Coupling of o-Phenylenedizinc Compound with Acyl and/or Aryl Halides in the Presence of Pd(O)-tris(2,4,6-trimethoxyphenyl)phosphine", Tetrahedron Letters, 41:4629-4632 (2000).
Sakamoto, et al., "Condensed Heteroaromatic Ring Systems. XIX. Synthesis and Reactions of 5-(Tributylstannyl)Isoxazoles", Tetrahedron, 47(28):5111-5118 (1991).
Sakuma, et al., "*c-kit* Gene Mutations in Intracranial Germinomas", Cancer Sci, 95(9):716-720 (2004).
Satsangi, et al., "1-(4-Substituted-thiazol-2-yl)hydatoins as Anti-inflammatory and CNS—Active Agents", Pharmazie, 38:341-342 (1983).
Sawyers, "Chronic Myeloid Leukemia," *The New England Journal of Medicine* (Apr. 29, 1999) vol. 340, No. 17, pp. 1330-1340.
Schindler et al. "Structural Mechanism for STI-571 Inhibition of Abelson Tyrosine Kinase" Science (2000) 289: 1938-1942.
Schindler et al., "Structural Mechanism for STI-571 Inhibition of Abelson Tyrosine Kinase," Science (Sep. 15, 2000) vol. 289, pp. 1938-1942.
Schlosser, et al., "Regiochemically Flexible Substitutions of Di-, Tri-, and Tetrahalopy:ridines: The Trialkylsily Trick," J Org. Chem. (2005) 70: 2494-2502.
Schmidt, et al., "Germline and Somatic Mutations in the Tyrosine Kinase Domain of the MET proto-oncogene in Papillary Renal Carcinomas", Nature Genetics, 16:68-73 (1997).
Schmidt, et al., "Novel Mutations of the MET Proto-oncogene in Papillary Renal Carcinomas", Oncogene, 18:2343-2350 (1999).
Seimiya, et al., "Telomere Shortening and Growth Inhibition of Human Cancer Cells by Novel Synthetic Telomerase Inhibitors MST-312, MST-295, and MST-199", Molecular Cancer Therapeutics, 1:657-665 (2002).
Seminario, et al., "Theoretical Study of a Molecular Resonant Tunneling Diode", J. Am. Chem. Soc., 122:3015-3020 (2000).
Shah et al., "Overriding Imatinib Resistance with a Novel ABL Kinase Inhibitor," *Science* (Jul. 16. 2004) vol. 305, pp. 399-401.
Shah, et al., "Circular Dichroic Studies of Protein Kinase C and its Interactions with Calcium and Lipid Vesicles", Biochimica et Biophysica Acta, 1119:19-26 (1992).
Shi, et al., "Abnormal Diels-Alder Reaction of 5-Alkoxythiazoles with Highly Reactive Dienophiles; 4-Phenyl-3H-1,2,4-triazole-3,5(4H)-dione, Diethyl Azodicarboxylate, and Diethyl Oxomalonate", Bull. Chem. Soc. Jpn., 65:3315-3321 (1992).
Shinkai, et al., "Coenzyme Models, Part 45. Synthesis of Atropisomeric Flavins and their Novel Redox-induced Racemisation", J. Chem. Soc. Perkin Trans., pp. 313-319 (1988).
Shiozaki, et al., "Impaired Differentiation of Endocrine and Exocrine Cells of the Pancreas in Transgenic Mouse Expressing the Truncated Type II Activin Receptor", Biochimica et Biophysica Acta, 1450:1-11 (1999).
Shirakawa, K. et al., "Tumor-infiltrating endothelial cells and endothelial precursor cells in inflammatory breast cancer", Int. J. Cancer: 99, Wiley-Liss, Inc., 2002, pp. 344-351.
Sircar et al., "Synthesis of 4-Hydroxy-N-[5-(hydroxymethyl)-3-isoxazolyl]2-methyl-2H-1,2-bsnzo-thiazine-3-carboxamide 1,1-

(56) References Cited

OTHER PUBLICATIONS

Dioxide and [(5-Methyl-3-isoxazolyl)amino]oxoacetic Acid. Major Metabolites of Isoxicam," *J. Org. Chem.* (1985) vol. 50, pp. 5723-5727.
Smith, Bryan D., et al., "Abstract B78: Rebastinib, a Small Molecule TIE2 Kinase Inhibitor, Prevents Primary Tumor Growth and Lung Metastasis in the PyMT Breast Cancer Model", Internet, Feb. 2013 (Feb. 2013).
Stout, et al., "High-Throughput Structural Biology in Drug Discovery: Protein Kinases", Current Pharmaceutical Design, 10:1069-1082 (2004).
Sugden, et al., ""Stress-Responsive" Mitogen-Activated Protein Kinases (c-Jun N-Terminal Kinases and p38 Mitogen-Activated Protein Kinases) in the Myocardium", Circulation Research—Journal of the American Heart Association, 83:345-352 (1998).
Takase et al., "Practical Synthesis of 3-Amino-5-tert-Butylisoxazole from 4,4-Dimethyl-3-Oxopentanenitrile with Hydroxylamine," Heterocycles (1991) vol. 32, No. 6, pp. 1153-1158.
Tanaka et al, "Biologic Significance of Angiopoietin-2 Expression in Human Hepatocellular Carcinoma" J. Clin Invest (1999) 103: 341-345.
Tanis, et al., "Two Distinct Phosphorylation Pathways Have Additive Effects on Abl Family Kinase Activation", Molecular and Cellular Biology, 23(11):3884-3896 (2003).
Teague, "Implications of Protein Flexibility for Drug Discovery", Nature Reviews, 2:527-541 (2003).
Tominaga, et al., "General model for Estimation of the Inhibition of Protein Kinases Using Monte Carlo Simulations", J. Med. Chem., 47:2534-2549 (2004).
Tremblay, et al., "Efficient Solid-Phase Synthesis of Sulfahydantoins", J. Comb. Chem., 4:429-435 (2002).
Tsuzuki, et al., "Synthesis and Structure-Activity Relationships of Novel ?-Substituted 1,4-Dihydro-4-oxo-1-(2-thiazolyl)-1,8-napthyridine-3-carboxylic Acids as Antitumor Agents. Part 2", J. Med. Chem., 47:2097-2109 (2004).
Van Etten, "Cycling, stressed-out and nervous: cellular functions of c-Abl," *Trends in Cell Biology* (May 1999) vol. 9, pp. 179-186.
Venter, et al., "The Sequence of the Human Genome", Science, 291:1304-1351, Feb. 16, 2001; Erratum, Jun. 8, 2001 (49 pages).
Vippagunta, et al., "Crystalline Solids", Advanced Drug Delivery Reviews, 48, (2001), pp. 3-26.
Von Bubnoff et al., "BCR-ABL gene mutations in relation to clinical resistance of Philadelphia-chromosome-positive leukemia to STI571. a prospective study," *The Lancet* (Feb. 9, 2002) vol. 359, pp. 487-491.
Waetzig, et al., "Review Article: Mitogen-Activated Protein Kinases in Chronic Intestinal Inflammation—Targeting Ancient Pathways to Treat Modern Diseases", Aliment Pharmacol Ther, 18:17-32 (2003).
Wan et al., "Mechanism of Activation of the RAF-ERK Signaling Pathway by Oncogenic Mutations of B-RAF," *Cell* (Mar. 19, 2004) vol. 116. pp. 855-867.
Welker, et al., "Glucocorticoid-Induced Modulation of Cytokine Secretion from Normal and Leukemic Human Myelomonocytic Cells", Int. Arch. Allergy Immunol, 109:110-115 (1996).
Wentland, et al., "3-Quinolinecarboxamides. A Series of Novel Orally-Active Antiherpetic Agents", J. Med. Chem., 36:1580-1596 (1993).
Wilson, et al., "The Structural Basis for the Specificity of Pyridinylimidazole Inhibitors of p38 MAP Kinase", Chemistry & Biology, 4(6):423-431 (1997).
Wilson, et el., "Laser-Jet Delayed Trapping: Electron-Transfer Trapping of the Photoenol from 2-Methylbenzophenone", J. Am. Chem. Soc., 109:4743-4745 (1987).
Wolter, et al., "Copper-Catalyzed Coupling of Aryl Iodides with Aliphatic Alcohols", Organic Letters, 4(6):973-976 (2002).
Wrana, et al., "Mechanism of Activation of the TGF-β Receptor", Nature, 370:341-347 (1994).
Wu, et al., "Discovery of a Novel Family of CDK Inhibitors with the Program LIDAEUS: Structural Basis for Ligand-Induced Disordering of the Activation Loop", Structure, 11:399-410 (2003).
Yang, et al., "Molecular Mechanism for the Regulation of Protein Kinase B/Akt by Hydrophobic Motif Phosphorylation", Molecular Cell, 9:1227-1240 (2002).
Yang, et al., "Palladium-Catalyzed Amination of Arly Halides and Sulfonates", Journal of Organometallic Chemistry, 576:125-146 (1999).
Yarden, et al., "Human Proto-oncogene c-kit: a New Cell Surface Receptor Tyrosine Kinase for an Unidentified Ligand", The EMBO Journal, 6(11):3341-3351 (1987).
Yoneda, et al., "A New Synthesis of Purines", J.C.S. Chem. Comm., p. 551 (1974).
Yonezawa, et al., "Synthesis of Sequentially Controlled Isomeric, Wholly aromatic Polyketones Composed of 2-trifluoromethylbiphenylene and 2,2'-dimethoxybiphenylene Units", Reactive & Functional Polymers, 52:19-30 (2002).
Yoshimoto, et al., "Correlation Analysis of Baker's Studies on Enzyme Inhibition. 2. Chymotrypsin, Trypsin, Thymidine Phosphorylase, Uridine Phosphorylase, Thimidylate Synthetase, Cytosine Nucleoside Deaminase, Dihodrofolate Reductase, Malate Dehydrogenase, Glutamate Dehydrogenase, Lactate Dehydrogenase, and Glyceraldehyde-phosphate Dehydrogenase", Journal of Medicinal Chemistry, 19(1):71-98 (1976).
Yoshino, et al., "Organic Phosphorous Compounds. 2. Synthesis and Coronary Vasodilator Activity of (Benzothiazolybenzyl) Phosphonate Derivatives", J. Med. Chem., 32:1528-1532 (1989).
Yu, et al., "Frequency of TPR-MET Rearrangement in Patients with Gastric Carcinoma and in First-Degree Relatives", Cancer, 88(8):1801-1806 (2000).
Zaidi, et al., "New Anti-Mycobacterial Hydantoins", Pharmazie, 35:755-756 (1980).
Zhen, et al., "Structural and Functional Domains Critical for Constitutive Activation of the HGF-Receptor (Met)", Oncogene, 9(6):1691-1697 (1994).
Zinner, et al., "Zur Weiteren Kenntnis Bicyclischer 3.5-Dioxopyrazolidine", Die Pharmazie, 25(5):309-312 (1970).
Zvilichovsky, et al., "Aminolysis and Polymerization of 3-(p-Toluenesulfonoxy) Hydantoin", Israel Journal of Chemistry, 7:547-554 (1969).
Triana, P. et al., Activity of a TIE2 inhibitor (rebastinib) in a patient with a life-threatening cervicofacial venous malformation, Pediatr. Blood Cancer, e30404 (2023).

* cited by examiner (WT : wild type HUVECs, LF : L914F, RW : R849W, RX : R1099*, YCE RC : Y897CE R915C, YFE RL : Y897FE R915L, TE T : T1105NE T1106P. N = 3)

(WT : wild type HUVECs, LF : L914F, RW : R849W, RX : R1099*, YCE RC : Y897CE R915C, YFE RL : Y897FE R915L, TE T : T1105NE T1106P. N = 3)

(WT : wild type HUVECs, LF : L914F, RW : R849W, RX : R1099*, YCE RC : Y897CE R915C, YFE RL : Y897FE R915L, TE T : T1105NE T1106P. N = 3)

(WT : wild type HUVECs, NX : non treated cells, REBA : Formula I 100 nM, N = 3; 5x vs 10x)

(WT : wild type HUVECs, YCE RC : Y897CE R915C, YFE RL : Y897FE R915L, NX : non treated cells, REBA : Formula I 100 nM. N = 3; 5x vs 10x)

(WT : wild type HUVECs, TE T : T1105NE T1106P, NX : non treated cells, REBA : Formula I 100 nM. N = 3; 5x vs 10x)

(WT : wild type HUVECs, LF : L914F, RW : R849W, RX : R1099*, NX : non treated cells, REBA : Formula I 100 nM. Normalized to GAPDH, N=3; pE value: vs DMSO treatment)

(WT : wild type HUVECs, LF : L914F, YCE RC : Y897CE R915C, YFE RL : Y897FE R915L, TE T : T1105NE T1106P, NX : non treated cells, REBA : Formula I 100 nM. Normalized to GAPDH, N=2)

(WT : wild type HUVECs, LF : L914F, YCE RC : Y897CE R915C, YFE RL : Y897FE R915L, TE T : T1105NE T1106P, NX : non treated cells, REBA : Formula I 100 nM. Normalized to GAPDH, N=2)

(WT : wild type HUVECs, LF : L914F, RW : R849W, RX : R1099*, NX : non treated cells, REBA : Formula I 100 nM. Normalized to GAPDH, N=3; pE value: vs DMSO treatment)

(WT : wild type HUVECs, LF : L914F, YCE RC : Y897CE R915C, YFE RL : Y897FE R915L, TE T : T1105NE T1106P, NX : non treated cells, REBA : Formula I 100 nM. Normalized to GAPDH, N=2)

(WT : wild type HUVECs, LF : L914F, RW : R849W, RX : R1099*, YCE RC : Y897CE R915C, YFE RL : Y897FE R915L, TE T : T1105NE T1106P, ECM : extracellular matrix. N = 2)

n: WT = 5-6; L914F = 16 n: WT = 5-6; L914F = 16

```
                         SEQUENCE LISTING


<160> NUMBER OF SEQ ID NOS: 1

<210> SEQ ID NO 1
<211> LENGTH: 354
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Gln Leu Lys Arg Ala Asn Val Gln Arg Arg Met Ala Gln Ala Phe Gln
1               5                   10                  15

Asn Val Arg Glu Glu Pro Ala Val Gln Phe Asn Ser Gly Thr Leu Ala
            20                  25                  30

Leu Asn Arg Lys Val Lys Asn Asn Pro Asp Pro Thr Ile Tyr Pro Val
        35                  40                  45

Leu Asp Trp Asn Asp Ile Lys Phe Gln Asp Val Ile Gly Glu Gly Asn
    50                  55                  60

Phe Gly Gln Val Leu Lys Ala Arg Ile Lys Lys Asp Gly Leu Trp Met
65                  70                  75                  80

Asp Ala Ala Ile Lys Arg Met Lys Glu Tyr Ala Ser Lys Asp Asp His
                85                  90                  95

Arg Asp Phe Ala Gly Glu Leu Glu Val Leu Cys Lys Leu Gly His His
            100                 105                 110

Pro Asn Ile Ile Asn Leu Leu Gly Ala Cys Glu His Arg Gly Tyr Leu
        115                 120                 125

Tyr Leu Ala Ile Glu Tyr Ala Pro His Gly Asn Leu Leu Asp Phe Leu
    130                 135                 140

Arg Lys Ser Arg Val Leu Glu Thr Asp Pro Ala Phe Ala Ile Ala Asn
145                 150                 155                 160

Ser Thr Ala Ser Thr Leu Ser Ser Gln Gln Leu Leu His Phe Ala Ala
```

-continued

```
                165                 170                 175

Asp Val Ala Arg Gly Met Asp Tyr Leu Ser Gln Lys Gln Phe Ile His
            180                 185                 190

Arg Asp Leu Ala Ala Arg Asn Ile Leu Val Gly Glu Asn Tyr Val Ala
        195                 200                 205

Lys Ile Ala Asp Phe Gly Leu Ser Arg Gly Gln Glu Val Tyr Val Lys
    210                 215                 220

Lys Thr Met Gly Arg Leu Pro Val Arg Trp Met Ala Ile Glu Ser Leu
225                 230                 235                 240

Asn Tyr Ser Val Tyr Thr Thr Asn Ser Asp Val Trp Ser Tyr Gly Val
                245                 250                 255

Leu Leu Trp Glu Ile Val Ser Leu Gly Gly Thr Pro Tyr Cys Gly Met
            260                 265                 270

Thr Cys Ala Glu Leu Tyr Glu Lys Leu Pro Gln Gly Tyr Arg Leu Glu
        275                 280                 285

Lys Pro Leu Asn Cys Asp Asp Glu Val Tyr Asp Leu Met Arg Gln Cys
    290                 295                 300

Trp Arg Glu Lys Pro Tyr Glu Arg Pro Ser Phe Ala Gln Ile Leu Val
305                 310                 315                 320

Ser Leu Asn Arg Met Leu Glu Glu Arg Lys Thr Tyr Val Asn Thr Thr
                325                 330                 335

Leu Tyr Glu Lys Phe Thr Tyr Ala Gly Ile Asp Cys Ser Ala Glu Glu
            340                 345                 350

Ala Ala
```

METHODS FOR TREATING VASCULAR MALFORMATIONS

CROSS-REFERENCE TO RELATED APPLICATIONS

This application claims priority to U.S. Ser. No. 62/885,519 filed Aug. 12, 2019, the contents of which are incorporated herein by reference in their entirety.

SEQUENCE LISTING

The instant application contains a Sequence Listing which has been submitted electronically in ASCII format and is hereby incorporated by reference in its entirety. Said ASCII copy, created on Nov. 11, 2020, is named DCP-083_SL.txt and is 3,451 bytes in size.

BACKGROUND

Tunica interna endothelial cell kinase-2 (TIE2) is largely restricted to expression in endothelial cells of the vasculature. TIE2 is the receptor for angiopoietin 1 (ANGPT1), angiopoietin 2 (ANGPT2), and angiopoietin 4 (ANGPT4) and this signaling system plays an important role in both angiogenesis (sprouting of new vessels from existing vessels) and vasculogenesis (de novo new vessel formation).

Vascular malformations comprise a diverse set of diseases of the vasculature. These include venous malformations, lymphatic malformations, capillary malformations, arterial malformations, and arterio-venous malformations. Any blood vessel type or combination can be involved in the malformation. Vascular malformations grow with time and rapid growth and local tissue infiltration can occur. Venous malformations can be localized or occur multifocally. Venous malformations can be associated with pain, swelling, bleeding, disfigurement, thrombosis, and other significant morbidities. Venous malformations can affect tissues such as skin, joints, muscles, the intestines, and bone. Many venous malformations can be treated with surgery, laser therapy, or sclerotherapy, however not all are amenable to these treatments. In most cases the venous malformation recurs after conventional treatment.

In approximately 50% of cases venous malformations have been linked to germline or associated with somatic mutations in TIE2 kinase. These mutations activate TIE2 kinase, leading to dysregulated endothelial cell growth and venous malformation. Thus, there is a need for new treatments for these diseases associated with TIE2 alterations.

SUMMARY

Described herein are compounds that are inhibitors of TIE2 kinase and their use in the treatment or prophylaxis against growth of venous malformations. This disclosure relates to methods of using compound of Formula I, described below, as potent inhibitors of TIE2 for treating venous malformations:

Formula I

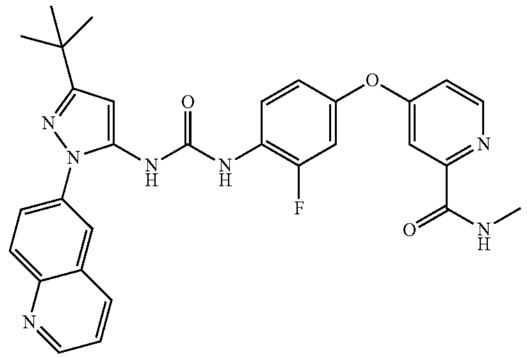

or a pharmaceutically acceptable salt thereof.

For example, provided herein is a method for treating TIE2 kinase-mediated vascular anomalies or TIE2 kinase mutant-mediated vascular anomalies, in a patient in need thereof, comprising administering to the patient a therapeutically effective amount of the compound of Formula I, or a pharmaceutically acceptable salt thereof.

Additionally, provided herein is a method for treating vascular anomalies, in a patient in need thereof, comprising administering to the patient a therapeutically effective amount of the compound of Formula I, or a pharmaceutically acceptable salt thereof, wherein the vascular anomalies are mediated by TIE2 kinase or by TIE2 kinase mutant-mediated.

Furthermore, provided herein is a compound of Formula I or a pharmaceutically acceptable salt thereof for use in the treatment of TIE2 kinase-mediated vascular anomalies or TIE2 kinase mutant-mediated vascular anomalies in a patient in need thereof, comprising administering to the patient a therapeutically effective amount of the compound of Formula I, or a pharmaceutically acceptable salt thereof.

Also provided herein is a method for treating venous malformations in a patient in need thereof, comprising administering to the patient about 100 mg to about 200 mg, once or twice daily, of the compound of Formula I, or a pharmaceutically acceptable salt thereof.

Also provided herein is a compound of Formula I, or a pharmaceutically acceptable salt thereof, for use in the treatment of venous malformations in a patient in need thereof, comprising administering to the patient about 100 mg to about 200 mg, once or twice daily, of the compound of Formula I, or a pharmaceutically acceptable salt thereof.

DETAILED DESCRIPTION

Figure 1A:
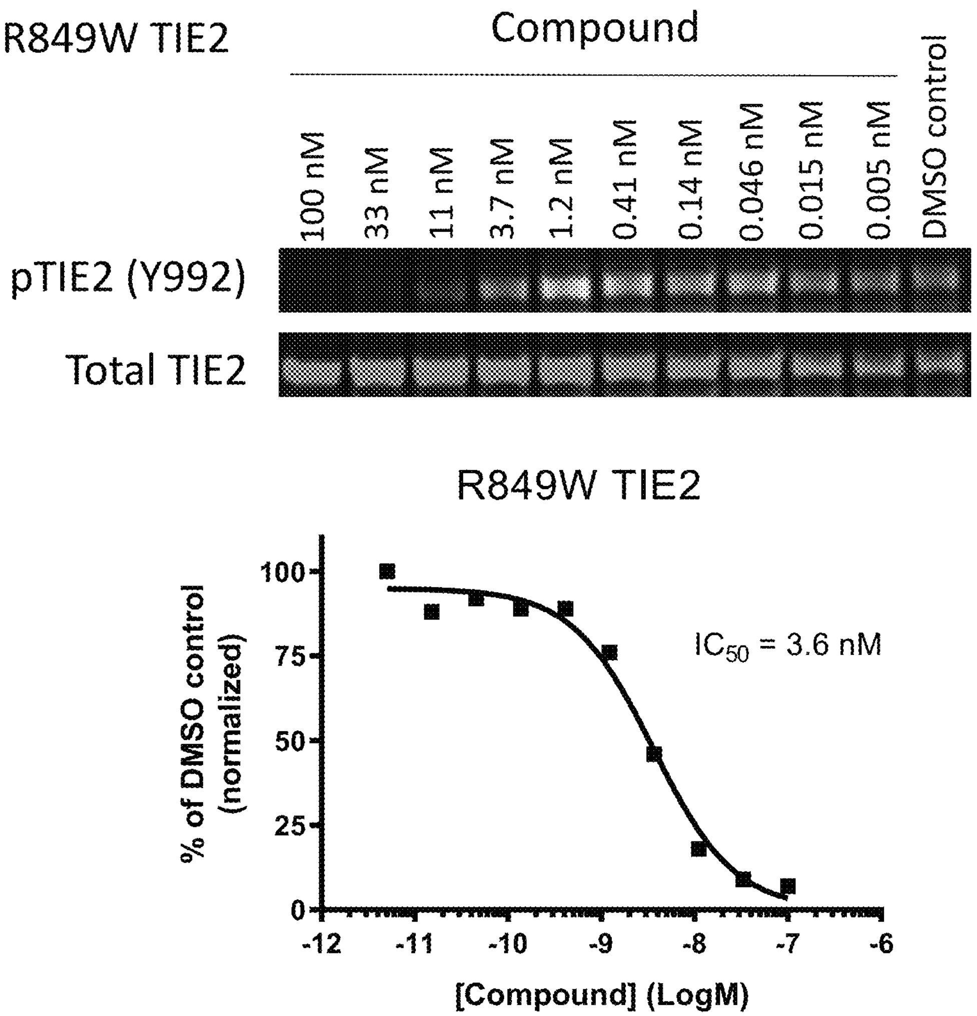
FIGS. 1A-E shows the inhibition of phosphorylation of various mutant forms of TIE2 (R849W, L914F, R1099*, Y897C/R915C, and Y897F/R915L, respectively) using the compound of Formula I in assays using transfected CHO cells.
Figure 1B:
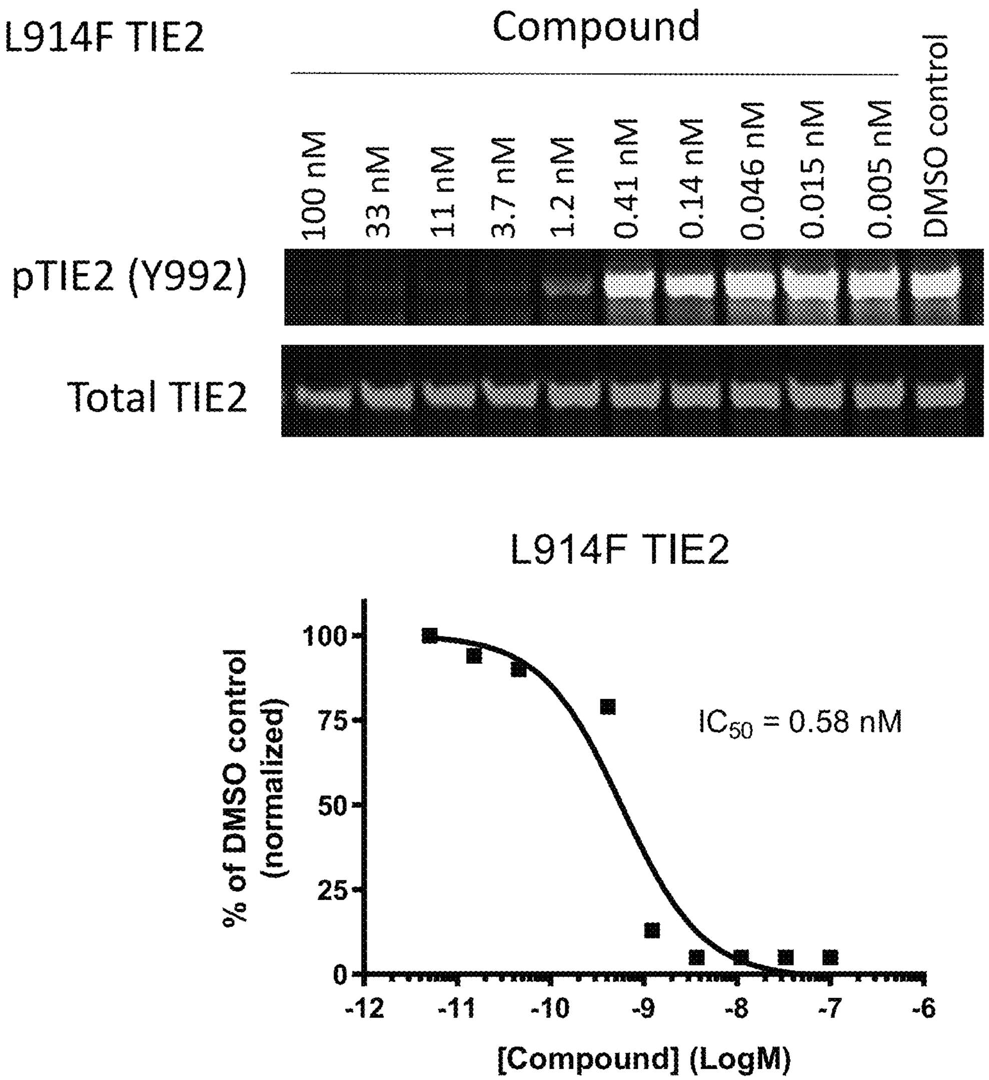
Figure 1C:
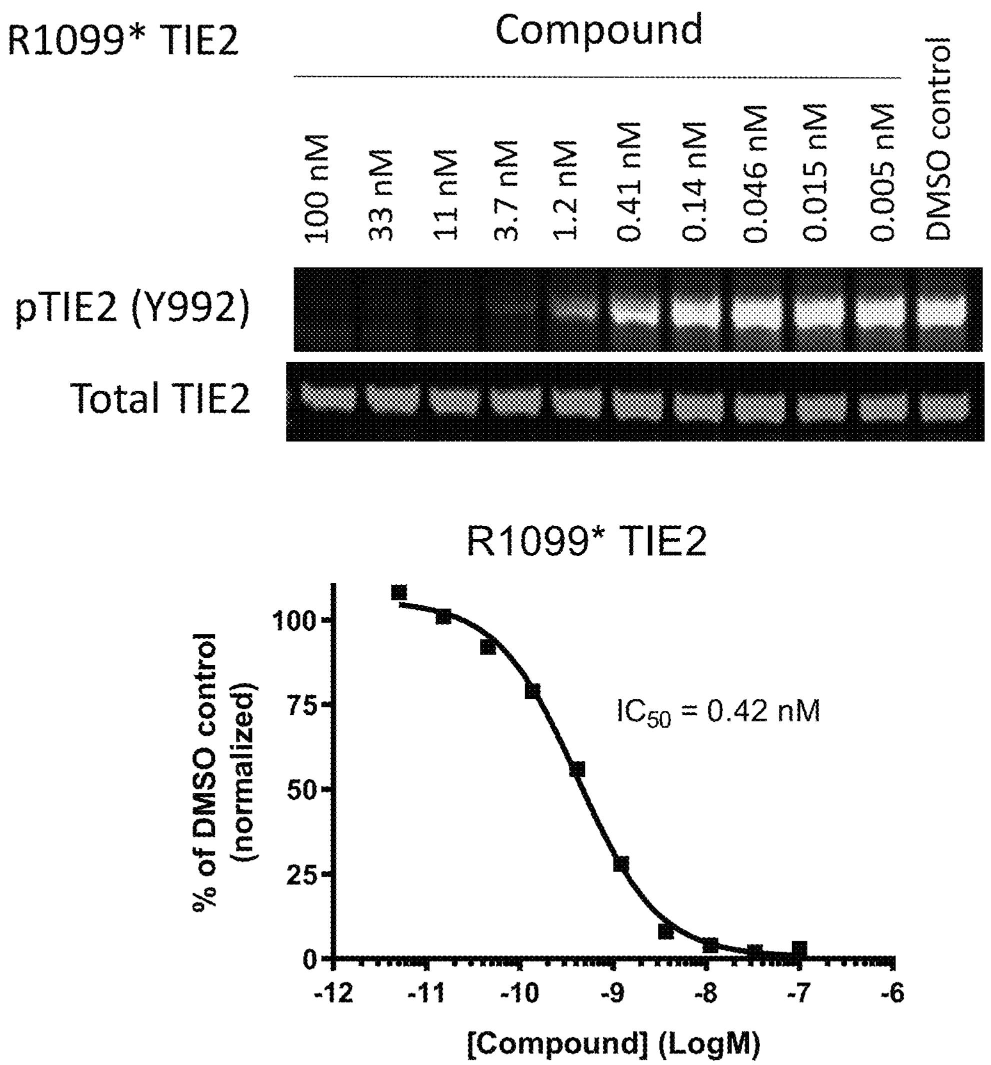
Figure 1D:
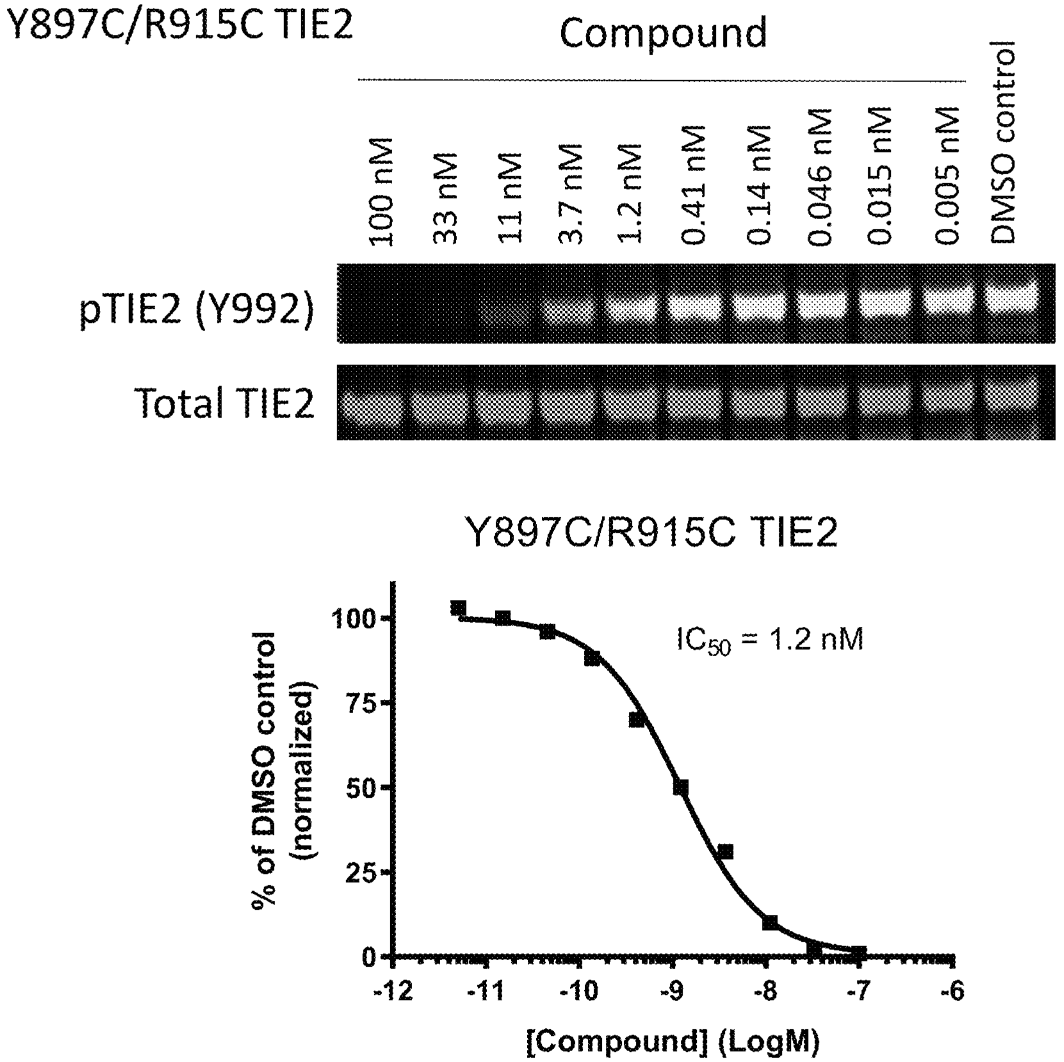
Figure 1E:
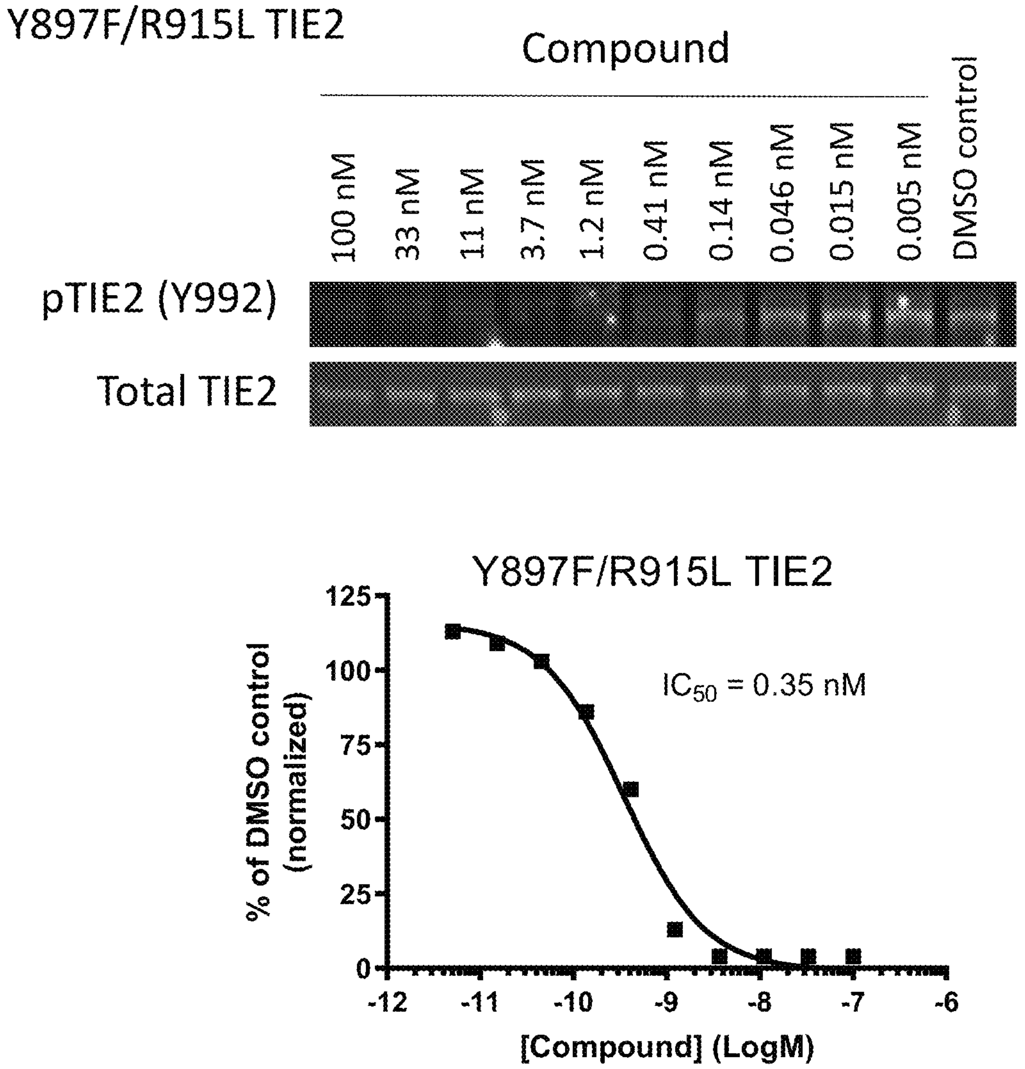

The features and other details of the disclosure will now be more particularly described. Certain terms employed in the specification, examples and appended claims are collected here. These definitions should be read in light of the remainder of the disclosure and as understood by a person of skill in the art. Unless defined otherwise, all technical and scientific terms used herein have the same meaning as commonly understood by a person of ordinary skill in the art.

Definitions

The terms “Individual,” “patient,” or “subject” are used interchangeably and include any animal, including mammals, preferably mice, rats, other rodents, rabbits, dogs, cats, swine, cattle, sheep, horses, or primates, and most preferably humans. The compounds described herein can be administered to a mammal, such as a human, but can also be administered to other mammals such as an animal in need of veterinary treatment, e.g., domestic animals (e.g., dogs, cats, and the like), farm animals (e.g., cows, sheep, pigs, horses, and the like) and laboratory animals (e.g., rats, mice, guinea pigs, and the like).

“Pharmaceutically or pharmacologically acceptable” include molecular entities and compositions that do not produce an adverse, allergic or other untoward reaction when administered to an animal, or a human, as appropriate. For human administration, preparations should meet sterility, pyrogenicity, and general safety and purity standards as required by FDA Office of Biologics standards.

The term “pharmaceutically acceptable carrier” or “pharmaceutically acceptable excipient” as used herein refers to any and all solvents, dispersion media, coatings, isotonic and absorption delaying agents, and the like, that are compatible with pharmaceutical administration. The use of such media and agents for pharmaceutically active substances is well known in the art. The compositions may also contain other active compounds providing supplemental, additional, or enhanced therapeutic functions.

The term “pharmaceutical composition” as used herein refers to a composition comprising at least one compound as disclosed herein formulated together with one or more pharmaceutically acceptable carriers.

The term "pharmaceutically acceptable salt(s)" as used herein refers to pharmaceutically acceptable organic or inorganic salts of a compound disclosed herein. These may be salts of acidic or basic groups that may be present in compounds used in the compositions. Compounds included in the present compositions that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, including, but not limited to, malate, oxalate, chloride, bromide, iodide, nitrate, sulfate, bisulfate, phosphate, acid phosphate, isonicotinate, acetate, lactate, salicylate, citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts, alkali metal (e.g., sodium and potassium) salts, alkaline earth metal (e.g., magnesium) salts, and ammonium salts. A pharmaceutically acceptable salt can involve the inclusion of another molecule such as an acetate ion, a succinate ion or other counter ion. The counter ion can be any organic or inorganic moiety that stabilizes the charge on the parent compound. Furthermore, a pharmaceutically acceptable salt can have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion. The compounds of the disclosure may contain both acidic and basic groups; for example, one amino and one carboxylic acid group. In such a case, the compound can exist as an acid addition salt, a zwitterion, or a base salt. If the compound as disclosed herein is a base, the desired pharmaceutically acceptable salt can be prepared by any suitable method available in the art, for example, treatment of the free base with an inorganic acid, such as hydrochloric acid, hydrobromic acid, sulfuric acid, nitric acid, methanesulfonic acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like. If the compound as disclosed herein is an acid, the desired pharmaceutically acceptable salt can be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include, but are not limited to, organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

The terms "treating" or "treatment" as used herein, include reversing, reducing, or arresting the symptoms, clinical signs, and underlying pathology of a condition in manner to improve or stabilize a subject's condition. As used herein, and as well understood in the art "treatment" is an approach for obtaining beneficial or desired results, including clinical results. Beneficial or desired clinical results can include, but are not limited to, alleviation, amelioration, or slowing the progression, of one or more symptoms or conditions associated with a condition, e.g., cancer, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Exemplary beneficial clinical results are described herein.

The terms "administer," "administering," or "administration" as used in this disclosure refer to either directly administering a composition or pharmaceutically acceptable salt of the compound or a composition to a subject, or administering a prodrug derivative or analog of the composition or pharmaceutically acceptable salt of the compound or composition to the subject, which can form an equivalent amount of active compound within the subject's body.

In the present specification, the term "therapeutically effective amount" means the amount of the subject compound that will elicit the biological or medical response of a tissue, system or animal, (e.g. mammal or human) that is being sought by the researcher, veterinarian, medical doctor or other clinician. The compounds described herein are administered in therapeutically effective amounts to treat the disclosed disorders.

The compound of Formula I is also referred to herein as "rebastinib."

The present disclosure relates in part to methods for the treatment (blocking) or prophylaxis against growth of venous malformations. Such disclosed methods can include administering to a patient in need of treatment or reduction of prophylactic effects of these conditions an effective amount of a compound of Formula I or a pharmaceutically acceptable salt thereof, for example, as part of a dosing regimen that regulates TIE2 inhibition.

In some embodiments, a compound of Formula I is a sulfonate salt according to Formula II. Formula II, for example, is a potent inhibitor of TIE2, the receptor tyrosine kinase for angiopoietin ligands.

Formula II

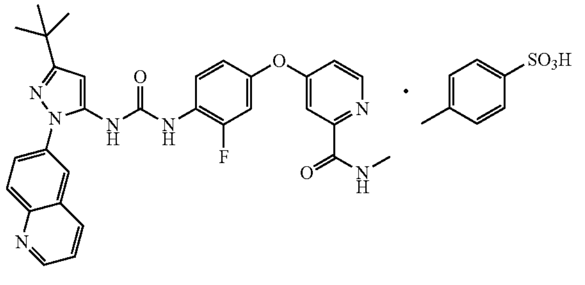

Exemplary methods include treating venous malformation in a patient, for example, where such patients have TIE2 expression, mutation, or alteration in endothelial cells that may cause or lead to the growth of venous malformations. Such methods can include administering a compound of Formula I or pharmaceutically acceptable salts thereof to the patient suffering from venous malformations. For example, provide compounds, e.g., a compound of Formula I, or a pharmaceutically acceptable salt thereof may inhibit processes including growth of venous malformations. Contemplated compounds include the free base of Formula I.

Effective amounts, toxicity, and therapeutic efficacy can be determined by standard pharmaceutical procedures in cell cultures or experimental animals, e.g., for determining the LD50 (the dose lethal to about 50% of the population) and the ED50 (the dose therapeutically effective in about 50% of the population). The dosage can vary depending upon the dosage form employed and the route of administration utilized. The dose ratio between toxic and therapeutic effects is the therapeutic index and can be expressed as the ratio LD50/ED50. In some embodiments, the compositions and methods exhibit large therapeutic indices. Levels of the described compositions in plasma can be measured, for example, by high performance liquid chromatography, and the effects of any particular dosage can be monitored by a suitable bioassay. The dosage can be determined by a physician and adjusted, as necessary, to suit observed effects of the treatment.

In certain embodiments, a prophylactic effect will result in a quantifiable change of at least about 10%, at least about 20%, at least about 30%, at least about 50%, at least about 70%, or at least about 90%. In some embodiments, the effect will result in a quantifiable change of about 10%, about 20%, about 30%, about 50%, about 70%, or even about 90% or more. Therapeutic benefit also includes halting or slowing the progression of a contemplated underlying disease or disorder, regardless of whether improvement is realized.

Compounds of Formula I or a pharmaceutically acceptable salt thereof (and/or additional agents) described herein can be administered to a subject as a component of a composition that comprises a pharmaceutically acceptable carrier or vehicle. Such compositions can optionally comprise a suitable amount of a pharmaceutically acceptable carrier to provide the form for proper administration.

Pharmaceutically acceptable carriers can be liquids, such as water and oils, including those of petroleum, animal, vegetable, or synthetic origin, such as peanut oil, soybean oil, mineral oil, sesame oil and the like. The pharmaceutical excipients can be, for example, saline, gum acacia, gelatin, starch paste, talc, keratin, colloidal silica, urea and the like. In addition, auxiliary, stabilizing, thickening, lubricating, and coloring agents can be used. In some embodiments, the pharmaceutically acceptable excipients are sterile when administered to a subject. Water is a useful excipient when any agent described herein is administered intravenously. Saline solutions and aqueous dextrose and glycerol solutions can also be employed as liquid excipients, specifically for injectable solutions. Suitable pharmaceutical excipients also include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Any agent described herein, if desired, can also comprise minor amounts of wetting or emulsifying agents, or pH buffering agents.

Provided herein, in some embodiments, are methods for treating venous malformation or other congenital vascular malformations, comprising administering to a patient in need thereof an effective amount of a compound of Formula I or a pharmaceutically acceptable salt thereof. Contemplated venous malformations include glomuvenous malformations, mucocutaneous venous malformation (also cutaneomucosal venous malformation, VMCM), blue rubber bleb nevus syndrome, lesions in the stomach or gastrointestinal tract, and/or Maffucci syndrome.

For example, contemplated herein is a method of blocking growth of venous malformations which comprises administering to a patient in need thereof an effective amount of a compound of Formula I or a pharmaceutically acceptable salt thereof, for example, in a dosing regimen sufficient to block TIE2 kinase in the tumor microenvironment.

In some embodiments, the dosing regimen of the compound of Formula I or a pharmaceutically acceptable salt thereof is a daily or twice daily dosing administration.

In other embodiments, the dosing regimen of the compound of Formula I or a pharmaceutically acceptable salt thereof is an intermittent dosing administration. The intermittent non-daily dosing regimen may include, without limitation, alternate daily dosing, every third-day dosing, twice weekly dosing, or once weekly dosing. In some embodiments, the method comprises administering to the patient the compound of Formula I once daily, intermittent non-daily, every other day, every third day, every other week, twice daily, once weekly, or twice weekly.

In some embodiments, a suitable dosing regimen of the compound of Formula I or a pharmaceutically acceptable salt thereof includes administration twice weekly, once weekly, or alternate weekly, for example, twice weekly or once weekly, e.g. twice weekly.

Another aspect of the disclosure relates to a method of blocking venous malformation growth which comprises the administration of a compound of Formula I or a pharmaceutically acceptable salt thereof at doses sufficient to block TIE2 kinase or mutant TIE2 kinase activity, wherein the compound of Formula I or a pharmaceutically acceptable salt thereof is administered in an intermittent non-daily dosing regimen. In some embodiments, the intermittent non-daily dosing regimen, includes alternate daily dosing, every third daily dosing, twice weekly dosing, and once weekly dosing.

Another aspect of the disclosure relates to a method of treating venous malformation patients in a neoadjuvant setting prior to surgical resection of the tumor, comprising administering to a patient in need thereof and effective amount of a compound of Formula I, or a pharmaceutically acceptable salt thereof a dosing regimen of the compound of Formula I or a pharmaceutically acceptable salt thereof is sufficient to block TIE2 kinase or a mutant TIE2 kinase.

In some embodiments, the method of treating venous malformation patients in a neoadjuvant setting prior to surgical resection of tumor comprises administering to a patient in need thereof an effective amount of a compound of Formula I or a pharmaceutically acceptable salt thereof in a dosing regimen sufficient to block TIE2 kinase or a mutant TIE2 kinase.

In some embodiments, a method of treating venous malformation patients in a neoadjuvant setting prior to surgical resection comprises the administration of a compound of Formula I or a pharmaceutically acceptable salt thereof at doses sufficient to block TIE2 kinase or a mutant TIE2 kinase, with a dosing regimen of the compound of Formula I or a pharmaceutically acceptable salt thereof being administered daily or twice daily.

In some embodiments, the method of treating venous malformation patients in a neoadjuvant setting prior to surgical resection comprises administering to a patient in need thereof an effective amount of a compound of Formula I or a pharmaceutically acceptable salt thereof in a dosing regimen sufficient to block TIE2 kinase or a mutant TIE2 kinase, with a dosing regimen of the compound of Formula I or a pharmaceutically acceptable salt thereof administered in an intermittent non-daily manner, including alternate daily dosing, every third daily dosing, twice weekly dosing, or once weekly dosing.

In some embodiments, the method of treating venous malformation patients in a neoadjuvant setting prior to surgical resection comprises administering to a patient in need thereof an effective amount of a compound of Formula I or a pharmaceutically acceptable salt thereof in a dosing regimen administered twice weekly, once weekly, or alternate weekly.

Another aspect of this disclosure relates to a method of treating TIE2 kinase-mediated vascular anomalies or TIE2 kinase mutant-mediated vascular anomalies, (e.g., vascular malformations, vascular tumors (e.g., hemangiomas) and/or other congenital vascular defects) in a patient in need thereof, comprising administering to the patient a therapeutically effective amount of the compound of Formula I, or pharmaceutically acceptable salt thereof.

In some embodiments, the pharmaceutically acceptable salt is a sulfonate salt. In some embodiments, the pharmaceutically acceptable salt is a mesylate salt. In some embodiments, the pharmaceutically acceptable salt is a triflate salt. In some embodiments, the pharmaceutically acceptable salt is an esylate salt. In some embodiments, the pharmaceutically acceptable salt is a besylate salt. In some embodiments, the pharmaceutically acceptable salt is a closylate salt. In some embodiments, the pharmaceutically acceptable salt is a camsylate salt. In some embodiments, the pharmaceutically acceptable salt is tosylate. In some embodiments, the pharmaceutically acceptable salt is a mono-tosylate salt. In some embodiments, the pharmaceutically acceptable salt is a di-tosylate salt. In some embodiments, the pharmaceutically acceptable salt is a tri-tosylate salt. In some embodiments, the pharmaceutically acceptable salt is a tetra-tosylate salt.

Methods for treating vascular anomalies, in a patient in need thereof, are contemplated herein, comprising administering to the patient a therapeutically effective amount of the compound of Formula I, or a pharmaceutically acceptable salt thereof. In some embodiments, a vascular anomaly is a TIE2 kinase-mediated vascular anomaly or TIE2 kinase mutant-mediated vascular anomaly. A TIE2 kinase-mediated vascular anomaly or TIE2 kinase mutant-mediated vascular anomaly may be a slow-flow malformation. In some embodiments, slow-flow malformations are selected from capillary malformations, lymphatic malformations, lymphatic-venous malformations, or venous malformations. In some embodiments, the slow-flow malformations are venous malformations.

Formulations, Administration, Dosing, and Treatment Regimens

The present disclosure also describes the compound of Formula I (and/or additional agents) or a pharmaceutically acceptable salt thereof, in a pharmaceutical composition. A composition described herein can take the form of solutions, suspensions, emulsion, drops, tablets, pills, pellets, capsules, capsules containing liquids, powders, sustained-release formulations, suppositories, emulsions, aerosols, sprays, suspensions, or any other form suitable for use. In some embodiments, the composition is in the form of a capsule (see, e.g., U.S. Pat. No. 5,698,155). Other examples of suitable pharmaceutical excipients are described in *Remington's Pharmaceutical Sciences* 1447-1676 (Alfonso R. Gennaro eds., 19th ed. 1995), incorporated herein by reference.

Where necessary, the salts herein described can also include a solubilizing agent. Also, the agents can be delivered with a suitable vehicle or delivery device as known in the art. Combination therapies outlined herein can be co-delivered in a single delivery vehicle or delivery device. Compositions for administration can optionally include a local anesthetic such as, for example, lignocaine to lessen pain at the site of the injection.

In some embodiments, the compound of Formula I or a pharmaceutically acceptable salt thereof (and/or additional agents) described herein is formulated in accordance with routine procedures as a composition adapted for a mode of administration.

In certain embodiments, routes of administration include, for example: intradermal, intramuscular, intraperitoneal, intravenous, subcutaneous, intranasal, epidural, oral, sublingual, intranasal, intracerebral, intravaginal, transdermal, rectally, by inhalation, or topically, particularly to the ears, nose, eyes, or skin. In some embodiments, the administering is effected orally or by parenteral injection. The mode of administration can be left to the discretion of the practitioner, and depend in-part upon the site of the medical condition. In most instances, administration results in the release of any agent described herein into the bloodstream.

In some embodiments, it may be desirable to administer locally to the area in need of treatment or blocking.

In some embodiments, the salts (and/or additional agents) described herein is formulated in accordance with routine procedures as a composition adapted for oral administration to humans. Compositions for oral delivery can be in the form of tablets, lozenges, aqueous or oily suspensions, granules, powders, emulsions, capsules, syrups, or elixirs, for example. Orally administered compositions can comprise one or more agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions can be coated to delay disintegration and absorption in the gastrointestinal tract, thereby providing a sustained action over an extended period of time. Selectively permeable membranes surrounding an osmotically active driving the compound of Formula I or a pharmaceutically acceptable salt thereof (and/or additional agents) described herein are also suitable for orally administered compositions. In these latter platforms, fluid from the environment surrounding the capsule is imbibed by the driving composition, which swells to displace the agent or agent composition through an aperture. These delivery platforms can provide an essentially zero order delivery profile as opposed to the spiked profiles of immediate release formulations. A time-delay material such as glycerol monostearate or glycerol stearate can also be useful. Oral compositions can include standard excipients such as mannitol, lactose, starch, magnesium stearate, sodium saccharin, cellulose, and magnesium carbonate. In some embodiments, the excipients are of pharmaceutical grade. Suspensions, in addition to the active compositions, may contain suspending agents such as, for example, ethoxylated isostearyl alcohols, polyoxyethylene sorbitol and sorbitan esters, microcrystalline cellulose, aluminum metahydroxide, bentonite, agar-agar, tragacanth, etc., and mixtures thereof.

Dosage forms suitable for parenteral administration (e.g. intravenous, intramuscular, intraperitoneal, subcutaneous and intra-articular injection and infusion) include, for example, solutions, suspensions, dispersions, emulsions, and the like. They may also be manufactured in the form of sterile solid compositions (e.g. lyophilized composition), which can be dissolved or suspended in sterile injectable medium immediately before use. They may contain, for example, suspending or dispersing agents known in the art.

The dosage of the compound of Formula I or a pharmaceutically acceptable salt thereof (and/or additional agents) described herein as well as the dosing schedule can depend on various parameters, including, but not limited to, the disease being treated, the subject's general health, and the administering physician's discretion. Any agent described herein, can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concurrently with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of an additional therapeutic agent, to a subject in need thereof. In various embodiments any agent described herein is administered 1 minute apart, 10 minutes apart, 30 minutes apart, less than 1 hour apart, 1 hour apart, 1 hour to 2 hours apart, 2 hours to 3 hours apart, 3 hours to 4 hours apart, 4 hours to 5 hours apart, 5 hours to 6 hours apart, 6 hours to 7 hours apart, 7 hours to 8 hours apart, 8 hours to 9 hours apart, 9 hours to 10 hours apart, 10 hours to 11 hours apart, or 11 hours to 12 hours apart.

The dosage of the compound of Formula I or a pharmaceutically acceptable salt thereof (and/or additional agents) described herein can depend on several factors including the severity of the condition, whether the condition is to be treated or prevented, and the age, weight, and health of the subject to be treated. Additionally, pharmacogenomic (the effect of genotype on the pharmacokinetic, pharmacodynamic or efficacy profile of a therapeutic) information about a particular subject may affect dosage used. Furthermore, the exact individual dosages can be adjusted somewhat depending on a variety of factors, including the specific combination of the agents being administered, the time of administration, the route of administration, the nature of the formulation, the rate of excretion, the particular disease being treated, the severity of the disorder, and the anatomical location of the disorder. Some variations in the dosage can be expected.

In some embodiments, when orally administered to a mammal, the dosage of a compound of Formula I or a pharmaceutically acceptable salt thereof (and/or additional agents) described herein may be 0.001 mg/kg/day to 150 mg/kg/day, 0.001 mg/kg/day to 100 mg/kg/day, 0.01 mg/kg/day to 50 mg/kg/day, or 0.1 mg/kg/day to 10 mg/kg/day. In some embodiments, when orally administered to a human, the dosage of any agent described herein is normally 0.001 mg to 1500 mg per day, 1 mg to 600 mg per day, or 5 mg to 30 mg per day. In some embodiments, the dosage of the salt (or agent) ranges from 50 mg to 1200 mg per day. In some embodiments, the dosage of the salt (or agent) ranges from 50 mg to 900 mg per day. In some embodiments, the dosage of the salt (or agent) ranges from 50 mg to 600 mg per day. In some embodiments, the dosage of the salt (or agent) ranges from 50 mg to 300 mg per day. In some embodiments, the dosage of the salt (or agent) ranges from 50 mg to 150 mg per day. In some embodiments, the dosage of the salt (or agent) ranges from 50 mg to 140 mg per day. In some embodiments, the dosage of the salt (or agent) ranges from 50 mg to 130 mg per day. In some embodiments, the dosage of the salt (or agent) ranges from 50 mg to 120 mg per day. In some embodiments, the dosage of the salt (or agent) ranges from 50 mg to 110 mg per day. In some embodiments, the dosage of the salt (or agent) ranges from 50 mg to 100 mg per day. In some embodiments, the dosage of the salt (or agent) ranges from 50 mg to 90 mg per day. In some embodiments, the dosage of the salt (or agent) ranges from 57 mg to 1200 mg per day. In some embodiments, the dosage of the salt (or agent) ranges from 57 mg to 150 mg per day. In some embodiments, the dosage of the salt (or agent) ranges from 57 mg to 140 mg per day. In some embodiments, the dosage of the salt (or agent) ranges from 57 mg to 130 mg per day. In some embodiments, the dosage of the salt (or agent) ranges from 57 mg to 120 mg per day. In some embodiments, the dosage of the salt (or agent) ranges from 57 mg to 110 mg per day. In some embodiments, the dosage of the salt (or agent) ranges from 57 mg to 100 mg per day. In some embodiments, the dosage of the salt (or agent) ranges from 57 mg to 90 mg per day. In other embodiments, the dosage of the salt (or agent) or salt ranges from 60 mg to 200 mg per day. In other embodiments, the dosage of the salt (or agent) or salt ranges from 60 mg to 150 mg per day. In other embodiments, the dosage of the salt (or agent) or salt ranges from 70 mg to 150 mg per day. In other embodiments, the dosage of the salt (or agent) or salt ranges from 80 mg to 150 mg per day. In other embodiments, the dosage of the salt (or agent) or salt ranges from 90 mg to 150 mg per day. In other embodiments, the dosage of the salt (or agent) or salt ranges from 100 mg to 150 mg per day. In other embodiments, the dosage of the salt (or agent) or salt ranges from 100 mg to 200 mg per day.

In some embodiments, for administration of the compound of Formula I or a pharmaceutically acceptable salt thereof (and/or additional agents) described herein by parenteral injection, the dosage is 0.1 mg to 250 mg per day. In some embodiments, the dosage is 1 mg to 200 mg per day. In some embodiments, the dosage is 1 mg to 150 mg per day. In some embodiments, the dosage is 10 mg to 150 mg per day. In some embodiments, the dosage is 20 mg to 200 mg per day. In some embodiments, the dosage is 30 mg to 200 mg per day. In some embodiments, the dosage is 40 mg to 200 mg per day. In some embodiments, the dosage is 50 mg to 200 mg per day. In some embodiments, the dosage is 50 mg to 150 mg per day. In some embodiments, the dosage is 57 mg to 150 mg per day. In some embodiments, the dosage is 57 mg to 100 mg per day. In some embodiments, the dosage is 60 mg to 150 mg per day. In some embodiments, the dosage is 70 mg to 150 mg per day. In some embodiments, the dosage is 60 mg to 140 mg per day. In some embodiments, the dosage is 60 mg to 130 mg per day. In some embodiments, the dosage is 60 mg to 120 mg per day. In some embodiments, the dosage is 60 mg to 110 mg per day. In some embodiments, the dosage is 60 mg to 100 mg per day. In some embodiments, the dosage is 60 mg to 90 mg per day. In some embodiments, the dosage is 70 mg to 130 mg per day. In some embodiments, the dosage is 70 mg to 120 mg per day. In some embodiments, the dosage is 70 mg to 110 mg per day. In some embodiments, the dosage is 70 mg to 100 mg per day. In some embodiments, the dosage is 1 mg to 20 mg per day, or 3 mg to 5 mg per day. Injections may be given up to four times daily. In some embodiments, when orally or parenterally administered, the dosage of any agent described herein is normally 0.1 mg to 1500 mg per day, or 0.5 mg to 10 mg per day, or 0.5 mg to 5 mg per day. A dosage of up to 3000 mg per day can be administered.

In some embodiments, administration of the salts (and/or additional agents) described herein can, independently, be one to four times daily. Specifically, administration of the salt can be once a day at a dosing regimen of the salt is from about 50 mg to 1500 mg. Suitable daily dosage for the prophylactic effects sought is 57-1200 mg/day. In some embodiments, the methods described herein comprise administering to the patient about 100 mg of the compound of Formula I or a pharmaceutically acceptable salt thereof daily. In some embodiments, the methods described herein comprise administering to the patient about 200 mg of the compound of Formula I or a pharmaceutically acceptable salt thereof daily. In some embodiments, the methods described herein comprise administering to the patient about 300 mg of the compound of Formula I or a pharmaceutically acceptable salt thereof daily. If administered twice daily, a suitable dosage is 100 mg to 200 mg of the salt. In some embodiments, the methods described herein comprise administering to the patient about 150, 200, or 300 mg of the compound of Formula I or a pharmaceutically acceptable salt thereof once or twice daily. In some other embodiments, administration of the salt may also be intermittently non-daily. In some embodiments, administration of the salt may be done one to four times per month or one to six times per year or once every two, three, four or five years. In certain embodiments administration of the salt is done weekly or bi-weekly. In some embodiments, administration of the salt is weekly or bi-weekly, In some embodiments, a suitable salt dosing regimen ranges from 50-200 mg/per administration. In some embodiments, administrations are weekly or bi-weekly and the dosage is 200-400 mg/per administration. In some embodiments, administrations are weekly or bi-weekly administrations and the dosage is 400-500 mg/per administration. In some embodiments, administrations are weekly or bi-weekly administrations and the dosage is 500-600 mg/per administration. In some embodiments, administrations are weekly or bi-weekly administrations and the dosage is 600-700 mg/per administration. In some embodiments, administrations are weekly or bi-weekly administrations and the dosage is 700-800 mg/per administration. In some embodiments, administrations are weekly or bi-weekly administrations and the dosage is 800-900 mg/per administration. In some embodiments, administrations are weekly or bi-weekly administrations and the dosage is 900-1000 mg/per administration. In some embodiments, administrations are weekly or bi-weekly administrations and the dosage is 1000-1100 mg/per administration. In some embodiments, administrations are weekly or bi-weekly administrations and the dosage is 1100-1200 mg per administration. Administration can be for the duration of one day or one month, two months, three months, six months, one year, two years, three years, and may even be for the life of the subject. Chronic, long-term administration will be indicated in many cases. The dosage may be administered as a single dose or divided into multiple doses. In general, the desired dosage should be administered at set intervals for a prolonged period, usually at least over several weeks or months, although longer periods of administration of several months or years or more may be needed.

In some embodiments, the compound of Formula I or a pharmaceutically acceptable salt thereof may be administered to the patient as a single agent or in combination with other therapeutic agents. Such other therapeutic agents include radiation therapy, anti-tubulin agents, DNA alkylating agents, DNA synthesis-inhibiting agents, DNA intercalating agents, anti-estrogen agents, anti-androgens, steroids, anti-EGFR agents, kinase inhibitors, topoisomerase inhibitors, Histone Deacetylase (HDAC) inhibitors, DNA methylation inhibitors, anti-HER2 agents, anti-angiogenic agents, proteasome inhibitors, thalidomide, lenalidomide, antibody-drug-conjugates (ADCs), immunomodulating agents, or cancer vaccines. In some embodiments, the compound of Formula I or a pharmaceutically acceptable salt thereof may be administered to the patient in combination with a VEGF inhibitor. In some embodiments, the compound of Formula I or a pharmaceutically acceptable salt thereof may be administered to the patient in combination with an Akt inhibitor. In some embodiments, the compound of Formula I or a pharmaceutically acceptable salt thereof may be administered to the patient in combination with a mTOR inhibitor. In some embodiments, the compound of Formula I or a pharmaceutically acceptable salt thereof may be administered to the patient in combination with a PI3K inhibitor.

When the compound of Formula I, or pharmaceutically acceptable salts thereof, are used in combination with other agents, the other agent may be dosed independently of the dosing schedule of the compound of Formula I. The other agent may be dosed at its previously established therapeutic dose and dosing schedule, or its dose and dosing schedule may be modified to optimize efficacy, safety or tolerability when used in combination with the compound of Formula I.

The compound of Formula I or pharmaceutically acceptable salts thereof may be used in combination with other agents including but not limited to chemotherapeutic agents, targeted therapeutics, biological agents, or radiotherapy.

In some embodiments, the compound of Formula I or pharmaceutically acceptable salts thereof may be used in combination with chemotherapeutic agents including but not limited to anti-tubulin agents (e.g., paclitaxel, paclitaxel protein-bound particles for injectable suspension, eribulin, docetaxel, ixabepilone, vincristine, vinorelbine, epothilones, halichondrins, maytansinoids), DNA-alkylating agents (e.g., cisplatin, carboplatin, oxaliplatin, cyclophosphamide, ifosfamide, temozolomide), DNA intercalating agents (e.g., doxorubicin, pegylated liposomal doxorubicin, daunorubicin, idarubicin, and epirubicin), 5-fluorouracil, capecitabine, cytarabine, decitabine, 5-aza cytadine, gemcitabine and methotrexate.

In some embodiments, the compound of Formula I or pharmaceutically acceptable salts thereof may be used in combination with kinase inhibitors including but not limited to erlotinib, gefitinib, lapatanib, everolimus, sirolimus, temsirolimus, LY2835219, LEEOl 1, PD 0332991, crizotinib, cabozantinib, sunitinib, pazopanib, sorafenib, regorafenib, axitinib, dasatinib, imatinib, nilotinib, vemurafenib, dabrafenib, trametinib, idelalisib, duvelisib, alpelisib, copanlisib, and quizartinib.

In some embodiments, the compound of Formula I or pharmaceutically acceptable salts thereof may be used in combination with anti-estrogen agents including but not limited to tamoxifen, fulvestrant, anastrozole, letrozole, and exemestane.

In some embodiments, the compound of Formula I or pharmaceutically acceptable salts thereof may be used in combination with anti-androgen agents including but not limited to abiraterone acetate, enzalutamide, nilutamide, bicalutamide, flutamide, cyproterone acetate.

In some embodiments, the compound of Formula I or pharmaceutically acceptable salts thereof may be used in combination with steroid agents including but not limited to prednisone and dexamethazone.

In some embodiments, the compound of Formula I or pharmaceutically acceptable salts thereof may be used in combination with topoisomerase I inhibitors including but not limited to irinotecan, camptothecin, and topotecan.

In some embodiments, the compound of Formula I or pharmaceutically acceptable salts thereof may be used in combination with topoisomerase II inhibitors including but not limited to etoposide, etoposide phosphate, and mitoxantrone.

In some embodiments, the compound of Formula I or pharmaceutically acceptable salts thereof may be used in combination with Histone Deacetylase (HDAC) inhibitors including but not limited to vorinostat, romidepsin, panobinostat, valproic acid, and belinostat.

In some embodiments, the compound of Formula I or pharmaceutically acceptable salts thereof may be used in combination with DNA methylation inhibitors including but not limited to DZNep and 5-aza-2'-deoxycytidine.

In some embodiments, the compound of Formula I or pharmaceutically acceptable salts thereof may be used in combination with proteasome inhibitors including but not limited to bortezomib and carfilzomib.

In some embodiments, the compound of Formula I or pharmaceutically acceptable salts thereof may be used in combination with thalidomide, lenalidomide and pomalidomide.

In some embodiments, the compound of Formula I or pharmaceutically acceptable salts thereof may be used in combination with biological agents including but not limited to trastuzumab, ado-trastuzumab, pertuzumab, cetuximab, panitumumab, ipilimumab, anti-PD-1 agents including but not limited to labrolizumab and nivolumab, anti-PD-L1 agents including but not limited to MPDL3280A, anti-angiogenic agents including but not limited to bevacizumab and aflibercept, and antibody-drug-conjugates (ADCs) including but not limited to brentuximab vedotin, trastuzumab deruxtecan (DS-8201) and trastuzumab emtansine.

In some embodiments, the compositions comprising the compound of Formula I or a pharmaceutically acceptable salt thereof may be used in combination with radiotherapy.

In some embodiments, the compound of Formula I or pharmaceutically acceptable salts thereof may be used in combination with therapeutic vaccines including but not limited to sipuleucel-T.

In some embodiments, the compound of Formula I or pharmaceutically acceptable salts thereof may be used in combination with VEGF inhibitors including but not limited to pazopanib, bevacizumab, cabozantinib, sunitinib, sorafenib, axitinib, regorafenib, ponatinib, cabozantinib, vandetanib, ramucirumab, lenvatinib, bevacizumab, and ziv-aflibercept.

In some embodiments, the compound of Formula I or pharmaceutically acceptable salts thereof may be used in combination with Akt inhibitors including but not limited to AZD5363, miltefosine, perifosine, VQD-002, MK-2206, GSK690693, GDC-0068, triciribine, CCT128930, PHT-427, and honokiol.

In some embodiments, the compound of Formula I or pharmaceutically acceptable salts thereof may be used in combination with mTOR inhibitors including but not limited to sirolimus, temsirolimus, everolimus, AP23841, AZD8055, BEZ235, BGT226, deferolimus (AP23573/MK-8669), EM101/LY303511, EX2044, EX3855, EX7518, GDC0980, INK-128, KU-0063794, NV-128, OSI-027, PF-4691502, rapalogs, rapamycin, ridaforolimus, SAR543, SF1126, WYE-125132, XL765, zotarolimus (ABT578), torin 1, GSK2126458, AZD2014, GDC-0349, and XL388.

In some embodiments, the compound of Formula I or pharmaceutically acceptable salts thereof may be used in combination with PI3K inhibitors including but not limited to idelalisib, copanlisib, duvelisib, alpelisib, NVP-BEZ235, BKM-120, GDC-0941, GDC-0980, SF1126, PX-866, PF-04691502, XL-765, XL-147, GSK2126458, and ZSTK474.

In some embodiments, the compound of Formula I or pharmaceutically acceptable salts thereof can be used in combination with one or more of the other agents described herein.

EXAMPLES

The present disclosure is not to be limited in scope by the specific embodiments disclosed in the examples which are intended as illustrations of a few aspects of the disclosure and any embodiments that are functionally equivalent are within the scope of this disclosure. Indeed, various modifications in addition to those shown and described herein will become apparent to those skilled in the art and are intended to fall within the scope of the appended claims.

Example 1. Biochemical Inhibition of R849W TIE2 Mutant by the Compound of Formula I Biochemical Assay for R849W TIE2 (Seq. ID No. 1)

Activity of R849W TIE2 kinase was determined by following the production of ADP from the kinase reaction through coupling with the pyruvate kinase/lactate dehydrogenase system (e.g., Schindler et al. Science (2000) 289: 1938-1942). In this assay, the oxidation of NADH (thus the decrease at $A_{340\ nm}$) was continuously monitored spectrophotometrically. The reaction mixture (100 μL) contained R849W TIE2 (SignalChem) (7.5 nM), BSA (0.004% (w/v)), polyEY (1 mg/ml), $MgCl_2$ (15 mM), DTT (0.5 mM), pyruvate kinase (4 units), lactate dehydrogenase (7 units), phosphoenol pyruvate (1 mM), and NADH (0.28 mM) and ATP (4 mM) in 100 mM Tris buffer containing 0.2% octyl-glucoside and 1% DMSO, pH 7.5. The inhibition reaction was started by mixing serial diluted test compound with the above reaction mixture. The absorption at 340 nm was monitored continuously for 8 hours at 30° C. on a plate reader (BioTek). The reaction rate was calculated using the 3 to 4 h time frame. Percent inhibition was obtained by comparison of reaction rate with that of a control (i.e. with no test compound). $IC_{50}$ values were calculated from a series of percent inhibition values determined at a range of inhibitor concentrations using software routines as implemented in the GraphPad Prism software package. The compound of Formula I disclosed herein exhibited an $IC_{50}$ value of 0.9 nM.

R849W TIE2 Protein Sequence Used for Screening (Seq. ID No. 1)

```
QLKRANVQRRMAQAFQNVREEPAVQFNSGTLALNRKVKNNPDPTIYPVLD
WNDIKEQDVIGEGNFGQVLKARIKKDGLWMDAAIKRMKEYASKDDHRDFA
GELEVLCKLGHHPNIINLLGACEHRGYLYLAIEYAPHGNLLDFLRKSRVL
ETDPAFAIANSTASTLSSQQLLHFAADVARGMDYLSQKQFIHRDLAARNI
LVGENYVAKIADFGLSRGQEVYVKKTMGRLPVRWMAIESLNYSVYTTNSD
VWSYGVLLWEIVSLGGTPYCGMTCAELYEKLPQGYRLEKPLNCDDEVYDL
MRQCWREKPYERPSFAQILVSLNRMLEERKTYVNTTLYEKFTYAGIDCSA
EEAA
```

Example 2. Biochemical Inhibition a Panel of TIE2 Mutants by the Compound of Formula I Biochemical Assay a Panel of TIE2 Mutants and WT TIE2

TIE2 WT or TIE2 mutants (R849W, P883A, Y897C, Y897S, Y1108F, or A1124V) and polyEY substrate were added to reaction buffer (20 mM Hepes pH 7.5, 10 mM $MgCl_2$, 2 mM $MnCl_2$, 1 mM EGTA, 0.02% Brij35, 0.02 mg/ml BSA, 0.1 mM $Na_3VO_4$, 2 mM DTT, 1% DMSO). Compound 1 was added into the reaction, followed 20 min later by the addition of a mixture of ATP and $^{33}P$ ATP to a final concentration of 10 μM. Reactions were carried out at 25° C. for 2 hr. Reactions were spotted onto P81 ion exchange filter paper and unbound phosphate was washed out of filters in 0.75% phosphoric acid. After subtraction of background derived from control reactions containing inactive enzyme, kinase activity data were expressed as the percent remaining kinase activity in test samples compared to DMSO control reactions. $IC_{50}$ values were calculated from a series of percent inhibition values determined at a range of inhibitor concentrations using software routines as implemented in the GraphPad Prism software package. The compound of Formula I disclosed herein exhibited $IC_{50}$ values of 0.97 nM for WT TIE2, 1.3 nM for R849W TIE2, 8.1 nM for P883A TIE2, 1.2 nM for Y897C TIE2, 1.5 nM for Y897S TIE2, 8.4 nM for Y1108F TIE2, and 2.7 nM for A1124V TIE2.

Example 3. Cellular Inhibition of TIE2 Mutants in CHO Cells by the Compound of Formula I CHO K1 Cell Culture CHO-K1 cells (catalog #CCL-61) were obtained from the American Type Culture Collection (ATCC, Manassas, VA). Briefly, cells were grown in RPMI 1640 medium supplemented with 10% characterized fetal bovine serum (Invitrogen, Carlsbad, CA), 100 units/mL penicillin G, 100 μg/ml streptomycin, and 0.29 mg/mL L-glutamine (Invitrogen, Carlsbad, CA) at 37 degrees Celsius, 5% $CO_2$, and 95% humidity. Cells were allowed to expand until reaching 70-95% confluence at which point they were subcultured or harvested for assay use.

Mutant TIE2-Transfected CHO K1 Phospho-TIE2 Western Blot Assay

CHO K1 cells ($1\times10^5$ cells/well) were added to a 24-well tissue-culture treated plate in 1 mL of RPMI1640 medium supplemented with 10% characterized fetal bovine serum and 1× non-essential amino acids (Invitrogen, Carlsbad, CA). Cells were then incubated overnight at 37 degrees Celsius, 5% $CO_2$, and 95% humidity. Medium was aspirated, and 0.5 mL of medium was added to each well. Transfection-grade plasmid DNA encoding TIE2 mutants R849W, L914F, R1099*, Y897C/R915C, or Y897F/R915L (TIE2 gene Gateway cloned into pcDNA3.2™/V5-DEST expression vector, Invitrogen, Carlsbad, CA) was diluted to 5 μg/mL in room temperature Opti-MEM® I Medium without serum (Invitrogen, Carlsbad, CA). Two μL of Lipofectamine LTX Reagent (Invitrogen, Carlsbad, CA) was added per 0.5 of plasmid DNA. The tube was mixed gently and incubated for 25 minutes at room temperature to allow for DNA-Lipofectamine LTX complex formation. 100 μL of the DNA-Lipofectamine LTX complex was added directly to each well containing cells and mixed gently. Twenty-four hours post-transfection, medium containing DNA-Lipofectamine complexes was aspirated, cells were washed with serum-free RPMI 1640, and serum-free RPMI1640 medium was added. Test compound or DMSO was added to the wells (0.5% final DMSO concentration). The plates were then incubated for 4 hours at 37 degrees Celsius, 5% $CO_2$, and 95% humidity. Following the incubation, the media was aspirated and the cells were washed with PBS. The cells were lysed using MPER lysis buffer (Pierce, Rockford, IL) containing Halt Phosphatase and Protease Inhibitors (Pierce, Rockford, IL) and Phosphatase inhibitor cocktail 2 (Sigma, St. Louis, MO) at 4° C. for 10 minutes with shaking. Cleared lysates were separated by SDS-PAGE on a 4-12% Novex NuPage Bis-Tris gel (Invitrogen, Carlsbad, CA) and then transferred to Immobilon-FL PVDF. After transfer, the PVDF membrane was blocked with Odyssey Blocking Buffer (Li-cor, Lincoln, NE) and then probed with a rabbit antibody for phospho-TIE2 (EMD Millipore, Burlington, MA) and a mouse anti-TIE2 antibody (BD Pharmingen, San Jose, CA). A secondary goat anti-rabbit antibody conjugated to a near-infrared dye with emission wavelength of 800 nm (Li-cor, Lincoln, NE) was used to detect phospho-TIE2. A secondary goat anti-mouse antibody conjugated to a near-infrared dye with emission wavelength of 680 nm (Li-cor, Lincoln, NE) was used to detect total TIE2. Fluorescence was detected using an Odyssey CL imager (Li-cor, Lincoln, NE). The 160 kDa phospho-TIE2 and total TIE2 bands were quantified using Image Studio software (Li-cor, Lincoln, NE). Data was analyzed using Prism software (GraphPad Software, San Diego, CA) to calculate $IC_{50}$ values. The compound of Formula I disclosed herein exhibited the following $IC_{50}$ values: 3.6 nM for R849W TIE2, 0.58 nM for L914F TIE2, 0.41 nM for R1099* TIE2, 1.2 nM for Y897C/R915C TIE2, and 0.35 nM for Y897F/R915L TIE2 (FIG. A-E).

Example 4. Cellular Inhibition of TIE2 Mutants in Human Umbilical Vein Endothelial Cells by the Compound of Formula I Human Umbilical Vein Endothelial Cell (HUVEC) Culture HUVECs used for in vitro work were kindly provided by Dr. Lauri Eklund (Oulu, Finland). Briefly, cells were grown in endothelial cell growth media (Tebu-Bio, Boechout, Belgium) containing 10% fetal calf serum (Sigma-Aldrich, Diegem, Belgium) at 37 degrees Celsius, 5% $CO_2$, and 95% humidity. Cells were allowed to expand until reaching 90-95% confluence at which point they were subcultured or harvested for assay use.

Mutant TIE2-Transfected HUVEC Western Blot Assay

Figure 2:
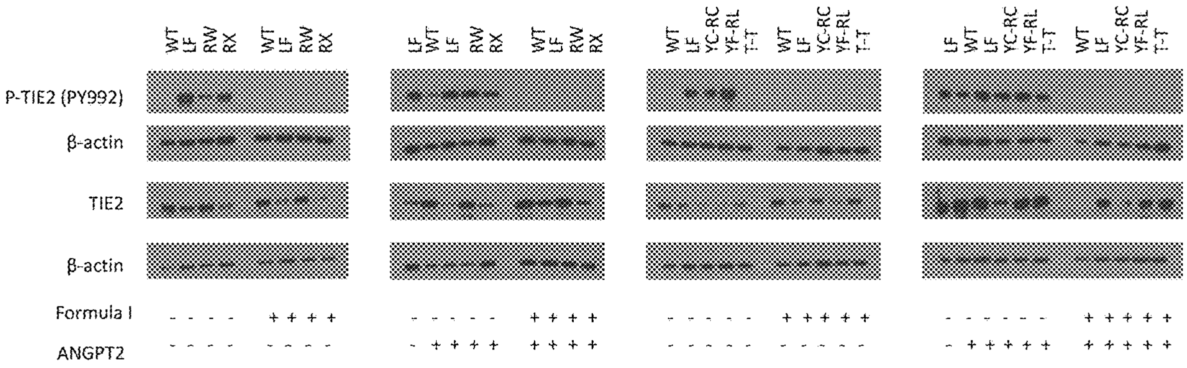
FIG. 2 shows the inhibition of phosphorylation of various mutant forms of TIE2 using the compound of Formula I in assays using transfected human umbilical vein endothelial cells
Figure 3:
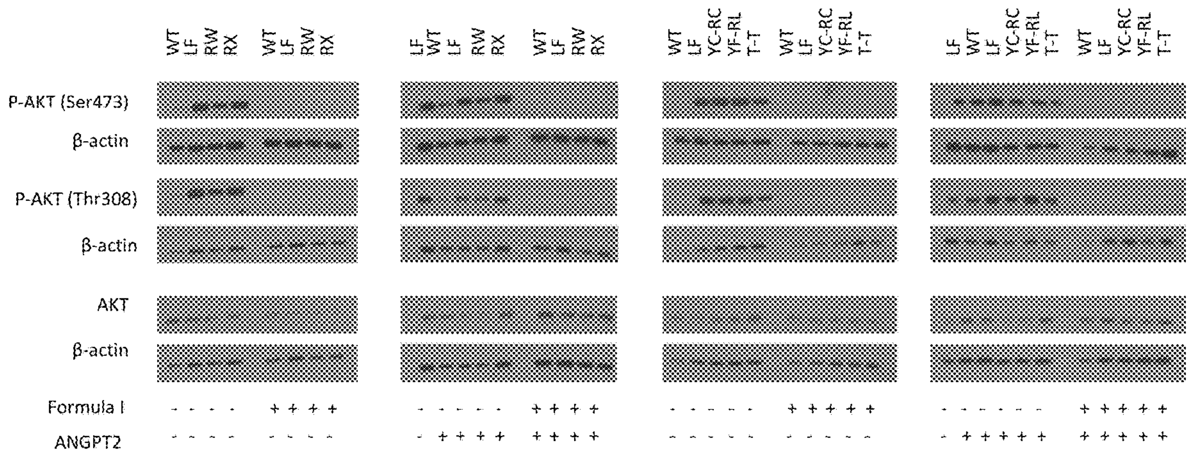
FIG. 3 shows the inhibition of phosphorylation of downstream signaling protein AKT using the compound of Formula I in assays using transfected human umbilical vein endothelial cells with various mutant forms of TIE2.
Figure 4:
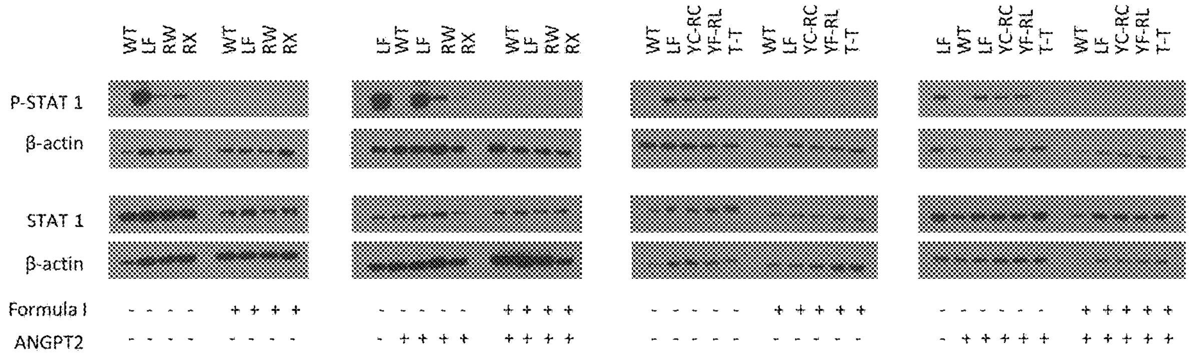
FIG. 4 shows the inhibition of phosphorylation of downstream signaling protein STAT1 using the compound of Formula I in assays using transfected human umbilical vein endothelial cells with various mutant forms of TIE2.

HUVEC cells ($2.5\times10^5$ cells/well) stably expressing WT or TIE2 mutants R849W, L914F, R1099*, Y897C/R915C, Y897F/F915L, or T1105N/T1106P were added to a 6-well plate coated with attachment factor solution (Tebu-Bio, Boechout, Belgium) in 2 mL of endothelial cell growth media (Tebu-Bio, Boechout, Belgium) containing 10% fetal calf serum (Sigma-Aldrich, Diegem, Belgium). Cells were subsequently incubated overnight at 37 degrees Celsius, 5% $CO_2$, and 95% humidity. The next day test compound or DMSO was added to the wells (0.068% final DMSO concentration). The plates were then incubated for 4 hours at 37 degrees Celsius, 5% $CO_2$, and 95% humidity. Next, cells were stimulated with 1 μg/mL ANGPT1 for 15 minutes. Cells were lysed and pTIE2, TIE2, b-actin, pAKT (S473), pAKT (T308), AKT, pSTAT1, and STAT1 were detected by Western blot. The compound of Formula I disclosed herein at a concentration of 100 nM exhibited complete inhibition of TIE2 phosphorylation in HUVECs with WT TIE2 and TIE2 mutants both in the presence or absence of stimulation with ANGPT1 (FIG. 2). The compound of Formula I disclosed herein at a concentration of 100 nM exhibited complete inhibition of AKT Ser473 and Thr308 phosphorylation downstream of TIE2 in HUVECs with WT TIE2 and TIE2 mutants both in the presence or absence of stimulation with ANGPT1 (FIG. 3). The compound of Formula I disclosed herein at a concentration of 100 nM exhibited complete inhibition of STAT1 phosphorylation downstream of TIE2 in HUVECs with WT TIE2 and TIE2 mutants both in the presence or absence of stimulation with ANGPT1 (FIG. 4).

Figure 5A:
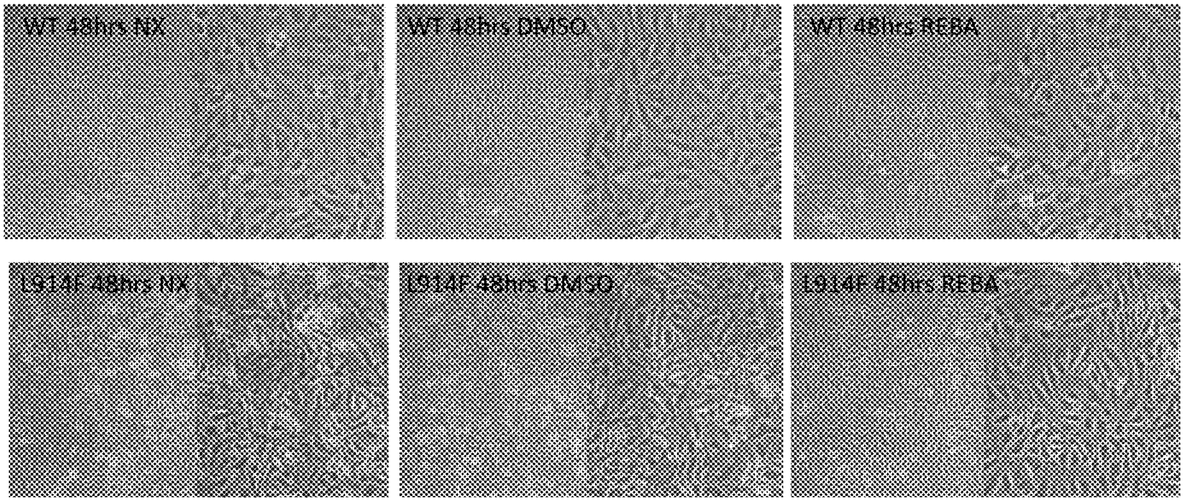
FIGS. 5A-F shows the restoration of cellular morphology using the compound of Formula I in assays using transfected human umbilical vein endothelial cells with various mutant forms of TIE2 (WT or L914F, R849W, R1099*, Y897C/R915C, Y897C/R915L, and T1105N/T1106P, respectively).
Figure 5B:
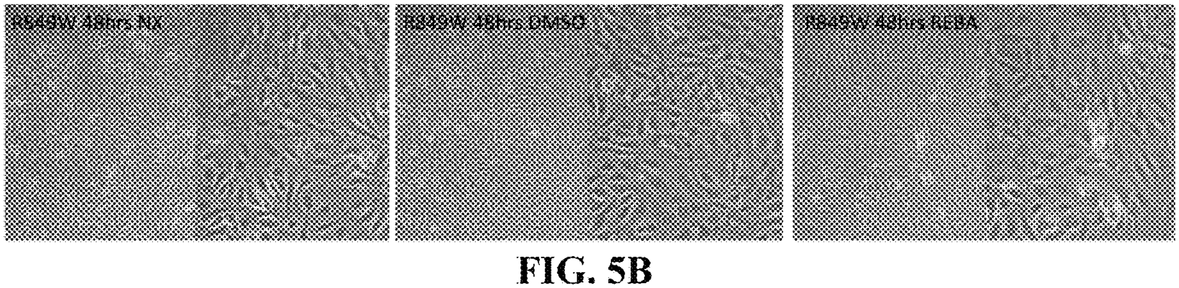
Figure 5C:
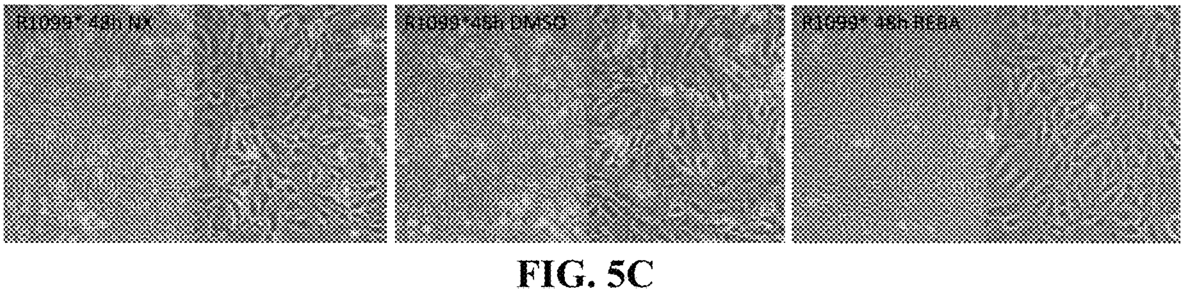
Figure 5D:
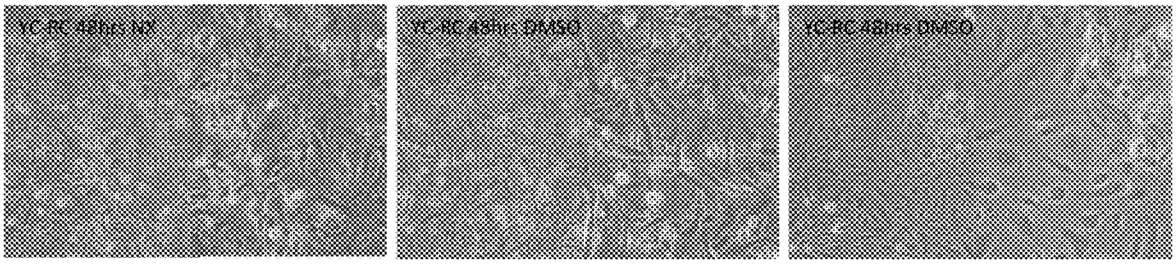
Figure 5E:
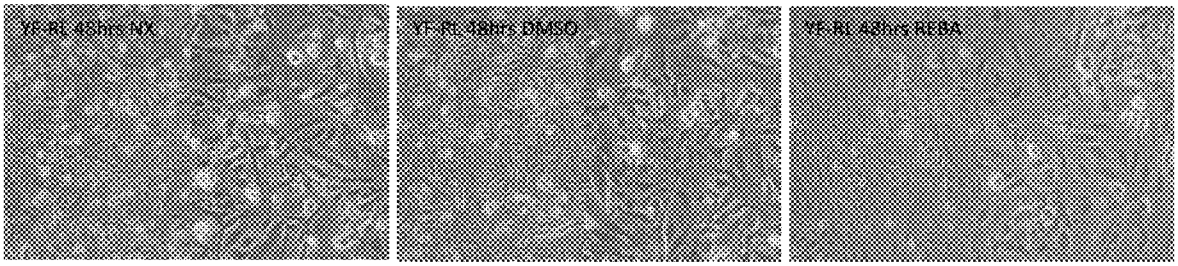
Figure 5F:
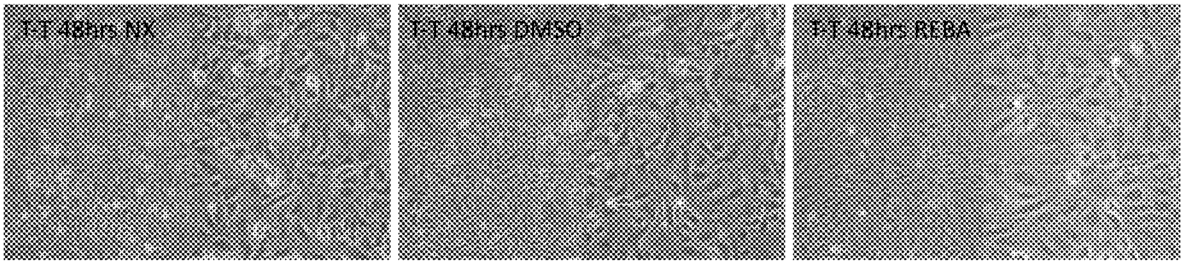

Example 5. Restoration of Cellular Morphology of TIE2 Mutant Human Umbilical Vein Endothelial Cells by the Compound of Formula I Mutant TIE2-Transfected HUVEC Cell Morphology Assay HUVEC cells ($5\times10^5$ cells/plate) stably expressing WT or TIE2 mutants R849W, L914F, R1099*, Y897C/R915C, Y897F/F915L, or T1105N/T1106P were added to a 10 cm plate coated with attachment factor solution (Tebu-Bio, Boechout, Belgium) in 6 mL of endothelial cell growth media (Tebu-Bio, Boechout, Belgium) containing 10% fetal calf serum (Sigma-Aldrich, Diegem, Belgium). Cells were then incubated for 2 days at 37 degrees Celsius, 5% $CO_2$, and 95% humidity. Next, test compound or DMSO was added to the wells (0.068% final DMSO concentration). The plates were then further incubated for 48 hours at 37 degrees Celsius, 5% $CO_2$, and 95% humidity. The cells were imaged by microscopy at 24 hours and 48 hours after addition of compound. The compound of Formula I disclosed herein at a concentration of 100 nM restored cellular morphology in TIE2 mutant HUVECs comparably to HUVECs expressing WT TIE2. FIG. 5A shows HUVECs expressing WT TIE2 or L914F TIE2 after 48 hours with no treatment, with DMSO control treatment, or with 100 nM compound treatment. FIG. 5B shows HUVECs expressing R849W TIE2 after 48 hours with no treatment, with DMSO control treatment, or with 100 nM compound treatment. FIG. 5C shows HUVECs expressing R1099* TIE2 after 48 hours with no treatment, with DMSO control treatment, or with 100 nM compound treatment. FIG. 5D shows HUVECs expressing Y897C/R915C TIE2 after 48 hours with no treatment, with DMSO control treatment, or with 100 nM compound treatment. FIG. 5E shows HUVECs expressing Y897C/R915L TIE2 after 48 hours with no treatment, with DMSO control treatment, or with 100 nM compound treatment. FIG. 5F shows HUVECs expressing T1105N/T1106P TIE2 after 48 hours with no treatment, with DMSO control treatment, or with 100 nM compound treatment.

Figure 6A:
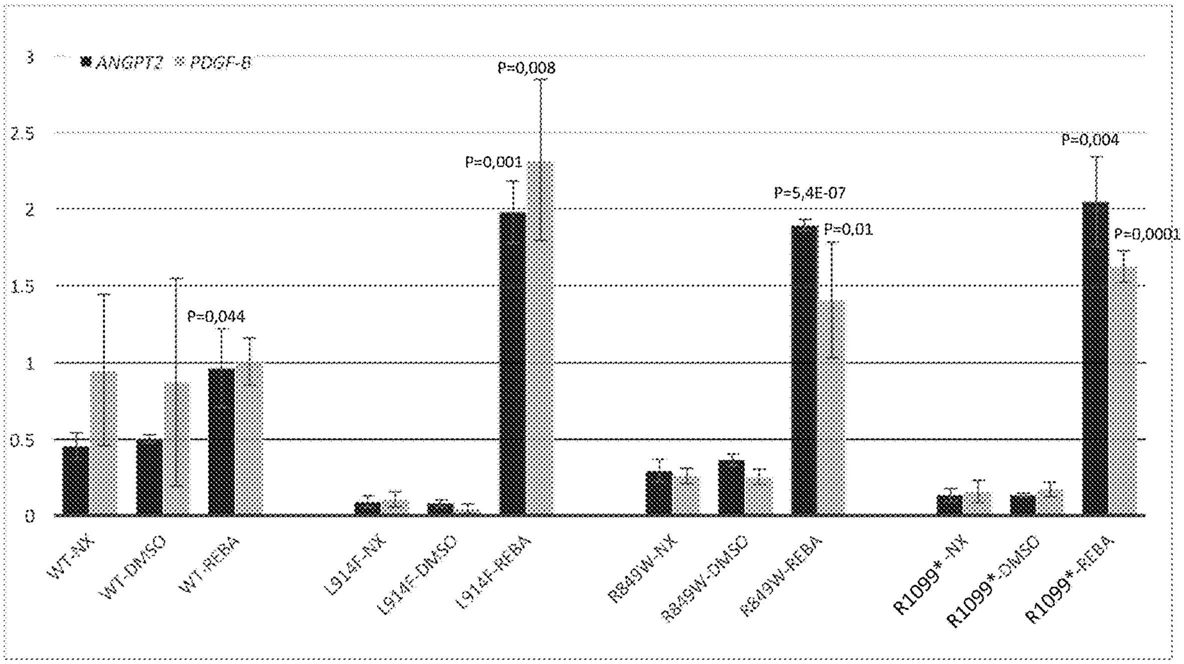
FIG. 6A-F shows the effects on expression of ANGPT2, PDGFB, ADAMTS1, ADAMTS9, PLAT and PLAU using the compound of Formula I in assays using transfected human umbilical vein endothelial cells with various mutant forms of TIE2.
Figure 6B:
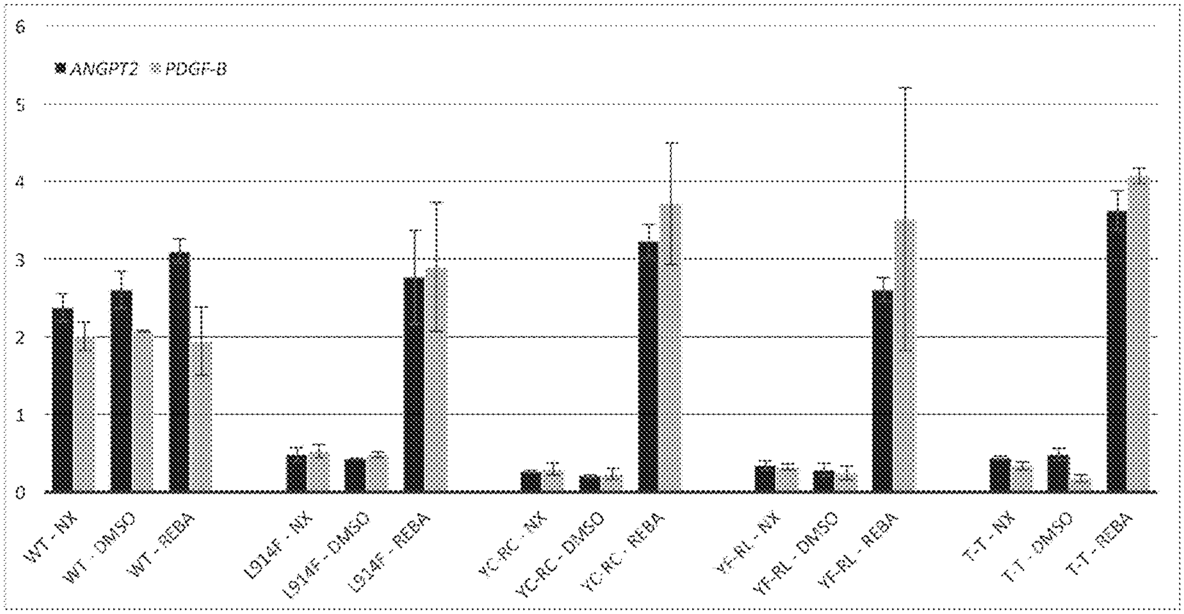
Figure 6C:
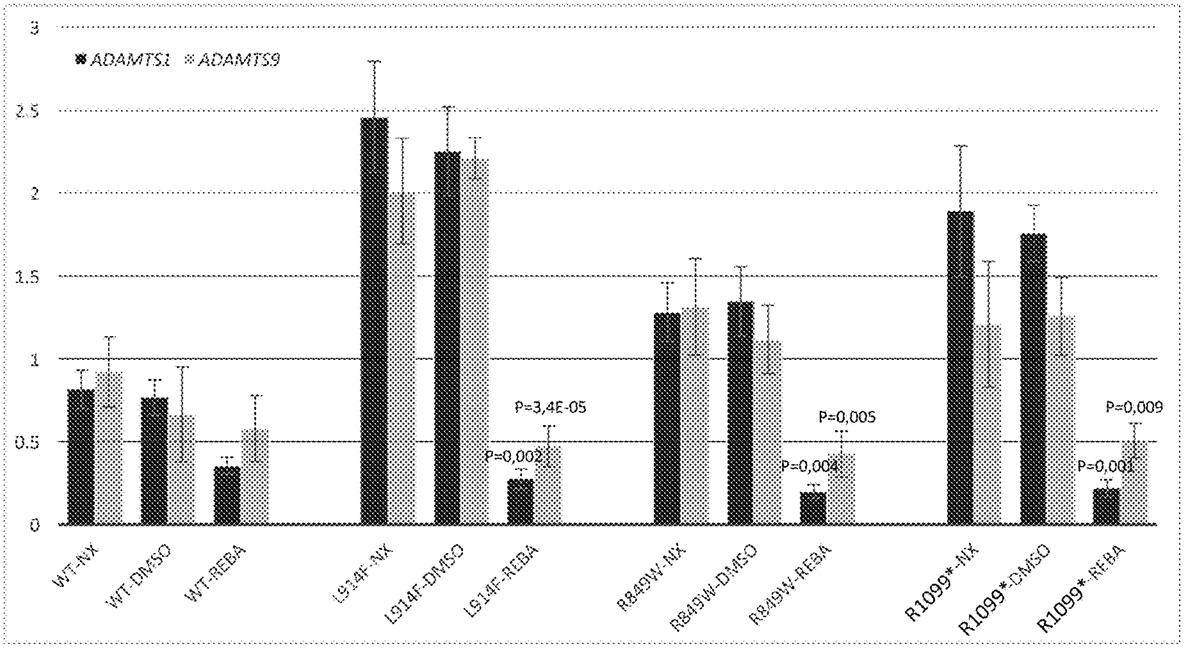
Figure 6D:
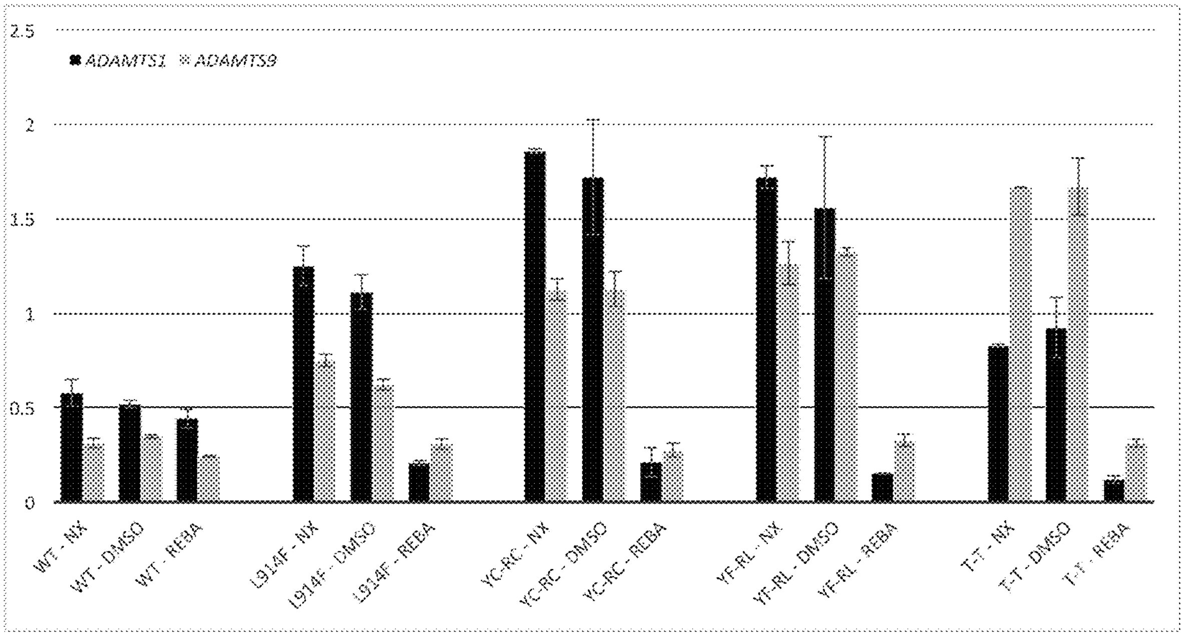
Figure 6E:
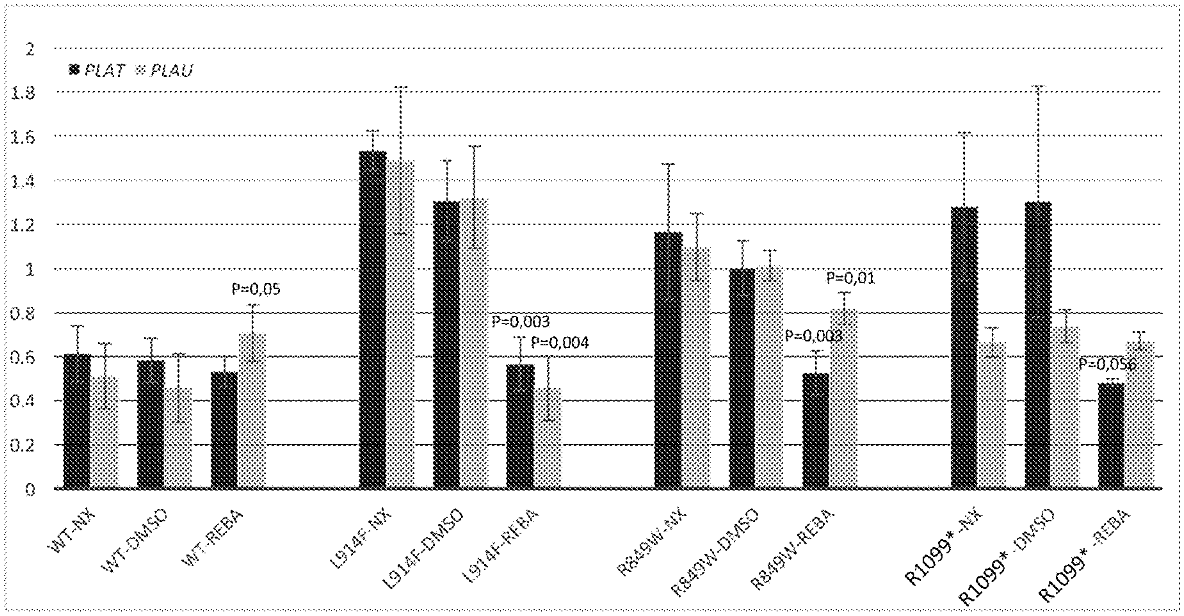
Figure 6F:
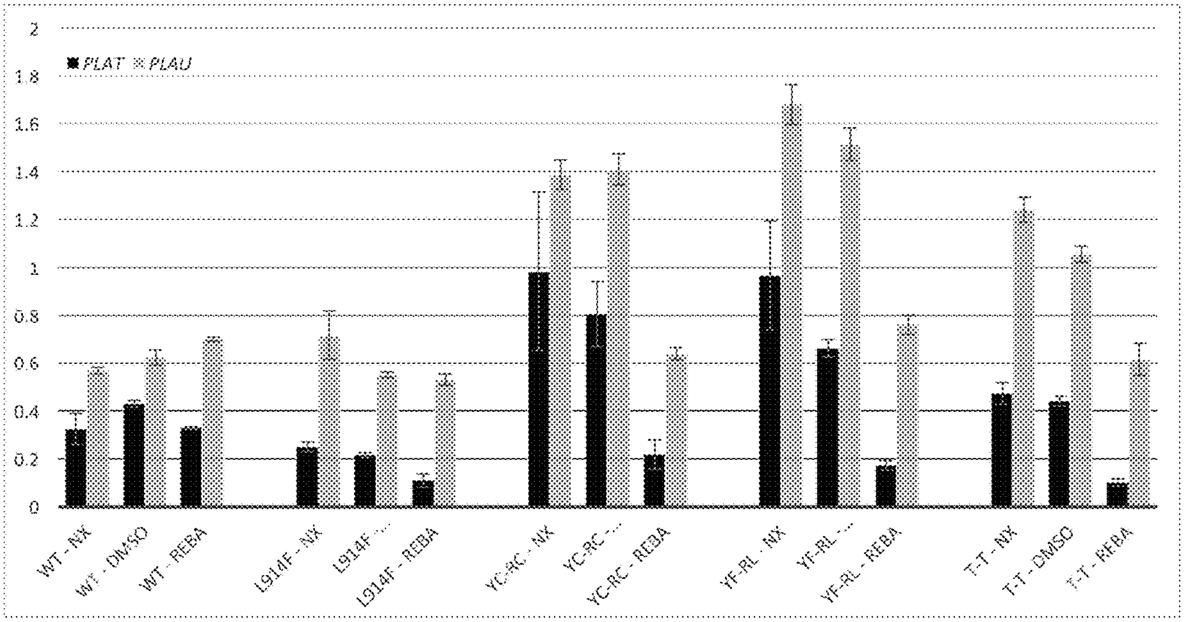

Example 6. Effects on RNA Expression in TIE2 Mutant Human Umbilical Vein Endothelial Cells by the Compound of Formula I Mutant TIE2-Transfected Gene Expression Assay HUVEC cells ($5\times10^5$ cells/plate) stably expressing WT or TIE2 mutants R849W, L914F, R1099*, Y897C/R915C, Y897F/F915L, or T1105N/T1106P were added to a 10 cm plate coated with attachment factor solution (Tebu-Bio, Boechout, Belgium) in endothelial cell growth media (Tebu-Bio, Boechout, Belgium) containing 10% fetal calf serum (Sigma-Aldrich, Diegem, Belgium). Cells were then incubated for 2 days at 37 degrees Celsius, 5% $CO_2$, and 95% humidity. Next, test compound or DMSO was added to the wells (0.068% final DMSO concentration). The plates were then further incubated for 48 hours at 37 degrees Celsius, 5% $CO_2$, and 95% humidity. RNA was extracted by collecting the cells into TriPure isolation reagent (Sigma-Aldrich, Diegem, Belgium). Subsequently, cDNA from extracted RNA was synthesized using RevertAid H Minus first strand cDNA synthesis kit (Thermo Fischer Scientific, Merelbeke, Belgium). Quantitative PCR was carried out using LightCycler480 SYBRGreen master mix and a LightCycler 480 II instrument (Roche, Switzerland). cDNA for ANGPT2, PDGFB, ADAMTS1, ADAMTS9, PLAT, and PLAU were quantified and normalized to the expression from the housekeeping gene GAPDH. The compound of Formula I disclosed herein at a concentration of 100 nM resulted in increased expression of ANGPT2 RNA, which encodes the ligand for TIE2, and is aberrantly downregulated in TIE2 mutant cells. The compound of Formula I disclosed herein at a concentration of 100 nM also resulted in increased expression of PDGFB RNA, which encodes the ligand for PDGFRB, and is aberrantly downregulated in TIE2 mutant cells. The compound of Formula I disclosed herein at a concentration of 100 nM also resulted in decreased expression of ADAMTS1 and ADAMTS9 RNA, which encode extracellular metalloproteinases, whose expression is aberrantly upregulated in mutant TIE2 transfected cells. The compound of Formula I disclosed herein at a concentration of 100 nM also resulted in decreased expression of PLAT and PLAU RNA, which encode plasminogen activators, whose expression is aberrantly upregulated in mutant TIE2 transfected cells. FIG. 6A shows ANGPT2 and PDGFB RNA expression for HUVECs expressing WT TIE2, L914F TIE2, R849W TIE2, and R1099* TIE2. FIG. 6B shows ANGPT2 and PDGFB RNA expression for HUVECs expressing WT TIE2, L914F TIE2, Y897C/R915C TIE2, Y897C/R915L TIE2, and T1105N/T1106P TIE2. FIG. 6C shows ADAMSTS1 and ADAMSTS9 RNA expression for HUVECs expressing WT TIE2, L914F TIE2, R849W TIE2, and R1099* TIE2. FIG. 6D shows ADAMSTS1 and ADAMSTS9 RNA expression for HUVECs expressing WT TIE2, L914F TIE2, Y897C/R915C TIE2, Y897C/R915L TIE2, and T1105N/T1106P TIE2. FIG. 6E shows PLAT and PLAU RNA expression for HUVECs expressing WT TIE2, L914F TIE2, R849W TIE2, and R1099* TIE2. FIG. 6F shows PLAT and PLAU RNA expression for HUVECs expressing WT TIE2, L914F TIE2, Y897C/R915C TIE2, Y897C/R915L TIE2, and T1105N/T1106P TIE2.

Figure 7:
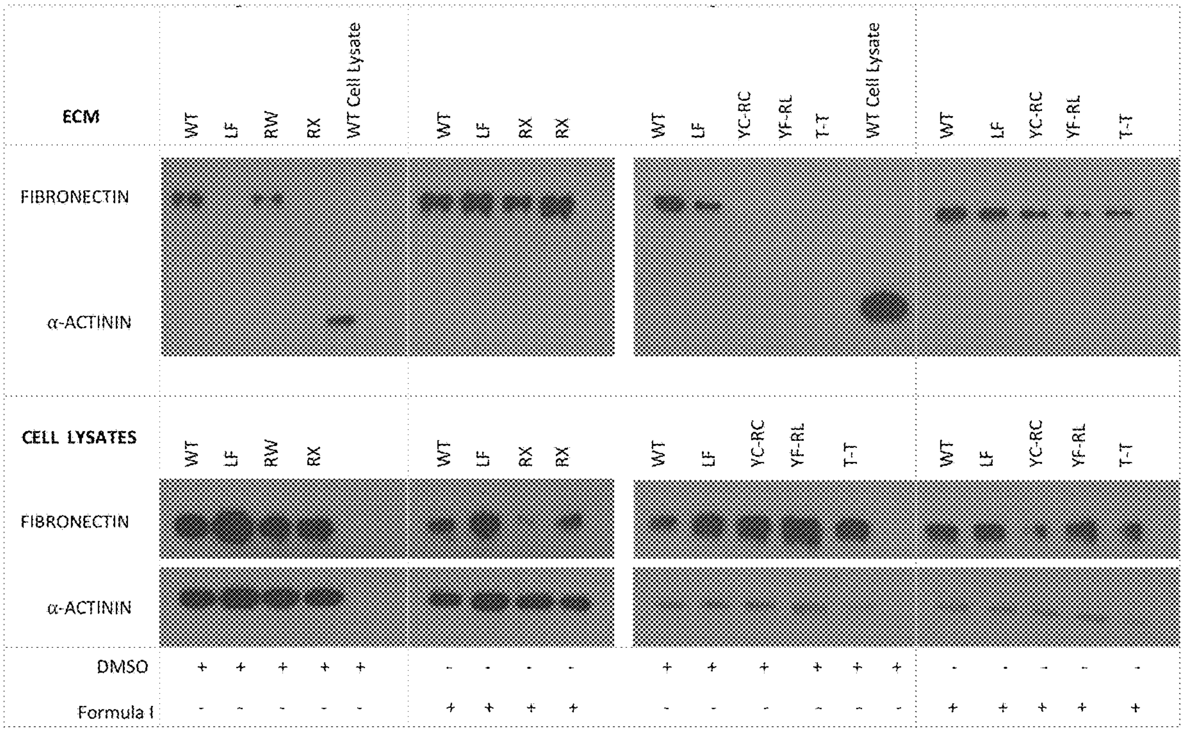
FIG. 7 shows restoration of extracellular fibronectin using the compound of Formula I in assays using transfected human umbilical vein endothelial cells with various mutant forms of TIE2.

Example 6. Restoration of Extracellular Fibronectin in TIE2 Mutant Human Umbilical Vein Endothelial Cells by the Compound of Formula I Mutant TIE2-Transfected Fibronectin Assay HUVEC cells ($3\times10^5$ cells/well) stably expressing WT or TIE2 mutants R849W, L914F, R1099*, Y897C/R915C, Y897F/F915L, or T1105N/T1106P were added to a 6-well plate coated with attachment factor solution (Tebu-Bio, Boechout, Belgium) in endothelial cell growth media (Tebu-Bio, Boechout, Belgium) containing 10% fetal calf serum (Sigma-Aldrich, Diegem, Belgium). Cells were then incubated for 24 hours at 37 degrees Celsius, 5% $CO_2$, and 95% humidity. Next, test compound or DMSO was added to the wells (0.068% final DMSO concentration). The plates were then further incubated for 48 hours at 37 degrees Celsius, 5% $CO_2$, and 95% humidity. Cells were switched into 2% FBS for overnight. Intracellular fibronectin levels were lower in transfectants, thus cellular lysates were collected and used as controls. Regarding the cell remnants, the plate was washed with 1×PBS containing 0.05% Triton-X and 50 nM $NH_4OH$, followed by 50 mM in 1×PBS, then three times with 1×PBS; extracellular matrix proteins were then extracted with a lysis buffer (9.1 mM $Na_2HPO_4$, 1.7 mM $NaH_2PO_4$, 1% NP-40, 0.25% sodium deoxycholate, 150 mM NaCl, 0.1% SDS, 1 mM EDTA) with 6.5M urea. As shown in FIG. 7, in the presence of DMSO treatment, lower levels of fibronectin was seen in the extracellular matrix of TIE2 mutants than in WT extracts (upper blots). Fibronectin levels were comparable to controls in cellular lysates. The compound of Formula I disclosed herein at a concentration of 100 nM restored fibronectin levels in the extracellular matrix of TIE2 mutant expressing HUVECs, leading to levels similar to cells expressing WT TIE2 (FIG. 7).

Example 7. Inhibition of Growth of Mutant TIE2 Human Umbilical Vein Endothelial Cells In Vivo in a Venous Malformation Model by the Compound of Formula I Venous Malformation Mouse Model Evaluation For the in vivo model, fresh HUVEC transfectants were made using lentiviral infection. Briefly, $2\times10^6$ HEK293 cells were plated on a 10 cm dish for 24 hours, trypsinized, then incubated for 20 min with a mixture containing pGAG-Pol, pRSV-Rev, pMD2.VSVG, the lentivirus vector pTM945, 2.5 μg of pTIE2-L914F, $CaCl_2$) (Merck, UK), and 2×HBS (Thermo Fischer Scientific, Merelbeke, Belgium). 1.5 ml of the cells were plated in a 24-well plate and cultured for 48 hrs. Subsequently, 25,000 HUVECs/well (LGC Standards sarl, France) were grown on a 24-well plate for 24 hrs, infected with 500 μl of the lentivirus-TIE2-L914F mix, then cultured for another 48 hrs, collected, then frozen.

Figure 8A:
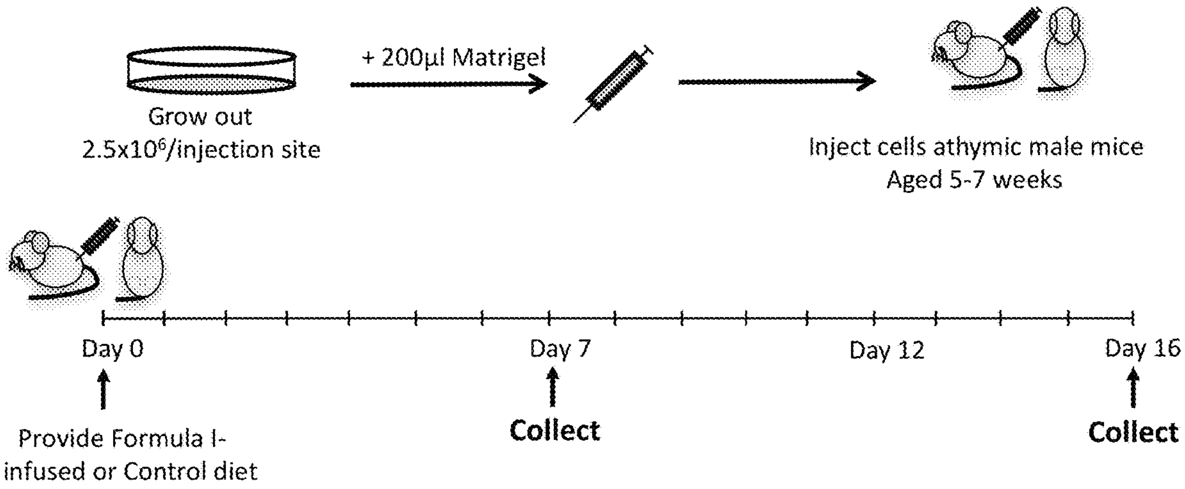
FIG. 8A shows the schematic of the experimental design as described in Example 10 for evaluating the inhibition of growth of mutant TIE2 human umbilical vein endothelial cells in vivo in a venous malformation model by the compound of Formula I, where the mice were given a control diet or diet infused with the compound of Formula I on day 0.

To evaluate the effect of the compound on vascular malformation (VM) lesion development in vivo, HUVEC cells ($2.5\times10^6$) expressing mutant TIE2-L914F were cultured, detached, then resuspended in 200 μL matrigel (Corning). The mixture was injected subcutaneously into the dorsal back of athymic nude male mice, aged 5-7 weeks (Charles River). On the day of injection (Day 0), mice were given a control diet or diet infused with the equivalent concentration of 10 mg/kg compound of Formula I; once introduced, mice had free access to the diet until the point of matrigel plug collection, at post-implant day 7 or 16 (FIG. 8A). At post-implant day 7 or 16, mice were euthanized and the skin surrounding each matrigel plug was excised, then pinned flat onto a styrofoam board and fixed in 10% neutral buffered formalin solution (Sigma-Aldrich, Diegem, Belgium) overnight. Matrigel plugs were removed from the murine skin, dehydrated in a series of graded alcohol, and embedded in paraffin. Paraffin-embedded plugs were then cut into 5 μm sections for histological analysis. After deparaffinization in xylene and rehydration in a series of degraded alcohol, sections were subjected to heat-induced antigen-retrieval in 0.1 M citrate buffer, pH 6.0, with or without 0.05% Tween-20. For immunohistochemical staining, sections were blocked with 3% $H_2O_2$ (Sigma-Aldrich, Diegem, Belgium), incubated with a biotinylated antibody against the human endothelial cell marker *Ulex europaeus* Agglutinin 1 (UEA1) (Vector labs, Brussels, Belgium), followed by a horseradish peroxidase-conjugated streptavidin secondary antibody (GE Healthcare, Diegem, Belgium), then in a DAB solution (Vector labs, Brussels, Belgium). Sections were counterstained with hematoxylin and mounted with VectaMount permanent mounting medium (Vector labs, Brussels, Belgium). For immunofluorescent staining (IF), sections were incubated with primary antibodies that recognize UEA1, the smooth muscle layer marker SMA (clone 1A4, Sigma-Aldrich, Diegem, Belgium), phosphorylated-TIE2(Y772) (Bioke, Leiden, Netherlands), or total TIE2 (Santa Cruz, Heidelberg, Germany). Secondary antibodies used were conjugated to Alexa488-, Alexa649-, or CY5-fluorophores. Slides were mounted with VectaShield Hardset mounting medium with DAPI (Vector labs, Brussels, Belgium). Images were acquired via a Panoramic 250 Flash III digital slide scanner (3D Histech, Hungary) and visualized with Caseviewer version 2.2 software (3D Histech, Hungary). The average vessel area was quantitated by making snapshots at a 20× objective of at least 5 areas of each matrigel plug and measuring the area of a least 6 UEA+ vessels each using ImageJ software.

Figure 8B:
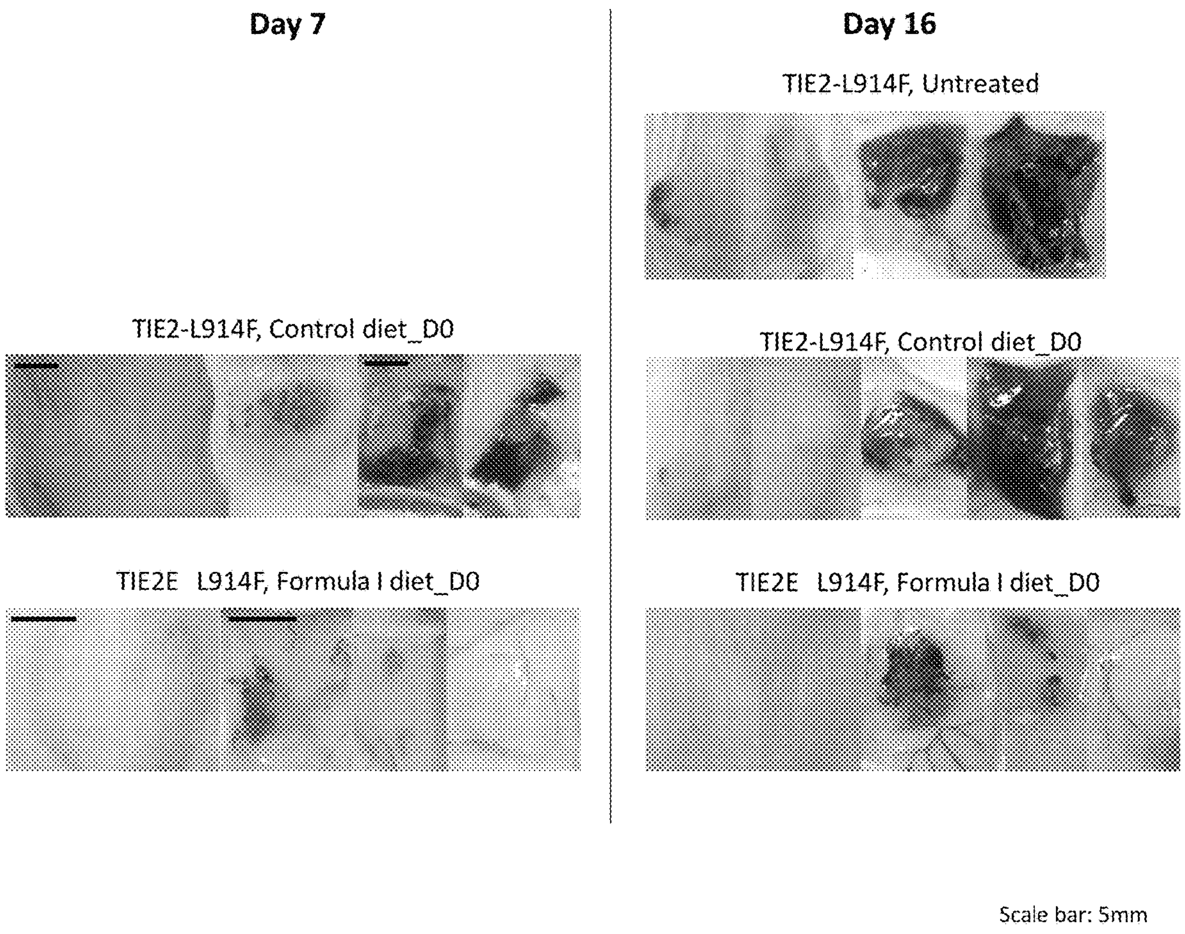
FIG. 8B shows the effects of the compound of Formula I on gross appearance of mutant TIE2 blood vessel lesions in an in vivo model of venous malformation on day 7.
Figure 9:
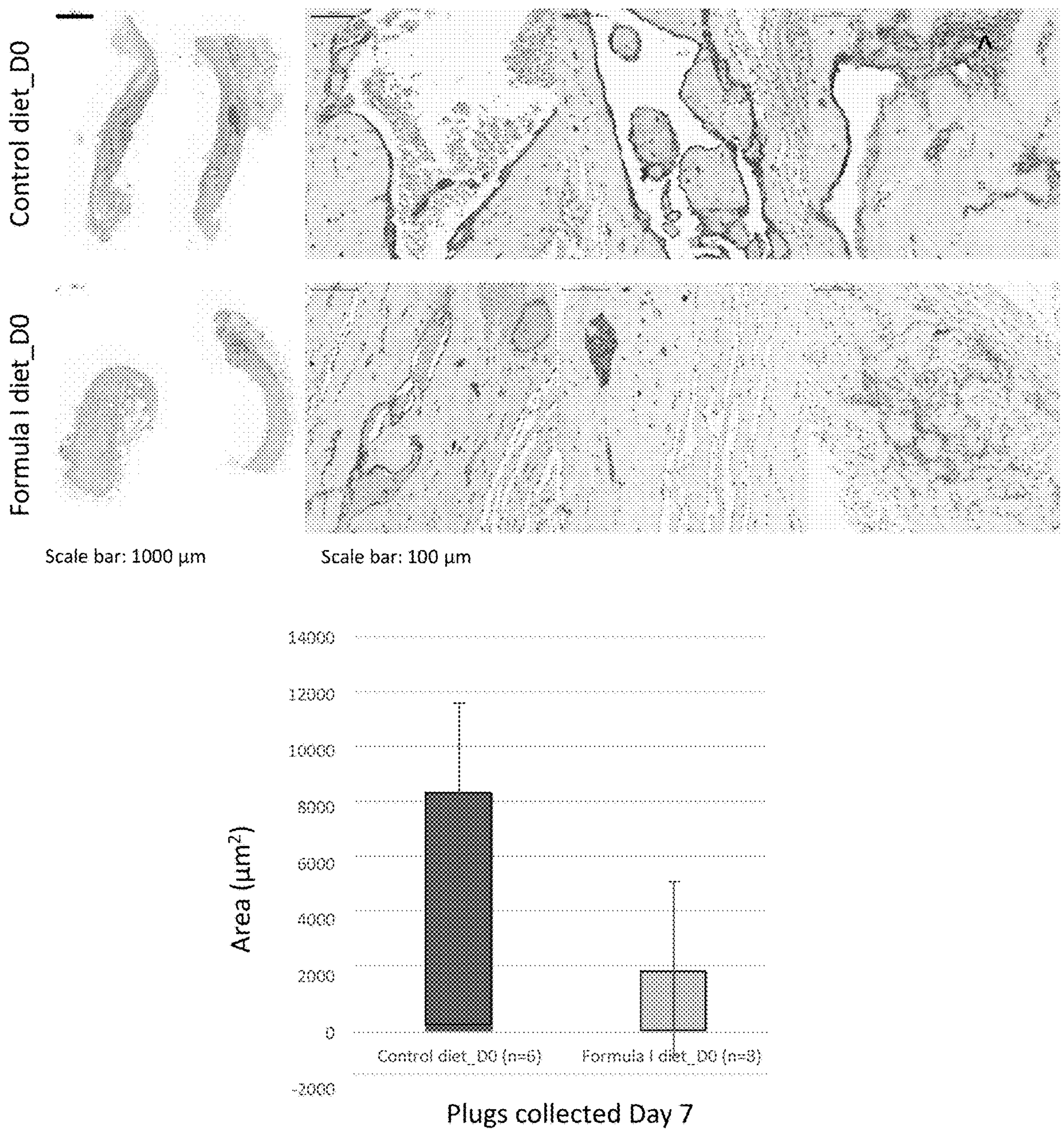
FIG. 9 shows the effects of the compound of Formula I on the size of mutant TIE2 blood vessel lesions in an in vivo model of venous malformation on day 7.

In FIG. 8B, Macroscopic views of collected lesions show that blood-filled venous channels were established by day 7 (D7) post-implantation and developed more severely at Day 16, in mice fed a regular or control diet. Some mice fed a diet with the compound of Formula I did not develop any lesions within the matrigel plugs; blood-filled vascular channels that did form appeared to be more controlled and less severe, compared to the untreated mutants. FIG. 9 reveals, in representative images of UEA1 staining of plugs from mice given control diet 7 days post-implantation, enlarged venous channels and patches of disorganized endothelial cells (ECs). However, within plugs from compound of Formula I-treated mice, less grossly dilated vessels formed. There is evidence that the clusters of UEA1+ ECs are more migratory than in the control. There are also several non-vascularized UEA1+ cells. Additionally, the average area of vessels within the plugs taken from mice treated with the compound of Formula I was drastically less than those fed the control diet.

Figure 10:
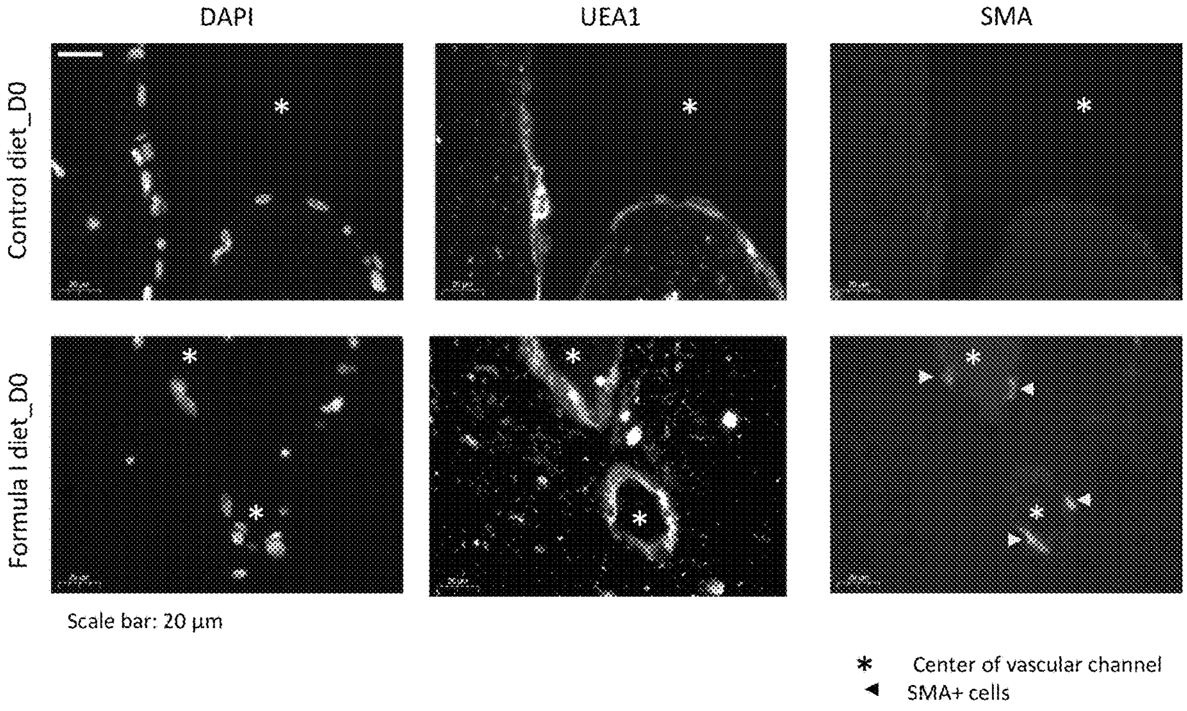
FIG. 10 shows the effects of the compound of Formula I on the smooth muscle cell and pericyte coverage of mutant TIE2 blood vessel lesions in an in vivo model of venous malformation on day 7.
Figure 11:
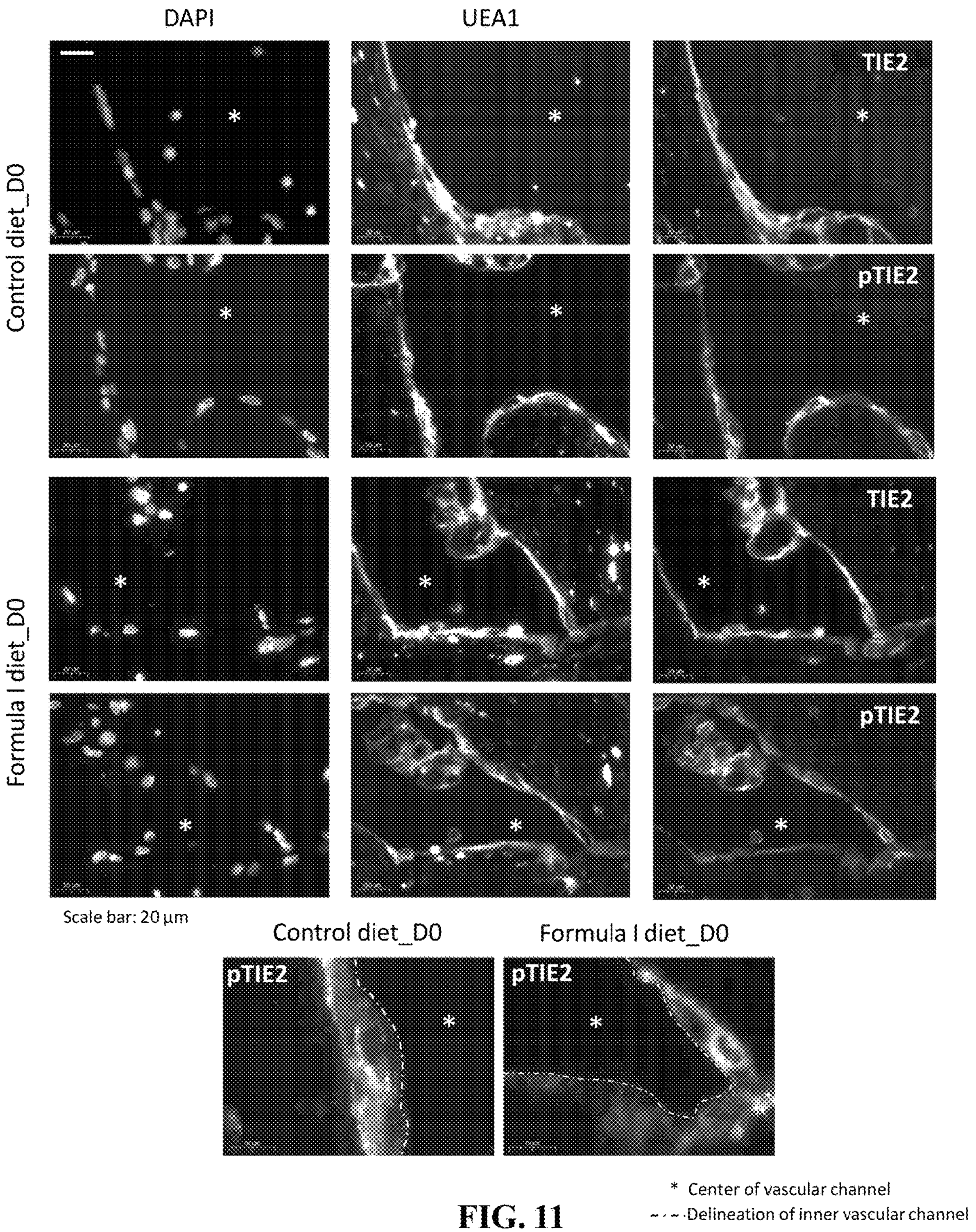
FIG. 11 shows the effects of the compound of Formula I on phosphorylation of TIE2 in mutant TIE2 blood vessel lesions in an in vivo model of venous malformation on day 7.

One of the hallmarks of VM lesions is poor, inconsistent smooth muscle cell/pericyte coverage of the dilated venous channels. IF staining of lesions reveals that the vessels are surrounded by no or weakly positive SMA cells in control diet fed mice in FIG. 10. Those of compound of Formula I fed mice displayed a few SMA positive cells but not in all cells surrounding the EC layer. All ECs of vessels from both control- and compound of Formula I diet fed mice strongly express total TIE2; likewise, all ECs appear to express phosphorylated-TIE2 (pTIE2) in control diet fed mice, as demonstrated in FIG. 11. Expression of pTIE2 appeared weaker in ECs of mice given the compound of Formula I diet.

Figure 12:
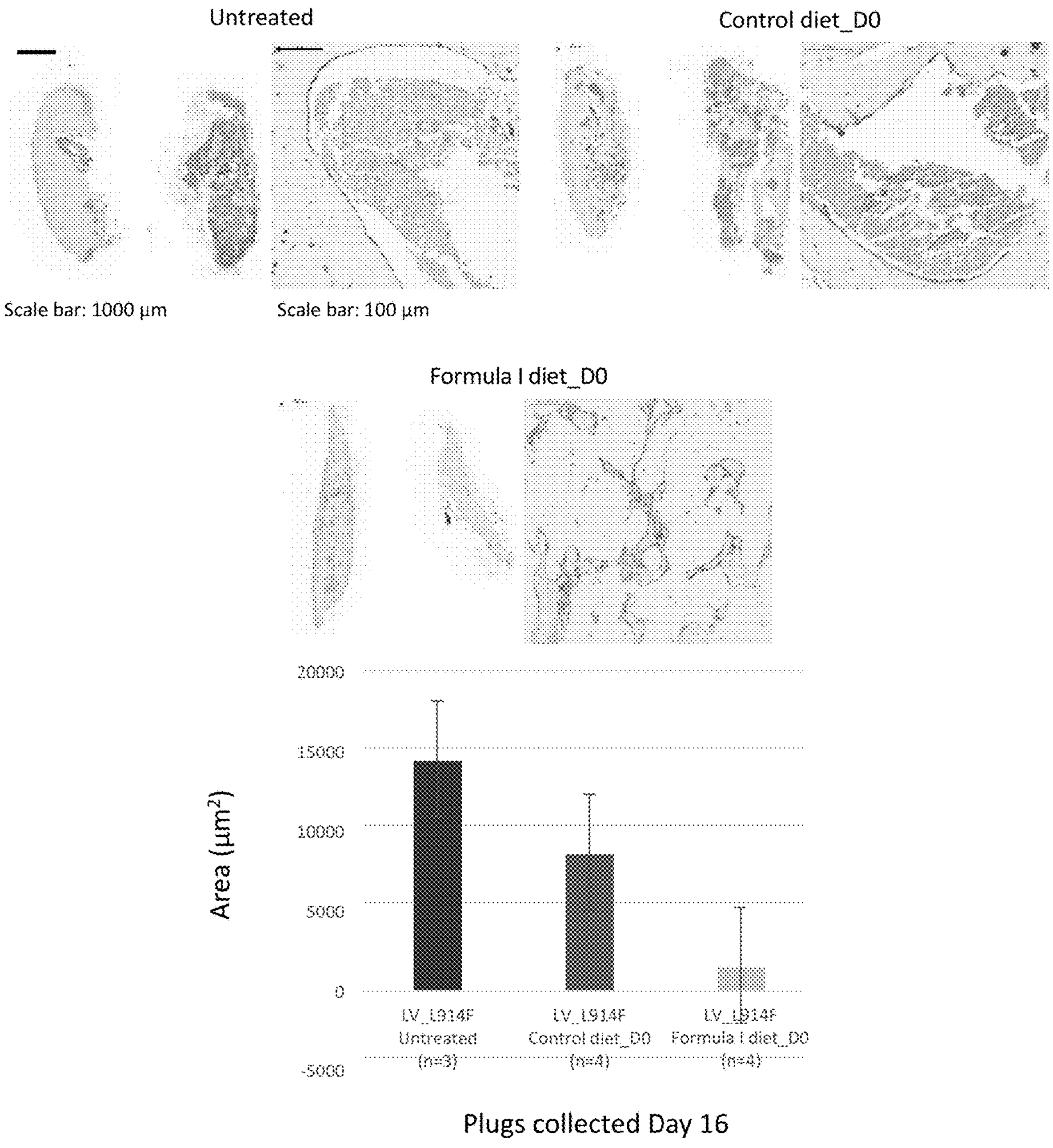
FIG. 12 shows the effects of the compound of Formula Ion the size of mutant TIE2 blood vessel lesions in an in vivo model of venous malformation on day 16.
Figure 13:
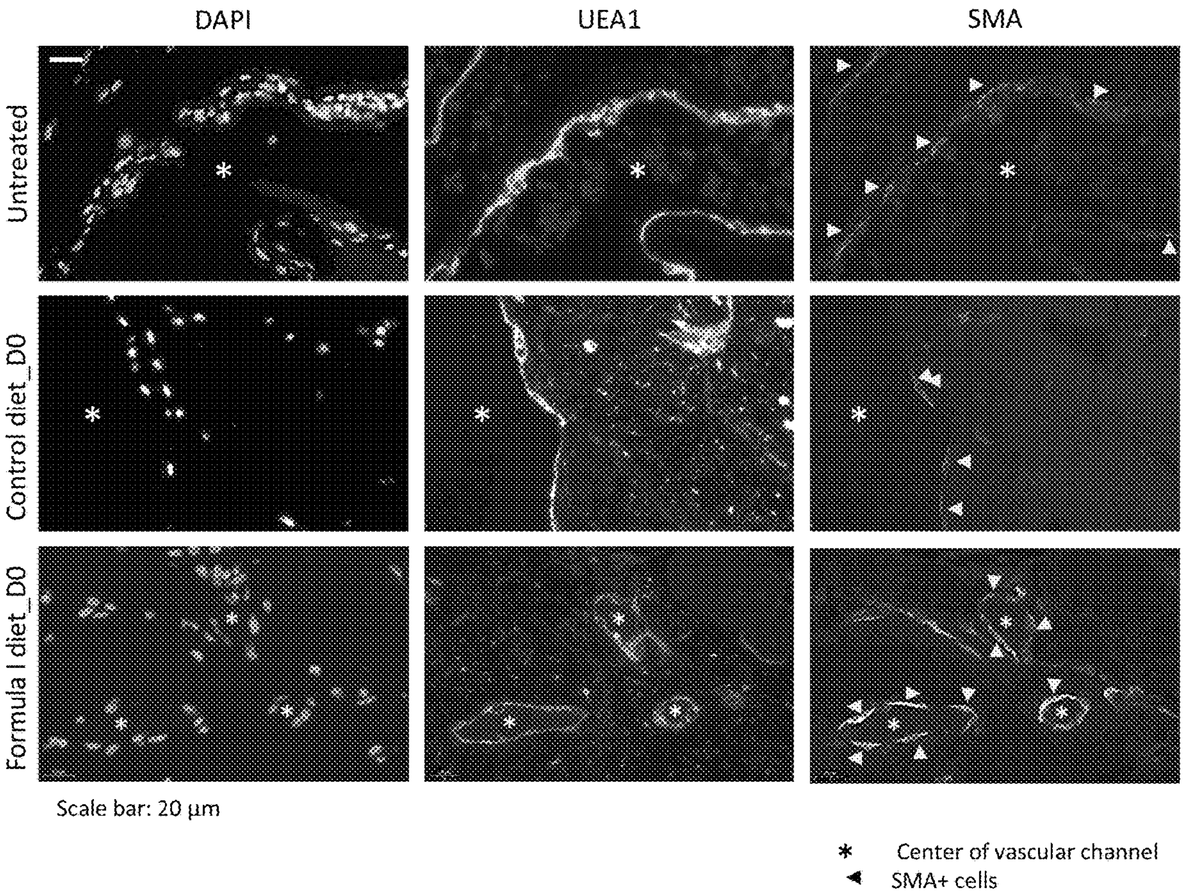
FIG. 13 shows the effects of the compound of Formula I on the smooth muscle cell and pericyte coverage of mutant TIE2 blood vessel lesions in an in vivo model of venous malformation on day 16.
Figure 14:
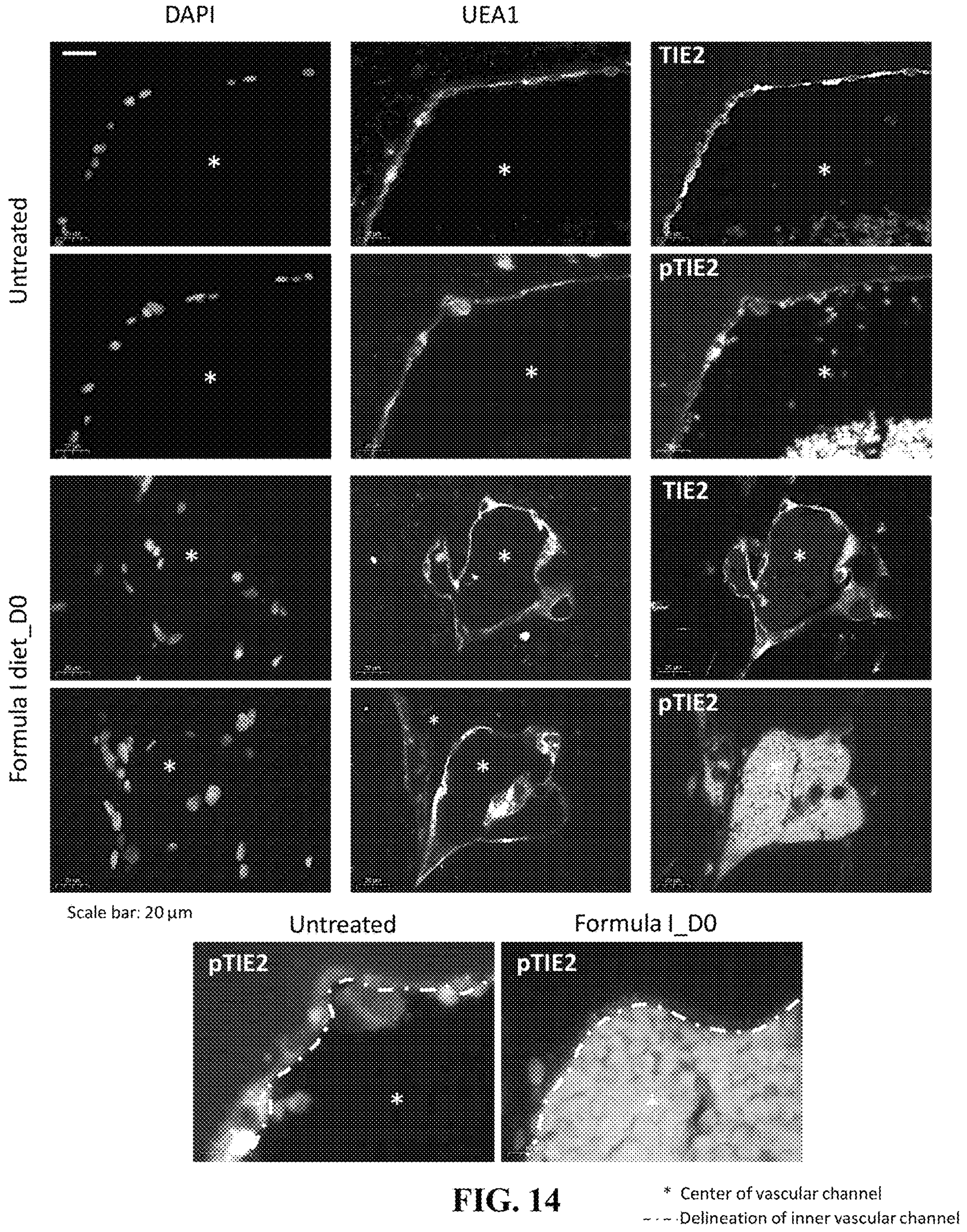
FIG. 14 shows the effects of the compound of Formula I on phosphorylation of TIE2 in mutant TIE2 blood vessel lesions in an in vivo model of venous malformation on day 16.

By day 16 post-implantation, lesions within the matrigels became grossly enlarged, though some variability was seen, likely more due to technical/manipulation issues (e.g. non-homogenous mixture of cells with the matrigel (FIG. 12). Control diet-fed mice developed lesions that were comparable to untreated mice, but mice fed the compound of Formula I diet revealed much smaller vessels. Day 16 explants developed enlarged vascular channels that were sparsely surrounded by a smooth muscle layer, with few SMA+ cells, within the untreated and control diet-fed mice. Conversely, in compound of Formula I-fed mice, vessels appeared normalized and surrounded more consistently by SMA+ cells (FIG. 13). FIG. 14 reveals that the ECs in untreated mice strongly express pTIE2. However, in compound of Formula I-fed mice, pTIE2 was drastically reduced.

Figure 15:
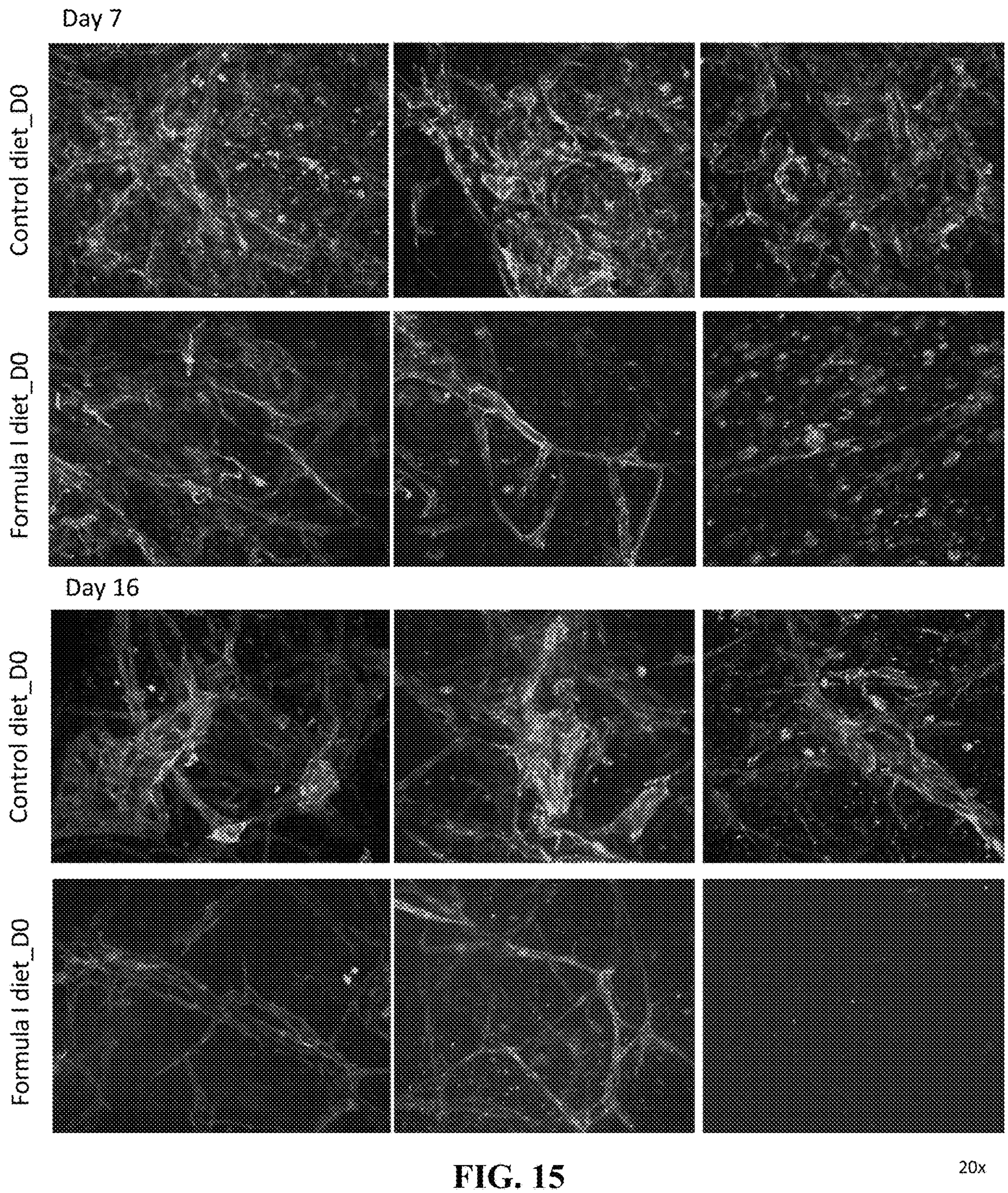
FIG. 15 shows the effects of the compound of Formula I on vascular morphology of mutant TIE2 blood vessel lesions in an in vivo model of venous malformation on days 7 and 16.
Figure 19A:
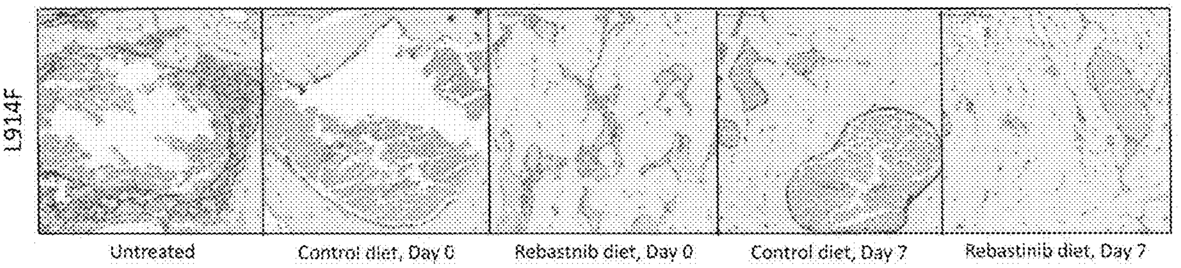
FIG. 19A-C provide comparisons of treatment of vascular malformation (VM) lesions expressing wild type and L914F TIE2 mutants from the day of injection (Day 0) to Day 16, or from Day 7 to Day 16. Comparisons include microscopic views of untreated VM lesions and VM lesions expressing TIE2 L914F treated with the compound of Formula I diet and control diet (FIG. 19A) and quantification of vascular area of vessels in lesions expressing TIE2 wild type or L914F (FIG. 19B and FIG. 19C).
Figure 19B:
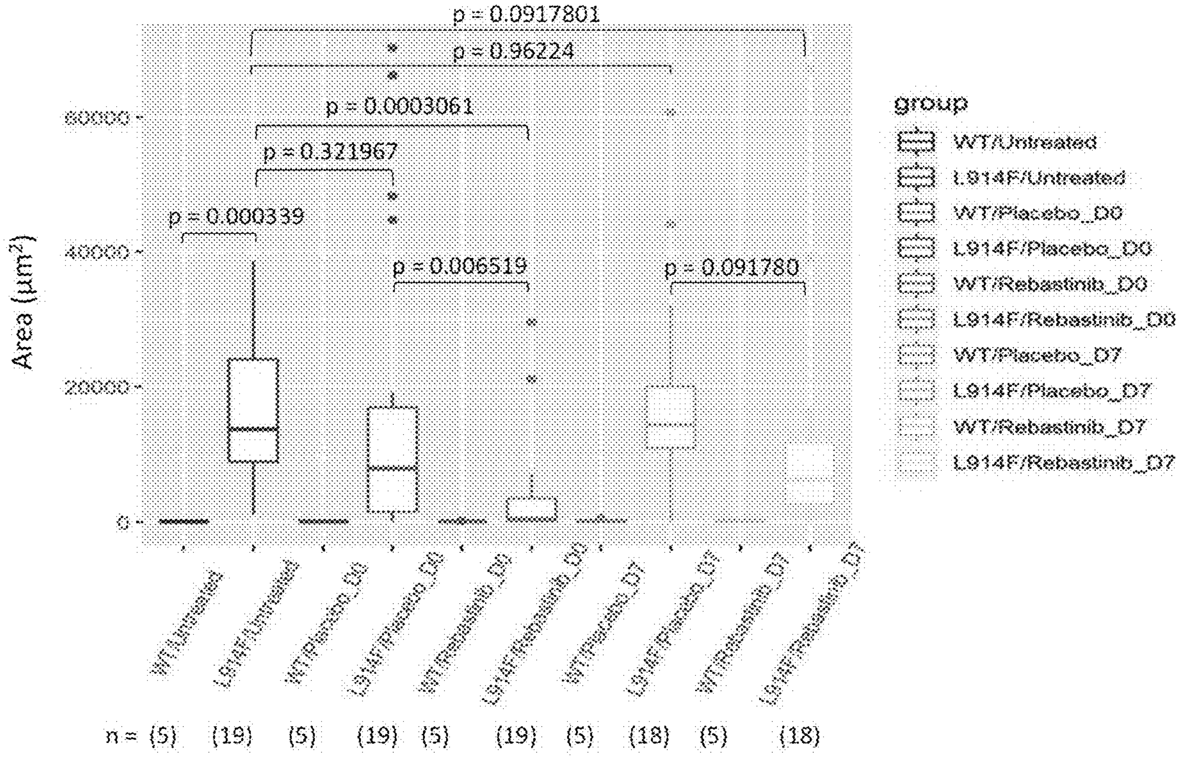
Figure 19C:
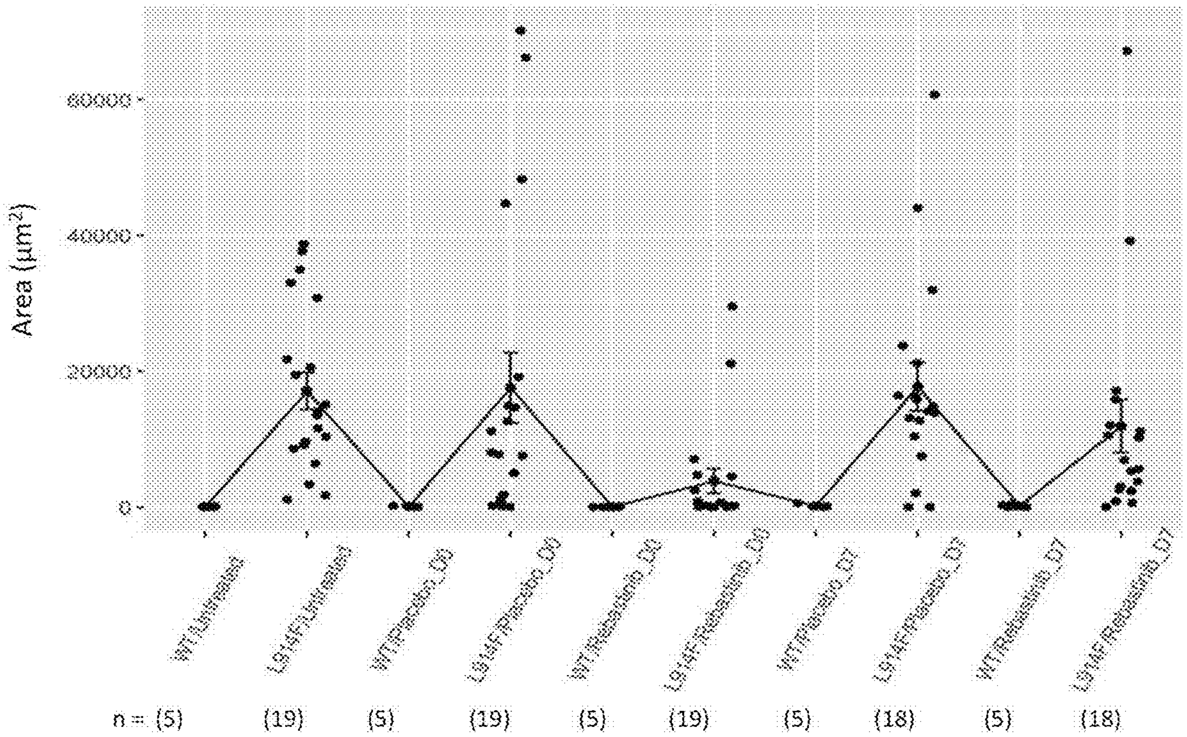

To evaluate the overall vascular morphology within the explants, wholemount IF of vessels within matrigel plugs was done. After excising skins with matrigel plugs attached and flat-fixing them overnight in 10% neutral buffered formalin, an approximately 100-200 μm piece of the plug was sliced off and washed in 1×PBS. The pieces were blocked overnight in 1% BSA (v/v) (Gibco) and 0.3% Triton-X100 (Sigma-Aldrich, Diegem, Belgium) in 1×PBS, then incubated in UEA1 for at least 72 hours, followed by in CY5-streptavidin secondary antibody (Vector labs, Brussels, Belgium). Pieces were then post-fixed in 10% NBF for 10 min, then mounted with Fluormount G (Thermo Fischer Scientific, Merelbeke, Belgium). Z-stack images were acquired with a Zeiss cell observer spinning disk confocal microscope (Zeiss, Germany); 3-D projections of Z-stacks were generated by the AriVis4D software. FIG. 15 shows that in mice fed the control diet, vessels that formed within the matrigel plugs were abnormally stretched and disorganized, at both day 7 and day 16 post-implant. In day 7, explants taken from compound of Formula I-fed mice, some enlarged and clustered vessels were seen; however, more normal, tubular vessels were seen. Many non-vascularized UEA+ cells were also seen; to note, this is the same pattern that TIE2-WT cells exhibit when injected. At day 16, vessels appear largely normalized, with uniform, tube-like structures. Non-vascularized UEA+ cells were also present but the expression is reduced. Also conducted were comparisons of treated and untreated VM lesions at day 16 with wild type and L914F TIE2 mutants in which treatment began at day 0 (FIG. 18A-D) or day 7 (FIG. 19A-C). The data support that feeding mice with VMs with compound of Formula I-infused food results in reduced VM development and that feeding the compound of Formula I to mice with established VMs ameliorated the severity of VMs.

Figure 16A:
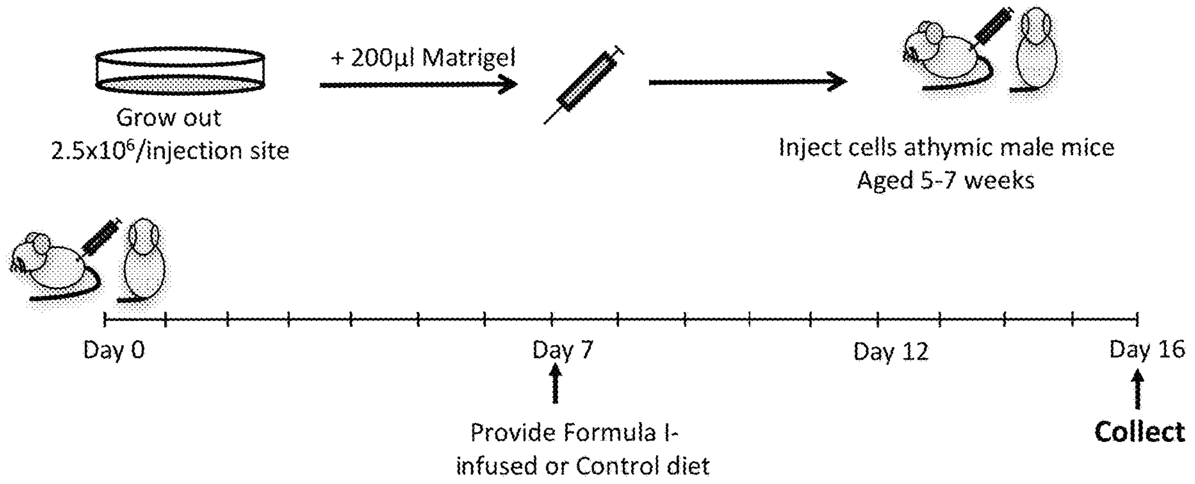
FIG. 16A shows the schematic of the experimental design as described in Example 10 for evaluating the inhibition of growth of mutant TIE2 human umbilical vein endothelial cells in vivo in a venous malformation model by the compound of Formula I, where the mice were given a control diet or diet infused with the compound of Formula I on day 7.
Figure 16B:
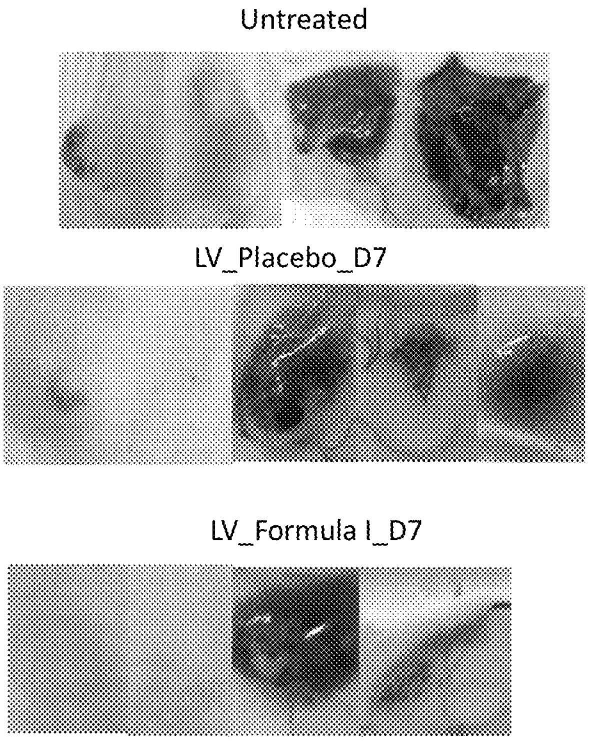
FIG. 16B shows the effects of the compound of Formula I on gross appearance of previously established mutant TIE2 blood vessel lesions in an in vivo model of venous malformation.
Figure 17A:
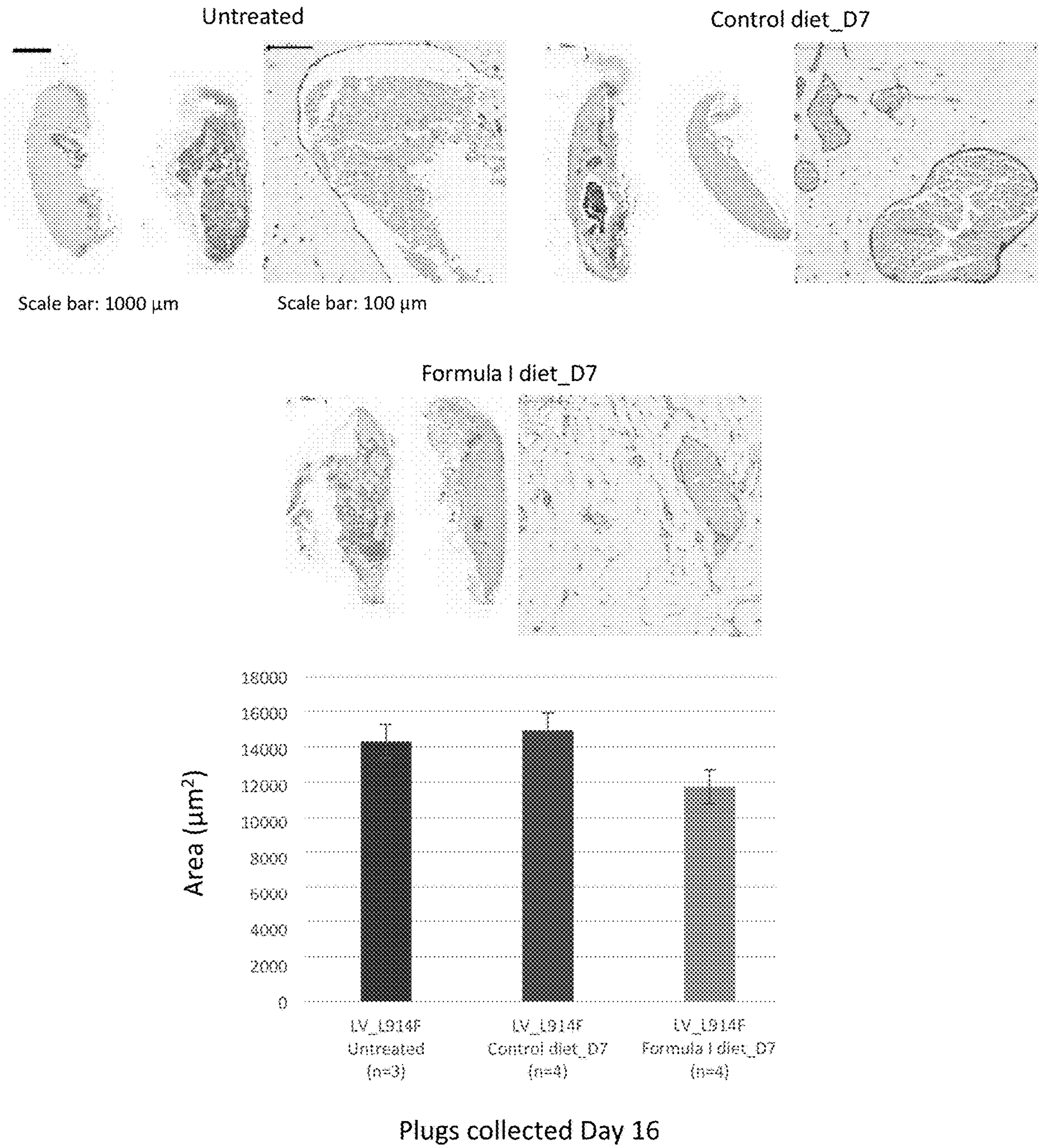
FIGS. 17A-B shows the effects of the compound of Formula I on the size of previously established mutant TIE2 blood vessel lesions and on smooth muscle cell and pericyte coverage of mutant TIE2 blood vessel lesions in an in vivo model of venous malformation.
Figure 17B:
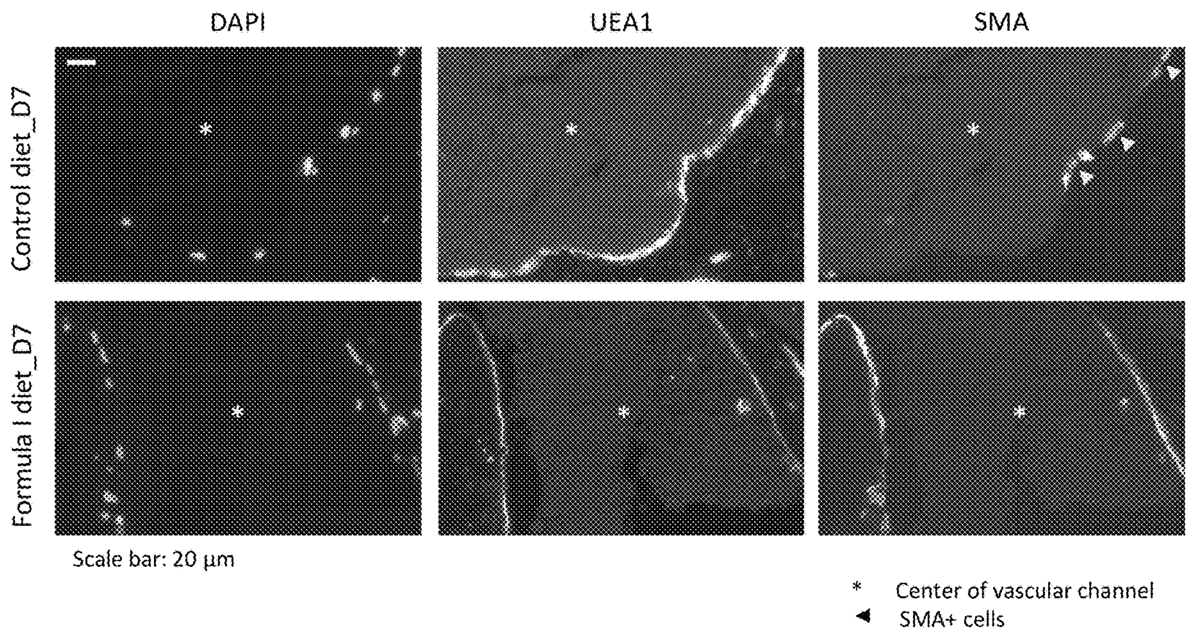
Figure 18A:
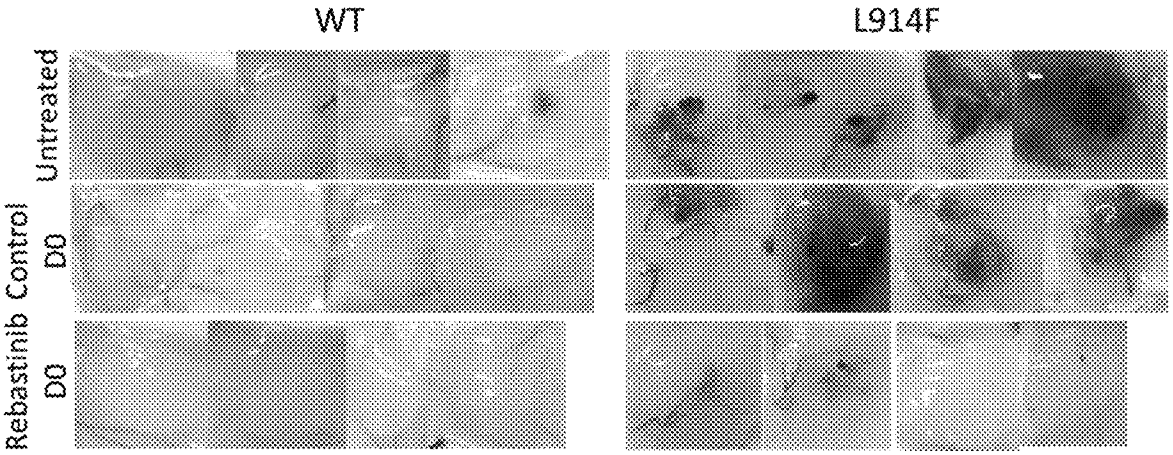
FIG. 18A-D compares the effects of the compound of Formula I on vascular malformation (VM) lesions expressing wild type and L914F TIE2 mutants from the day of injection (Day 0) to Day 7. Treatment with the compound of Formula I diet is compared with treatment with control diet and untreated VM lesions through macroscopic (FIG. 18A) and microscopic (FIG. 18B) images and quantification of vascular area of vessels (FIG. 18C and FIG. 18D).
Figure 18B:
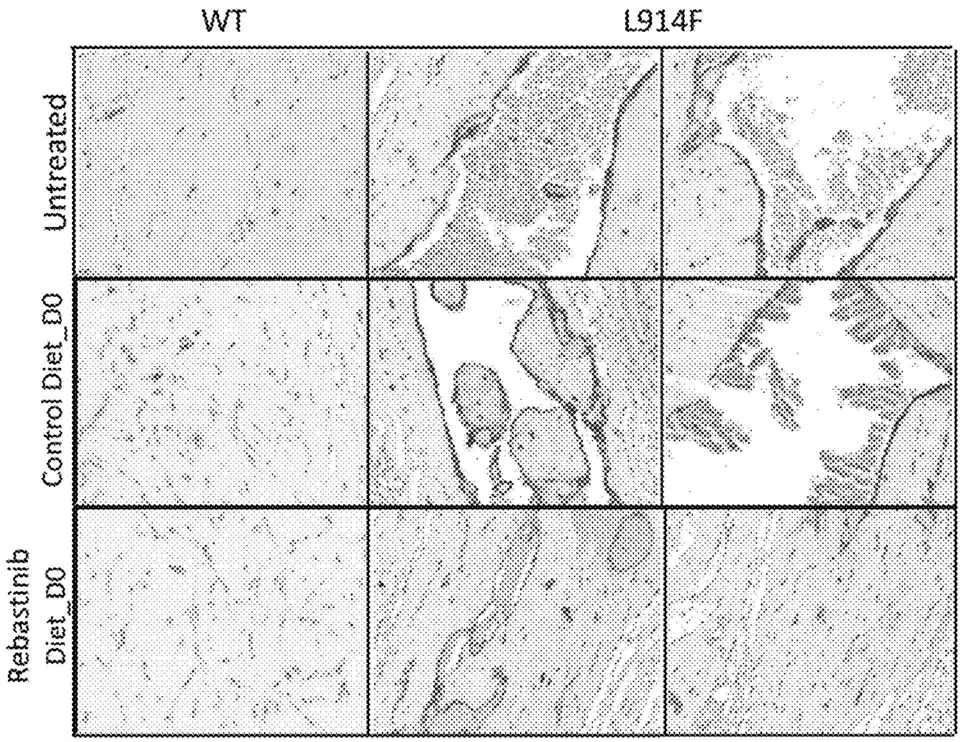
Figure 18C:
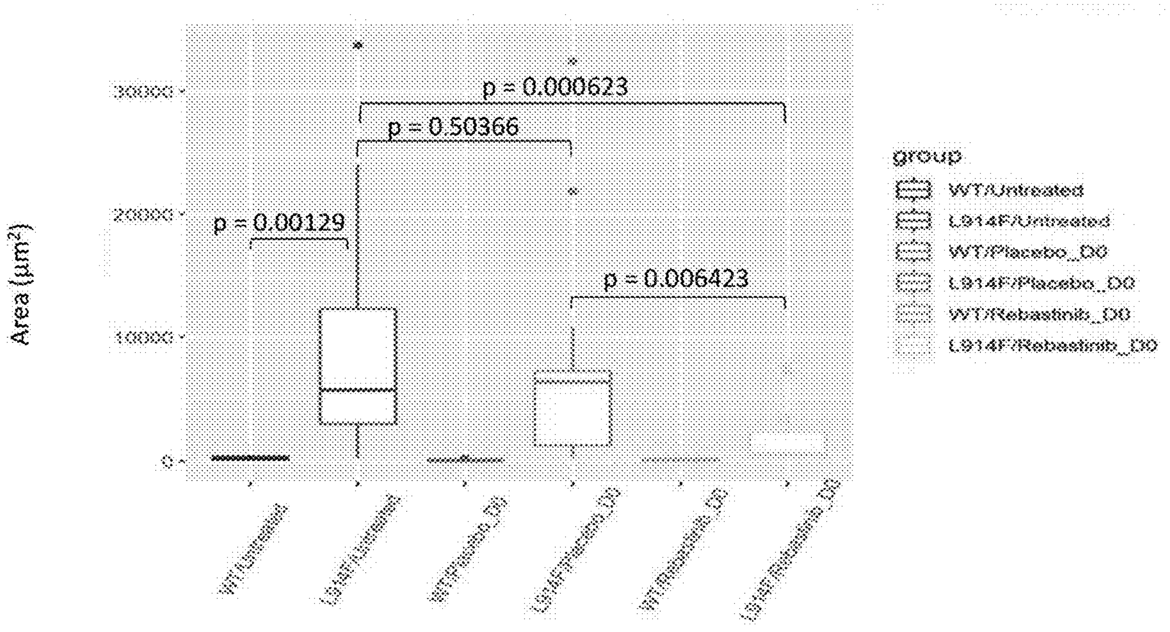
Figure 18D:
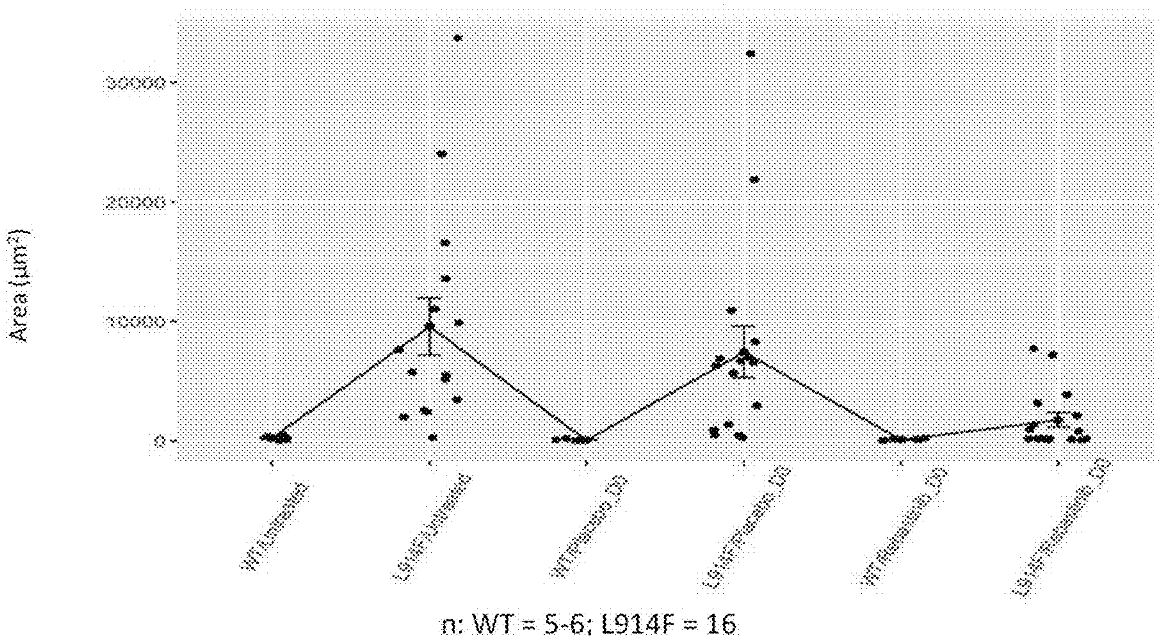

To evaluate whether the compound of Formula I has an effect on previously established VM lesions, the same approach in generating the VM mice was followed. However, the mice were introduced to the control or compound of Formula I diet at post-implant day 7 instead; then, mice were euthanized and explants collected by day 16 (FIG. 16A). Blood-filled vascular channels developed in all experimental groups, though severity varied greatly (FIG. 16B). Average vascular area of vessels within day 16 explants from control diet-fed mice was comparable to control mice, as demonstrated in FIG. 17A-B. The average vascular area of vessels from compound of Formula I diet fed mice was moderately reduced. Lesions from mice fed the compound of Formula I diet exhibited improved smooth muscle cell layer coverage, compared to those of control diet-fed mice, indicating enhanced pericyte stabilization and vascular maturation. FIG. 19A-D also depict, in part, comparisons of treated and untreated VM lesions with wild type or L914F TIE2 mutants at day 16 in which treatment began at post-implant day 7. The data support that feeding the compound of Formula I to mice with established VMs ameliorated the severity of VMs.

EQUIVALENTS

Those skilled in the art will recognize, or be able to ascertain, using no more than routine experimentation, numerous equivalents to the specific embodiments described specifically herein. Such equivalents are intended to be encompassed in the scope of the following claims.

The invention claimed is:

1. A method for reducing the average vascular area of TIE2 kinase-mediated vascular anomalies or TIE2 kinase mutant-mediated vascular anomalies, in a human patient in need thereof, consisting of administering to the patient a pharmaceutical composition comprising a compound of Formula I:

Formula I

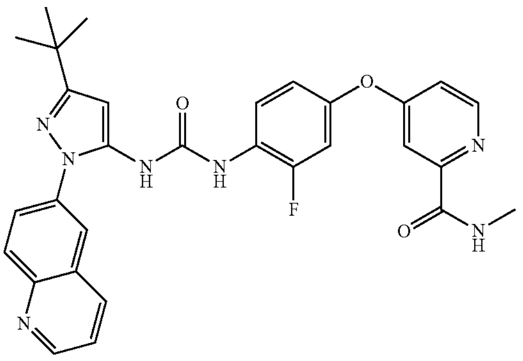

or a pharmaceutically acceptable salt thereof, and a pharmaceutically acceptable excipient, in an amount sufficient to administer the patient about 25 mg to about 300 mg, once or twice daily, of the compound, wherein the compound is administered to the patient as a single agent.

2. The method of claim 1, wherein the pharmaceutically acceptable salt is tosylate.

3. The method of claim 1, wherein the TIE2 kinase-mediated vascular anomalies or TIE2 kinase mutant-mediated vascular anomalies are slow-flow malformations.

4. The method of claim 3, wherein the slow-flow malformations are selected from capillary malformations, lymphatic malformations, or venous malformations.

5. The method of claim 4, wherein the slow-flow malformations are venous malformations.

6. The method of claim 1, wherein the patient is administered about 25 mg to about 150 mg of the compound of Formula I once or twice daily.

7. The method of claim 1, wherein the patient is administered about 100 mg of the compound of Formula I once or twice daily.

8. The method of claim 1, wherein the patient is administered about 150, 200, or 300 mg of the compound of Formula I once or twice daily.

9. A method for reducing the average vascular area of venous malformations in a human patient in need thereof, consisting of administering to the patient a pharmaceutical composition comprising a compound of Formula I:

Formula I

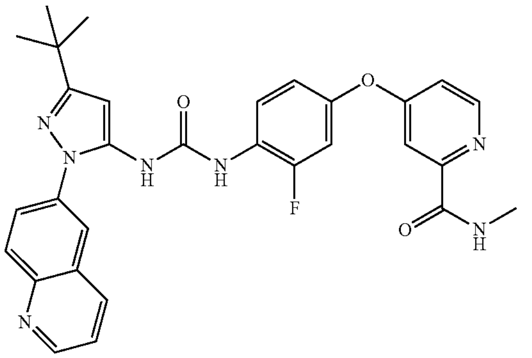

or a pharmaceutically acceptable salt thereof, and a pharmaceutically acceptable excipient, in an amount sufficient to administer the patient about 100 mg to about 200 mg, once or twice daily, of the compound, wherein the compound is administered to the patient as a single agent.

10. The method of claim 1, wherein the patient is administered about 25 mg of the compound of Formula I once daily.

11. The method of claim 1, wherein the patient is administered about 25mg of the compound of Formula I twice daily.

12. The method of claim 1, wherein the patient is administered about 50 mg of the compound of Formula I once daily.

13. The method of claim 1, wherein the patient is administered about 50 mg of the compound of Formula I twice daily.

* * * * *